United States Patent
Hu et al.

(10) Patent No.: US 10,738,028 B2
(45) Date of Patent: Aug. 11, 2020

(54) SPIRO THREE-MEMBERED RING, SPIRO FIVE-MEMBERED RING PEPTIDE DEFORMYLASE INHIBITOR AND USE THEREOF IN ANTIBACTERIA AND ANTI-TUMOR

(71) Applicant: Rudong Ruien Pharmaceutical Technology Co. Ltd, Jiangsu (CN)

(72) Inventors: Wenhao Hu, Guangzhou (CN); Fengping Lv, Shanghai (CN); Yang Tang, Shanghai (CN); Ziyan Li, Shanghai (CN); Chen Chen, Shanghai (CN); Jianhai Wei, Shanghai (CN); Suzhen Dong, Shanghai (CN); Yu Qian, Shanghai (CN)

(73) Assignee: RUDONG RUIEN PHARMACEUTICAL TECHNOLOGY CO. LTD, Jiangsu (CN)

( * ) Notice: Subject to any disclaimer, the term of this patent is extended or adjusted under 35 U.S.C. 154(b) by 64 days.

(21) Appl. No.: 16/300,191

(22) PCT Filed: May 10, 2017

(86) PCT No.: PCT/CN2017/083698
§ 371 (c)(1),
(2) Date: Mar. 12, 2019

(87) PCT Pub. No.: WO2017/193924
PCT Pub. Date: Nov. 16, 2017

(65) Prior Publication Data
US 2019/0194165 A1  Jun. 27, 2019

(30) Foreign Application Priority Data

May 11, 2016  (CN) .......................... 2016 1 0310684
May 11, 2016  (CN) .......................... 2016 1 0310999
May 11, 2016  (CN) .......................... 2016 1 0311289

(51) Int. Cl.
*C07D 401/12* (2006.01)
*C07D 403/12* (2006.01)
(Continued)

(52) U.S. Cl.
CPC ........ *C07D 401/12* (2013.01); *A61K 31/4155* (2013.01); *A61P 31/04* (2018.01);
(Continued)

(58) Field of Classification Search
CPC .. C07D 209/54; C07D 401/12; C07D 401/14; C07D 403/04; C07D 403/12;
(Continued)

(56) References Cited

U.S. PATENT DOCUMENTS

2002/0115863 A1   8/2002  Jacobs et al.
2005/0277683 A1  12/2005  Jacobs et al.
(Continued)

FOREIGN PATENT DOCUMENTS

CN  1512991 A  7/2004
CN  1764450 A  4/2006
(Continued)

OTHER PUBLICATIONS

International Search Report and Written Opinion dated Jul. 28, 2017 in International Application PCT/CN2017/083698.

*Primary Examiner* — Valerie Rodriguez-Garcia
(74) *Attorney, Agent, or Firm* — Pillsbury Winthrop Shaw Pittman LLP

(57) ABSTRACT

Disclosed are the anti-bacterial activity and the anti-tumor activity of a class of new spiro three-membered ring and spiro five-membered ring peptide deformylase inhibitor. The spiro three-membered ring and spiro five-membered ring peptide deformylase inhibitor of the present invention, as a class of new anti-bacterial agent, are effective against many antibiotic-resistant Gram-positive strains by inhibiting the activity of the peptide deformylase required in the synthesis of bacterial proteins, and do not affect the synthetic process of the main proteins of the human body, thus selectively killing bacteria. The spiro three-membered ring and spiro five-membered ring peptide deformylase inhibitor of the present invention, as a class of new anti-bacterial agent, can affect the energy balance of the cancer cells through inhibiting the peptide deformylase of the mitochondria in the cells, so that the mitochondrial membrane is depolarized, ATP is exhausted and cell apoptosis is promoted, and has good inhibitory activities on many cancer cell strains such as colorectal cancer, leukemia, lung cancer, gastric cancer, cervical cancer, breast cancer, prostatic cancer, liver cancer and osteosarcoma at relatively lower concentrations. The structure of exemplary invention spiro three-membered ring and spiro five-membered ring peptide deformylase inhibitors are represented by one or more of:

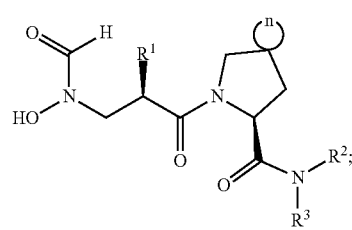

formula (1)

(Continued)

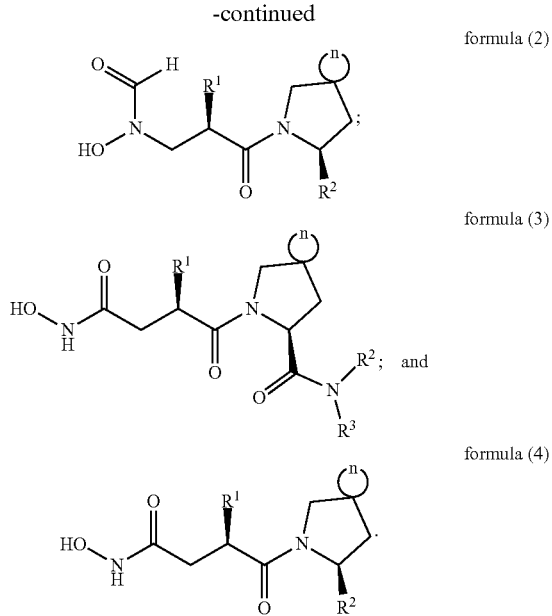

formula (2)

formula (3)

formula (4)

10 Claims, No Drawings

(51) Int. Cl.
  *C07D 401/14* (2006.01)
  *C07D 413/14* (2006.01)
  *C07D 403/04* (2006.01)
  *C07D 413/12* (2006.01)
  *C07D 417/12* (2006.01)
  *C07D 471/04* (2006.01)
  *A61K 31/4155* (2006.01)
  *C07D 209/54* (2006.01)
  *A61P 33/00* (2006.01)
  *A61P 31/04* (2006.01)
  *A61P 35/00* (2006.01)

(52) U.S. Cl.
  CPC ............... *A61P 33/00* (2018.01); *A61P 35/00* (2018.01); *C07D 209/54* (2013.01); *C07D 401/14* (2013.01); *C07D 403/04* (2013.01); *C07D 403/12* (2013.01); *C07D 413/12* (2013.01); *C07D 413/14* (2013.01); *C07D 417/12* (2013.01); *C07D 471/04* (2013.01)

(58) Field of Classification Search
  CPC .. C07D 413/12; C07D 413/14; C07D 417/12; C07D 471/04
  See application file for complete search history.

(56) References Cited

U.S. PATENT DOCUMENTS

| | | |
|---|---|---|
| 2007/0135353 A1 | 6/2007 | Slade et al. |
| 2008/0161558 A1 | 7/2008 | Bracken et al. |
| 2009/0318445 A1 | 12/2009 | Pichota et al. |

FOREIGN PATENT DOCUMENTS

| | | |
|---|---|---|
| CN | 101193882 A | 6/2008 |
| CN | 101346370 A | 1/2009 |
| CN | 101434570 A | 5/2009 |

SPIRO THREE-MEMBERED RING, SPIRO FIVE-MEMBERED RING PEPTIDE DEFORMYLASE INHIBITOR AND USE THEREOF IN ANTIBACTERIA AND ANTI-TUMOR

TECHNICAL FIELD

The invention belongs to the field of anti-bacterial and anti-cancer drug technology, and relates to a kind of peptide deformylase inhibitor, in particular to a novel spiro three-membered ring, spiro five-membered ring peptide deformylase inhibitor.

BACKGROUND OF THE INVENTION

Antibiotics are a series of chemicals that can inhibit and kill pathogens at a certain concentration, including metabolites produced by microorganisms, animals and plants, and chemically synthetic or semi-synthetic compounds. Antibiotics not only refer to anti-bacterial substances, but also to anti-tumor, anti-viral, anti-parasitic substances and the like. Antibiotics are an important pillar that enables us to prolong life, live healthier and benefit from modern medicine.

With the large amount of antibiotics' emergence and widespread use thereof, the problem of antibiotic resistance has become increasingly prominent, and the speed of developing drug resistance has become faster and faster. The speed is fast and the spectrum of drug resistance is wide, which is staggering.

More than 95% of *Staphylococcus aureus* is resistant to almost all of penicillins and 90% methicillin worldwide. More than 80% of *E. coli* is not sensitive to one third of third-generation cephalosporins, and is resistant to 90% of fluoroquinolone. Not only that, many bacteria becomes to develop multiple drug resistance. In the clinic, *Staphylococcus aureus*, which is resistant to methicillin, is also resistant to amoxicillin, levofloxacin, rifampicin, and even vancomycin. *E. coli* and *K. pneumoniae* have formed new resistance mechanism, producing New Delhi metallo-β-lactamase 1 (NDM-1) which is resistant to almost all of β-lactam drugs.

Chemotherapy is currently one of the most important means of clinical treatment for malignant tumors. However, because tumor cells often become resistant to chemotherapeutic drugs, patients are no longer sensitive to chemotherapy, which ultimately leads to failure of treatment. Although the epidermal growth factor receptor (EGFR) inhibitors such as Iressa and Tarceva and the like have achieved great success in the treatment of non-small cell lung cancer, the drug resistance problem has become increasingly prominent, and half of the drug resistance is derived from the EGFR T790M mutation. Hepatocellular carcinoma is one of the most common malignant cancers in the world and is generally highly tolerant to chemotherapeutic drugs. Nearly half of breast cancers are resistant to Herceptin from the beginning.

In view of the increasingly severe situation of antibiotic resistance, developing antibiotics with new mechanisms of action is imminent. Peptide deformylase inhibitor is one of the new targets for research in recent years. Peptide deformylase (PDF) is a metalloproteinase which is not only widely found in bacteria but also in *Plasmodium falciparum* and humans. In the process of proteins synthesis in bacterial, PDF can remove formyl groups from methionine, allowing functionalized proteins synthesizd in bacteria. The process of removing formyl groups is a necessary process for proteins synthesis in bacteria. However, the main protein synthesis process in human cells does not depend on the process of formyl removal. This difference on protein synthesis between bacteria and human makes bacterial PDF a potential target for anti-bacterial drugs. By chelation with the PDF enzyme, PDF inhibitor could prevent bacteria from undergoing the deformylation step in the process of protein synthesis, thereby selectively inhibiting the growth of bacteria. Compared with normal human cells, human PDF gene in various of cancer cells such as colorectal cancer, lung cancer, prostate cancer and the like are over-expressed, which can affect the energy balance of the cancer cells by inhibiting the peptide deformylase in mitochondria in the cells, so that mitochondrial membrane can be depolarized, ATP can be exhausted and cell apoptosis can be promoted. PDF inhibitors can be developed into broad-spectrum anti-bacterial agents with good anti-bacterial activity and anti-cancer drugs with anti-cancer activity.

PDF inhibitors encompassed structures: Metal Binding Group (MBG) and peptidomimetic or non-peptide backbones containing P1, P2 and P3 moieties (formula (a): general structure for PDF inhibitor).

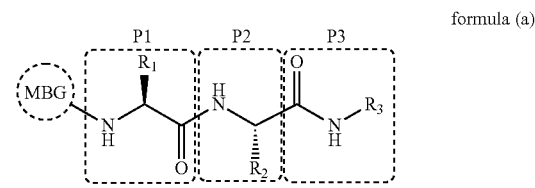

formula (a)

Although many PDF inhibitors have been developed for preclinical studies, and even some compounds have entered into the clinic (e.g. formulas (b)~(d)), due to the nature of the compounds themselves, they showed poor activity, or clinical toxicity, and ultimately could not successfully appear on the market. For example, actinomycin Actinonin is the first PDF inhibitor to be discovered that exhibits good activity against Gram-positive and Gram-negative bacteria; but due to instability in metabolism in the body, it ultimately exhibits no activity in vivo. For LBM415, entered into Phase I clinical trial of anti-bacterial activity, which has broad-spectrum activity, and could cause methemoglobinemia at a high dose (*Clin. Pharmacol. Ther.* 2011, 90, 256). For GSK1322322, due to the presence of metabolically active compounds which could cause toxicity to the body, the Phase I clinical study of anti-bacterial activity also had been terminated by FDA for similar reasons (see project No. NCT01818011 in ClinicalTrials.gov for reasons of clinical study termination).

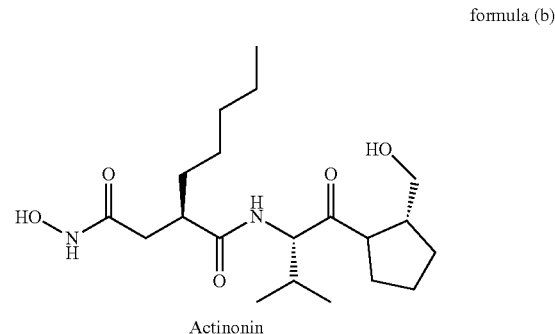

formula (b)

Actinonin

-continued

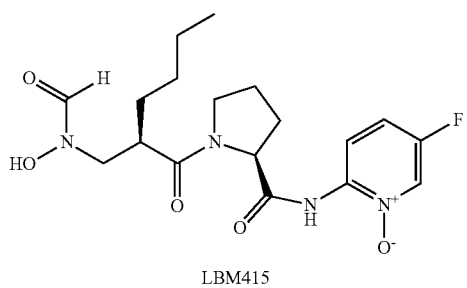

LBM415 formula (c)

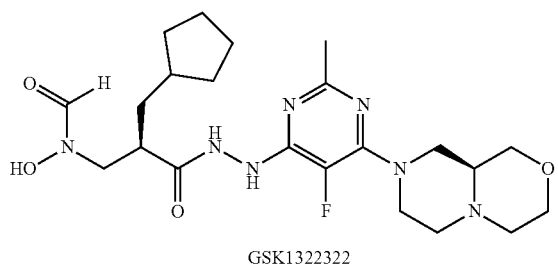

GSK1322322 formula (d)

SUMMARY OF THE INVENTION

The invention provides a series of spiro three-membered ring, spiro five-membered ring peptide deformylase inhibitor with novel structure, better activity, and low toxic, for inhibiting bacteria resistant to existing antibiotics, including Gram-positive bacteria, such as *Staphylococcus aureus, Staphylococcus epidermidis, Enterococcus faecalis, Enterococcus faecium, Streptococcus pneumoniae,* and Gram-negative bacteria that seriously affect human health, such as *Moraxella catarrhalis*, etc. The invention also discloses that the spiro three-membered ring, spiro five-membered ring peptide deformylase inhibitor can selectively inhibit the proliferation of cancer cells such as colorectal cancer, lung cancer, gastric cancer, and liver cancer, and the like.

The spiro three-membered ring, spiro five-membered ring peptide deformylase inhibitor of the present invention belongs to antibiotics and is represented by the following four structures as formulas (1) to (4):

Category I:

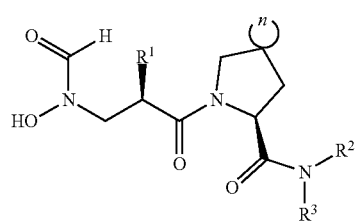

formula (1)

In the formula (1), n=2-4; $R^1$ is n-butyl or cyclopentylmethyl; $R^2$ is aromatic ring, aromatic heterocyclic ring, heterocyclic ring, or alkyl; and $R^3$ is hydrogen or alkyl.

Preferably, n=2 or 4; $R^1$ is n-butyl or cyclopentylmethyl; $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2-yl, 5-methylthiazol-2-yl, 3-(pyridin-3-yl)phenyl, N-(pyrimidin-2-yl)phenyl-1-amino-3-yl, 4-(pyridin-3-yl) pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, cyclopropyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, bisethylsulfonyl, benzothiazol-2-yl, 3-methyl formate-2-thienyl; and $R^3$ is hydrogen.

More preferably, the spiro three-membered ring, spiro five-membered ring peptide deformylase inhibitor is selected from the compounds of Examples 1-9, 14-23 and 25-41.

Category II:

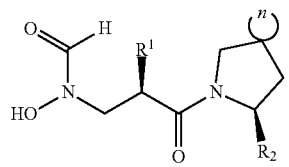

formula (2)

In the formula (2), n=2-4; $R^1$ is n-butyl or cyclopentylmethyl; $R^2$ is aromatic ring, or aromatic heterocyclic ring.

Preferably, n=2 or 4, $R^1$ is n-butyl or cyclopentylmethyl; $R^2$ is aromatic heterocyclic ring.

More preferably, n=2 or 4, $R^1$ is n-butyl or cyclopentylmethyl; and $R^2$ is 2-benzimidazolyl, 1,3,4-oxodioxazole, 1,2,4-oxodioxazole, or 1,3,4-triazole.

More preferably, the spiro three-membered ring, spiro five-membered ring peptide deformylase inhibitor is selected from the compounds in Examples 10-13, 24 and 42.

Category III:

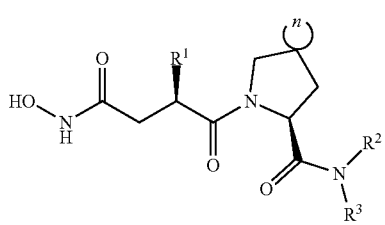

formula (3)

In the formula (3), n=2-4; $R^1$ is n-butyl or cyclopentylmethyl; $R^2$ is aromatic ring, aromatic heterocyclic ring, heterocyclic ring, or alkyl; and $R^3$ is hydrogen or alkyl.

Preferably, n=2 or 4; $R^1$ is n-butyl or cyclopentylmethyl; $R^2$ is aromatic heterocyclic ring; and $R^3$ is hydrogen.

Preferably, n=2 or 4; $R^1$ is n-butyl or cyclopentylmethyl; $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2-yl, 5-methylthiazol-2-yl, 3-(pyridin-3-yl)phenyl, N-(pyrimidin-2-yl)phenyl-1-amino-3-yl, 4-(pyridin-3-yl) pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, cyclopropyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, bisethylsulfonyl, benzothiazol-2-yl, 3-methyl formate-2-thienyl; and $R^3$ is hydrogen.

More preferably, the spiro three-membered ring, spiro five-membered ring peptide deformylase inhibitor is selected from the compounds in Examples 43-57, 61-74 and 77-80.

Category IV:

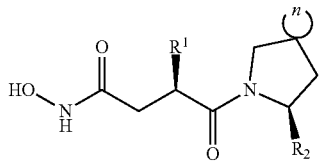

formula (4)

In the formula (4), n=2-4; $R^1$ is n-butyl or cyclopentylmethyl; and $R^2$ is aromatic ring, or aromatic heterocyclic ring.

Preferably, n=2 or 4; $R^1$ is n-butyl or cyclopentylmethyl; and $R^2$ is aromatic heterocyclic ring.

More preferably, n=2 or 4; $R^1$ is n-butyl or cyclopentylmethyl; and $R^2$ is 2-benzimidazolyl, 1,3,4-oxodioxazole, 1,2,4-oxodioxazole, 1,3,4-triazole.

More preferably, the spiro three-membered ring, spiro five-membered ring peptide deformylase inhibitor is selected from the compounds in Examples 58-60, 75 and 76.

The spiro three-membered ring, spiro five-membered ring peptide deformylase inhibitor represented by the formulas (1) to (4) in the present invention has a molecular weight of 300-600; is soluble in dichloromethane, acetone, acetonitrile, methanol, ethanol, N,N-dimethylformamide, dimethyl sulfoxide and the like; is slightly soluble in ether, water, etc.; is insoluble in petroleum ether; and is usually colorless or yellowish powder or foam.

The present invention also provides a use of the spiro three-membered ring, spiro five-membered ring peptide deformylase inhibitor represented by the formulas (1) to (4) for inhibiting bacterial peptide deformylase.

Wherein, the bacteria include *Staphylococcus aureus, Staphylococcus epidermidis, Enterococcus faecalis, Enterococcus faecium, Streptococcus pneumoniae,* and *Moraxella catarrhalis*.

In the present invention, screening anti-bacterial activity of 80 new synthesized compounds in vitro was performed on 46 clinically isolated strains (see Table 1 for strains), with levofloxacin and LBM415 as control (see Table 2 for the list of 80 compounds).

The present invention also provides a use of the spiro three-membered ring, spiro five-membered ring peptide deformylase inhibitor represented by the formulas (1) to (4) in preparation of anti-tumor drugs.

Wherein, the tumor refers to colorectal cancer, leukemia, lung cancer, gastric cancer, cervical cancer, breast cancer, prostate cancer, liver cancer, and osteosarcoma, and the like.

The invention adopts cck-8 method to determine the inhibition effect of the compounds on the proliferation of nine kinds of tumor cells such as colorectal cancer, leukemia, lung cancer, gastric cancer, cervical cancer, breast cancer, prostate cancer, liver cancer and osteosarcoma, and the like.

The present invention also provides a use of the spiro three-membered ring, spiro five-membered ring peptide deformylase inhibitor represented by the formulas (1) to (4) in preparation of anti-parasitic drugs.

Wherein, the anti-parasitic refers to that the spiro three-membered ring, spiro five-membered ring peptide deformylase inhibitor inhibits the growth of parasites by inhibiting peptide deformylase in parasites.

The present invention also provides a pharmaceutical composition comprising the spiro three-membered ring, spiro five-membered ring peptide deformylase inhibitor as described above, and a pharmaceutically acceptable carrier.

Wherein, the pharmaceutically acceptable carrier refers to conventional pharmaceutical carrier in the pharmaceutical field, such as diluent, excipient, water, etc., filler such as starch, sucrose, lactose, microcrystalline cellulose, etc.; adhesive such as cellulose derivatives, alginates, gelatin and polyvinylpyrrolidone; wetting agent such as glycerin; disintegrating agent such as sodium carboxymethyl starch, hydroxypropyl cellulose, croscarmellose, agar, calcium carbonate and sodium bicarbonate; absorption enhancer such as quaternary ammonium compounds; surfactants such as cetyl alcohol, sodium lauryl sulfate; adsorption carrier such as kaolin and bentonite; lubricant such as talc powder, calcium stearate and magnesium, micro-silica gel and polyethylene glycol. In addition, flavoring agents, sweeteners and the like can also be using as a carrier.

In the present invention, the administration modes of the inhibitor or the pharmaceutical composition include oral administration, injection, implantation, and the like.

In the present invention, the inhibitor or the pharmaceutical composition may be administered in the form of a tablet, liquid, or a capsule, and the like.

The new spiro three-membered ring and spiro five-membered ring peptide deformylase inhibitor of the present invention has anti-bacterial activity and anti-tumor activity. The mechanism of action of the spiro ring peptide deformylase inhibitor of the present invention is: selectively killing bacteria by inhibiting the activity of the peptide deformylase required in the synthesis of bacterial proteins, without affecting the synthetic process of main proteins in human body; affecting the energy balance of cancer cells through inhibiting the peptide deformylase in mitochondria in human cells, so that mitochondrial membrane can be depolarized, ATP can be exhausted and cell apoptosis can be promoted. The inhibitor of the present invention is less susceptible to drug resistance as commercially available antibiotics due to the novel mechanism of action. The peptide deformylase inhibitor can be used not only as a new type of anti-bacterial agent, which can be effective against a variety of antibiotic-resistant Gram-positive strains, such as *Staphylococcus aureus, Staphylococcus epidermidis, Enterococcus faecalis, Enterococcus, Streptococcus pneumoniae*; but also is effective against Gram-negative bacteria such as *Moraxella catarrhalis*. It can also be used as a newtype anti-cancer drug, which has inhibitory activity against various cancer cell strains such as colorectal cancer, lung cancer, gastric cancer and liver cancer at low micromolar.

Compared with the compounds recorded in prior art, the present invention has significant technical advantages:

(1) The spiro three-membered ring, spiro five-membered ring peptide deformylase inhibitor of the present invention were found by the methods of molecular docking studies and anti-bacterial activity screening experiments (see Table 3 for anti-bacterial activities of the 80 compounds). Through molecular docking studies, it was found that the additional hydrophobic interaction between the ligand for increasing activity and the target protein, that is, the inhibitor's spiro three-membered ring can form strong force with the arginine residue on the protein. This conclusion is supported by the experiments, for example, the minimum inhibitory concentration MIC of the compound in Example 2 against methicillin-resistant *Staphylococcus* (MRSA) is 0.125-0.25 μg/mL, which has been significantly improved by four times as compared with LBM415, the MIC of which is 0.5-1 μg/mL (see Table 8 in Control Experiment 1). It has been found through the experiments that the introduction of the spiro five-membered ring has a significant impact on increasing the activity of the spiro five-membered ring inhibitor, such as Example 77, Example 78, Example 79, etc.

(2) The present invention adopts the strategy of modification using aromatic amide, such that the activities of some modified compounds (e.g. Example 3, Example 4, Example 5, Example 6, Example 7, Example 8, Example 15, Example 16, Example 19. Example 21, Example 22, Example 23, Example 25, Example 26, Example 27, Example 28, Example 29, Example 30, Example 33, Example 38, etc) against the test strains had been substantially improved. For example, the minimum inhibitory concentration MIC against methicillin-resistant Staphylococcus (MRSA) was <0.008-0.06 μg/mL, which was far superior to the lead compound LBM415 (MIC=0.5-1 μg/mL) and the launched antibiotic drug levofloxacin (MIC=16>128 μg/mL). The application of the strategy of using azole compounds as the amide bioisostere not only keeps the activity of the compounds, but also makes the MIC of most of the compounds be 0.5-2 μg/mL, such as: Example 10, Example 11, Example 12, Example 13, Example 75, etc. The key is that the present invention increases the stability of the compounds and also reduces the metabolic toxicity of the compounds (see Table 9 in Control experiment 2).

(3) In vitro anti-bacterial experiments of the spiro three-membered ring, spiro five-membered ring peptide deformylase inhibitor showed that the inhibitor not only affects Gram-positive bacteria such as *Staphylococcus aureus*, *Staphylococcus epidermidis*, drug-resistant *Staphylococcus aureus*, drug-resistant *Staphylococcus epidermidis*, *Enterococcus faecalis*, *Enterococcus faecium*, *Streptococcus pneumoniae*, with the minimum inhibitory concentration be only <0.008 μg/mL, which is 60 times higher than the lead compound LBM415, such as Example 3, Example 4, Example 6, Example 33, Example 38, Example 64, Example 72, Example 73, etc.; but also showed excellent activity against Gram-negative bacteria such as *Moraxella catarrhalis* which seriously affects human health, with the minimum inhibitory concentration as low as 0.06 μg/mL, such as Example 22, Example 33, etc. (see Table 10 in Control Experiment 3).

(4) The spiro three-membered ring, spiro five-membered ring peptide deformylase inhibitor of the present invention can effectively inhibit the proliferation of various cancer cells at a concentration of 30 μM, such as colorectal cancer, lung cancer, gastric cancer and liver cancer, etc., highlighting the selective inhibition against digestive tract cancer cells (see Tables 4 and 5). Meanwhile, the spiro three-membered ring, spiro five-membered ring peptide deformylase inhibitor of the present invention can also effectively inhibit the proliferation of other various cancer cells such as: leukemia, cervical cancer, breast cancer, prostate cancer and osteosarcoma, etc., highlighting the selective inhibition on leukemia and osteosarcoma cells (see Tables 6 and 7).

PREFERRED EXAMPLES OF THE INVENTION

The invention will be further described in detail in conjunction with the following specific examples. The processes, conditions, experimental methods, and the like for carrying out the present invention are generally known in the art and common general knowledge except for the contents specifically mentioned below, and the present invention is not particularly limited.

Experimental Method

1. The invention adopts the two-fold agar dilution method recommended by the operating procedure of antimicrobial susceptibility testing set by American Clinical and Laboratory Standards Institute (CLSI) to determine the Minimum Inhibitory Concentration (MIC) of the test samples against the tested strains. Compared with the in vitro anti-bacterial activity of the control drug LBM415 and levofloxacin, the in vitro anti-bacterial activity of all of the synthesized compounds against forty-six clinical isolated Gram-positive pathogens and Gram-negative pathogens in the past three years were investigated.

TABLE 1

Tested clinical isolated strains screened by in vitro anti-bacterial activity

| Name of strains | Number of strains |
|---|---|
| methicillin-resistant *Staphylococcus aureus* (MRSA) | 4 |
| methicillin-sensitive *Staphylococcus aureus* (MSSA) | 4 |
| methicillin-resistant *Staphylococcus epidermidis* (MRSE) | 4 |
| methicillin-sensitive *Staphylococcus epidermidis* (MSSE) | 4 |
| *Escherichia coli* (including ESBLs, non-ESBLs) | 8 |
| *Enterococcus faecalis* (EFA) | 7 |
| *Enterococcus faecium* (EFM) | 6 |
| *Streptococcus pneoumoniae* (SPN) | 2 |
| *Moraxella catarrhalis* (BCA) | 7 |

46 strains of bacteria in total

2. The present invention adopts the CCK-8 method to determine the proliferation inhibition effect of the spiro three-membered ring, spiro five-membered ring peptide deformylase inhibitor as described in Examples 1-80 against colorectal cancer cells, lung cancer cells, gastric cancer cells, liver cancer cells, and the like. Firstly, the anti-proliferation activity of 80 compounds against colorectal cancer cells was tested, and then 30 compounds with good anti-proliferation activity against colorectal cancer cells were selected, the inhibitory activity of which against four kinds of tumor cells such as colorectal cancer cells, lung cancer cells, gastric cancer cells and liver cancer cells were examined (see Table 5), wherein, the half effect inhibitory concentration (IC50) of 6 compounds with better activity was further determined (see Table 6). The compound having the best activity synthesized in Example 64 was further tested for its inhibitory activity against other tumor cells including T cell leukemia, acute myeloid leukemia, cervical cancer, breast cancer, prostate cancer and osteosarcoma, and the like (see Table 7).

(1) HCT-116 colorectal cancer cell line, A549 lung cancer cell line, MGC-803 gastric cancer cell line, BEL-7402 liver cancer cell line, Jurkat T cell leukemia cell line, HL60 acute myeloid leukemia cell line, Hela cervical cancer cell line, MCF-7 breast cancer cell line, PC3 prostate cancer cell line and SAOS-2 osteosarcoma cell line were made into single cell suspension, 180 μL of which was inoculated into 96-well culture plate, which was cultured overnight in $CO_2$ incubator (37° C., 5% $CO_2$, 95% air).

(2) Each of the spiro three-membered ring, spiro five membered ring peptide deformylase inhibitors was dissolved in DMSO, and was further formulated into drug solution with required different final concentration using corresponding cell culture medium. The drug solutions were added to the above cells respectively (20 μL/well), with the control group added with 1‰ DMSO, and cultured in a $CO_2$ incubator for 72 hours.

(3) After incubation for 72 hours, the culture solution was decanted, and 100 μL of 1:10 diluted CCK-8 solution was added. After incubation at 37° C. for 2 hours, the absorbance A at 450 nm was measured using a microplate reader SpectraMax M5, with the reference wavelength as 620 nm, and the inhibition rates on the growth of tumor cells were calculated.

Wherein, in step (1), the concentration of the single cell suspension was 2000 cells/well.

Wherein, in step (2), HCT-116 cells were cultured in McCoy's 5A medium (containing 10% newborn bovine serum, 1% double antibody); A549 and PC3 cells were cultured in F12 medium (containing 10% newborn bovine serum, 1% double antibody); MGC-803, BEL-7402, SAOS-2, Jurkat and HL60 cells were cultured in 1640 medium (containing 10% newborn bovine serum, 1% double antibody); and MCF-7 and Hela cells were cultured in DMEM high glucose medium (containing 10% newborn bovine serum, 1% double antibody).

In the step (2), the formula of the inhibition rate is $1-(A_{drug\ treatment\ group}-A_{control\ group})/(A_{drug-free\ treatment\ group}-A_{control\ group})$, wherein, A is absorbance.

In the step (2), when IC50 values were determined, the compounds were respectively formulated into 30 μM, 10 μM, 3.3 μM, 1.1 μM, 0.37 μM, 0.12 μM, 0.04 μM, and 0.013 μM, and added to the cells. After 72 hours, the absorbances were measured as in the step (3), and the inhibition rates of the compounds with different concentrations on the tumor cells growth were calculated. The data were analyzed by GraphPad Prism 5, and IC50 values (IC50 value refers to the concentration of the corresponding compound when the inhibition rate reaches 50%) were calculated.

Method for Preparing Compounds

General Formula (X1) of Amino Compounds

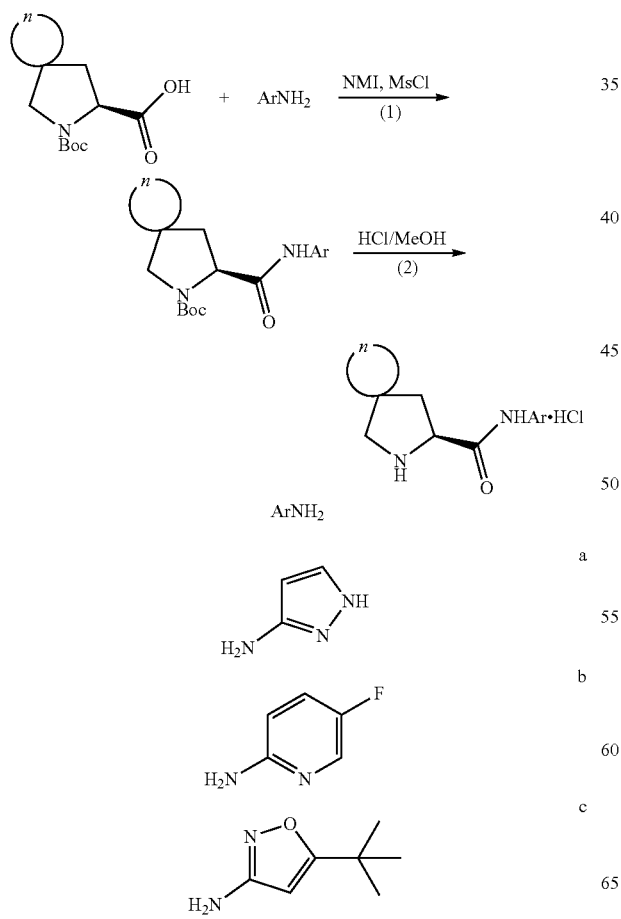

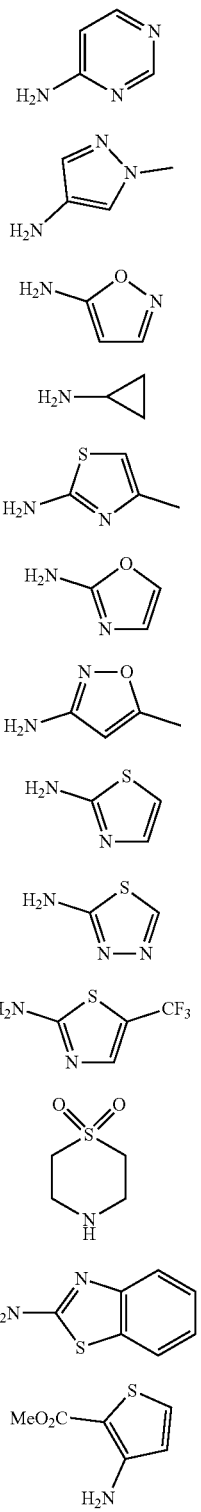

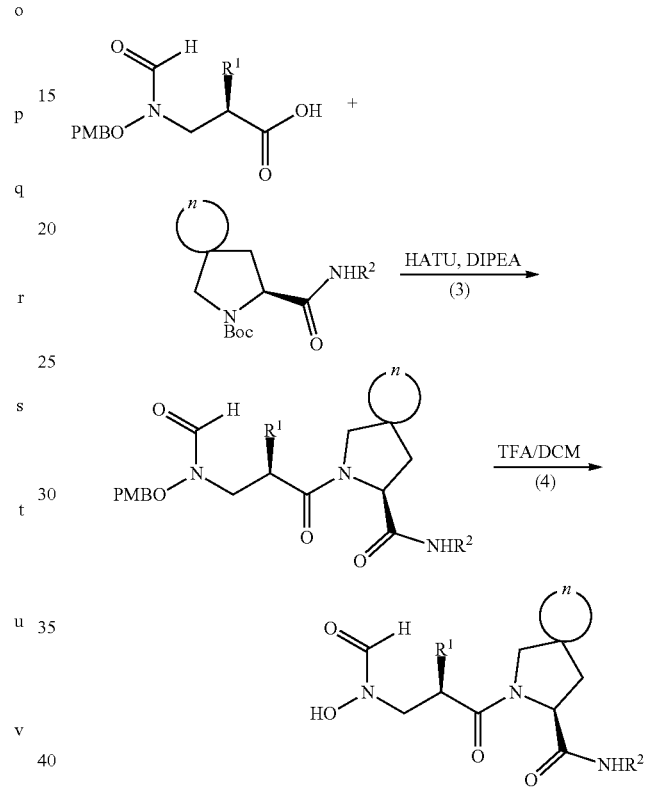

was extracted twice with 50 mL of EA. The combined organic phase was washed successively with saturated sodium bicarbonate and saturated sodium chloride. The organic phase was concentrated to gibe the product.

Step 2: A solution of HCl/MeOH was added to the product obtained in the above step (1). After completion of the reaction, the product was obtained.

General Formula (X2) of Final Compound

Hydroxamic Acid Series:

Wherein n=2 or 4; $R^1$ is n-butyl or cyclopentylmethyl; $R^2$ is aromatic ring, aromatic heterocyclic ring, heterocyclic ring, or alkyl group.

Preferably, n=2 or 4; $R^1$ is n-butyl or cyclopentylmethyl; $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2-yl, 5-methylthiazol-2-yl, 3-(pyridin-3-yl)phenyl, N-(pyrimidin-2-yl)phenyl-1-amino-3-yl, 4-(pyridin-3-yl)pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, cyclopropyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, bisethylsulfonyl, benzothiazol-2-yl, 3-methyl formate-2-thienyl.

Step 1: To an acid, DMF was added, then 2.1 equivalents of N-methylimidazole was added under ice bath, and then 1 equivalent of MsCl was slowly added. After stirring for 15 min, 1 equivalent of Boc-protected amine was added to the mixture. The reaction was monitored by TLC. After completion of the reaction, the reaction mixture was diluted with EA, and washed with 10% citric acid; and the aqueous phase

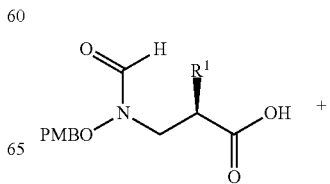

-continued

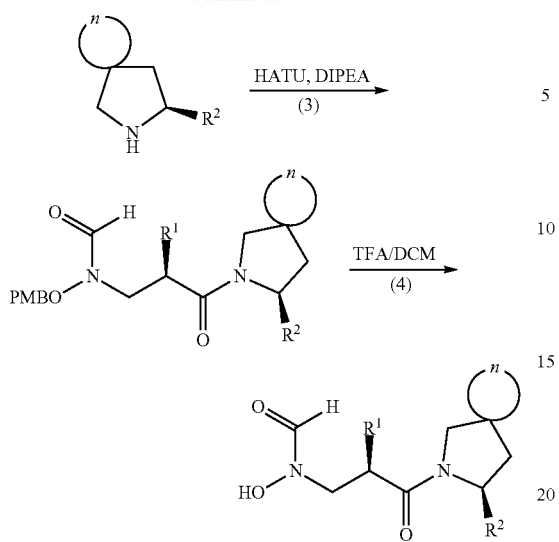

Wherein, n=2 or 4, $R^1$ is n-butyl or cyclopentylmethyl; and $R^2$ is aromatic ring, or aromatic heterocyclic ring.

Preferably, n=2 or 4; $R^1$ is n-butyl or cyclopentylmethyl; and $R^2$ is 2-benzimidazolyl, 1,3,4-oxodioxazole, 1,2,4-oxodioxazole or 1,3,4-triazole.

Step 3: To DMF, acid was dissolved, and then 5 equivalents of DIPEA and condensing agent HATU (1.05 equivalents) were added successively under ice bath. After stirrring for 15 min, synthesized amine (1.0 equivalents) was added to the mixture. After completion of the reaction, the reaction solution was diluted with ethyl acetate, and washed twice with 10% citric acid aqueous solution; and the aqueous phase was extracted twice with ethyl acetate. The combined organic phase was washed with saturated sodium bicarbonate and saturated sodium chloride, and dried over anhydrous sodium sulfate, filtered, and concentrated to give a crude product, which was directly used in the next step.

Step 4: To dichloromethane (2 mL) the crude product was dissolved, and trifluoroacetic acid (1 mL) was added dropwise. After the reaction mixture was stirred at room temperature for 2 hours, it was neutralized with saturated sodium carbonate aqueous solution, and the organic phase was separated out. The aqueous phase was extracted once with methylene chloride. The combined organic phase was dried over anhydrous sodium sulfate, followed by rotary evaporation for drying to give a crude product.

Hydroxamic Acid Series:

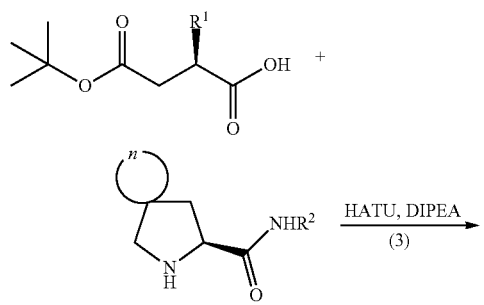

-continued

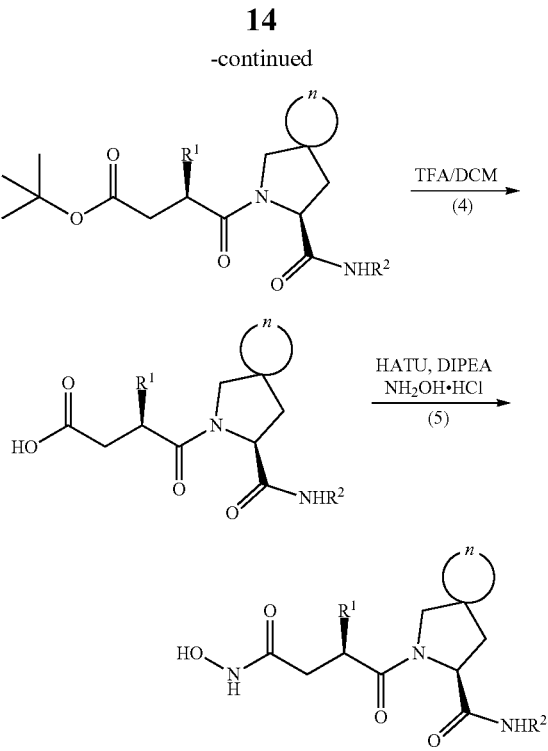

Wherein n=2 or 4; $R^1$ is n-butyl or cyclopentylmethyl; and $R^2$ is selected from aromatic ring, aromatic heterocyclic ring, heterocyclic ring, or alkyl group.

Preferably, n=2 or 4; $R^1$ is n-butyl or cyclopentylmethyl; $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2-yl, 5-methylthiazol-2-yl, 3-(pyridin-3-yl)phenyl, N-(pyrimidin-2-yl)phenyl-1-amino-3-yl, 4-(pyridin-3-yl)pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, cyclopropyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, bisethylsulfonyl, benzothiazol-2-yl, 3-methyl formate-2-thienyl.

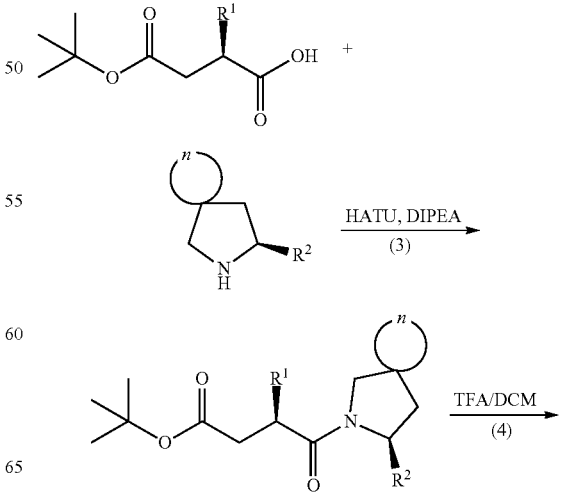

15 -continued

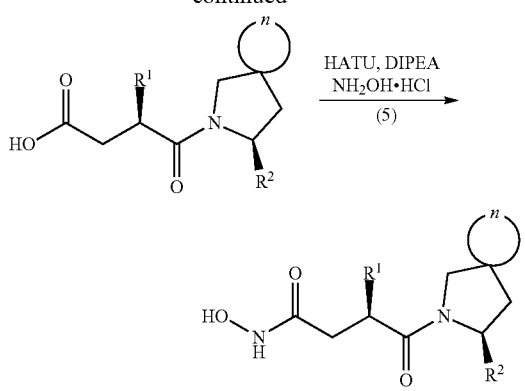

Wherein n=2 or 4; $R^1$ is n-butyl or cyclopentylmethyl; $R^2$ is aromatic ring or aromatic heterocyclic ring.

Preferably, n=2 or 4; $R^1$ is n-butyl or cyclopentylmethyl; and $R^2$ is 2-benzimidazolyl, 1,3,4-oxodioxazole, 1,2,4-oxodioxazole, or 1,3,4-triazole.

Step 3: was the same as the step 3 for the hydroxamic acid series.

Step 4: was the same as the step 4 for the hydroxamic acid series.

Step 5: To DMF, the acid obtained in the previous step was dissolved, and 5 equivalents of DIPEA and condensing agent HATU (1.05 equivalents) were added successively under ice bath. After the mixture was stirred for 15 min, 3-fold of hydroxylamine hydrochloride was added. After completion of the reaction, the final product was obtained through HPLC purification.

TABLE 2

List of final synthesized compounds

| Example | Structure of the compound | Molecular Weight |
|---|---|---|
| 1 | | 377.45 |
| 2 | | 422.46 |
| 3 | | 434.54 |
| 4 | | 571.68 |

TABLE 2-continued

List of final synthesized compounds

| Example | Structure of the compound | Molecular Weight |
|---------|---------------------------|------------------|
| 5 | | 405.47 |
| 6 | | 408.52 |
| 7 | | 464.57 |
| 8 | | 480.57 |
| 9 | | 466.54 |

TABLE 2-continued

List of final synthesized compounds

| Example | Structure of the compound | Molecular Weight |
|---------|---------------------------|------------------|
| 10 | | 384.48 |
| 11 | | 413.48 |
| 12 | | 413.48 |
| 13 | | 385.47 |

TABLE 2-continued

List of final synthesized compounds

| Example | Structure of the compound | Molecular Weight |
|---|---|---|
| 14 | | 472.59 |
| 15 | | 389.46 |
| 16 | | 389.46 |
| 17 | | 378.43 |
| 18 | | 351.45 |
| 19 | | 408.52 |

TABLE 2-continued
List of final synthesized compounds
| Example | Structure of the compound | Molecular Weight |
|---------|---------------------------|------------------|
| 20 | 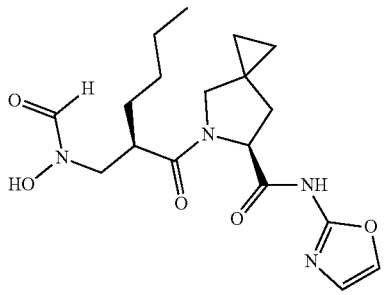 [SMILES: CCCC[C@H](CN(O)C=O)C(=O)N1CC2(CC2)C[C@H]1C(=O)Nc1ncco1] | 378.43 |
| 21 | 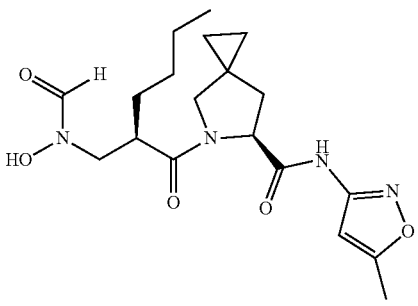 [SMILES: CCCC[C@H](CN(O)C=O)C(=O)N1CC2(CC2)C[C@H]1C(=O)Nc1cc(C)on1] | 392.46 |
| 22 | 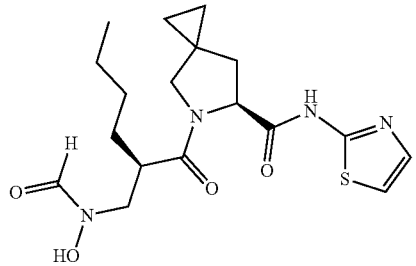 [SMILES: CCCC[C@H](CN(O)C=O)C(=O)N1CC2(CC2)C[C@H]1C(=O)Nc1nccs1] | 394.49 |
| 23 | 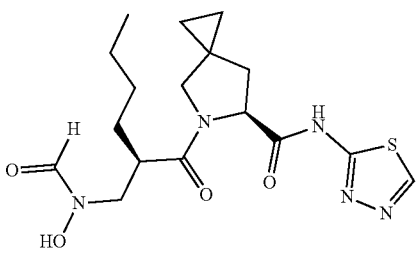 [SMILES: CCCC[C@H](CN(O)C=O)C(=O)N1CC2(CC2)C[C@H]1C(=O)Nc1nncs1] | 395.48 |
| 24 | 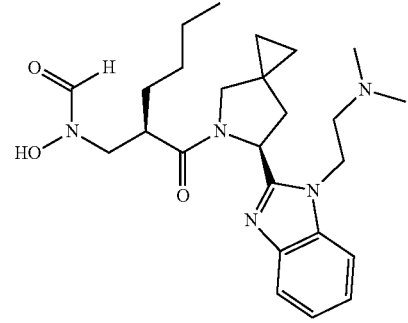 [SMILES: CCCC[C@H](CN(O)C=O)C(=O)N1CC2(CC2)C[C@H]1c1nc2ccccc2n1CCN(C)C] | 455.60 |

TABLE 2-continued

List of final synthesized compounds

| Example | Structure of the compound | Molecular Weight |
|---------|---------------------------|------------------|
| 25 | | 498.62 |
| 26 | | 415.49 |
| 27 | | 415.49 |
| 28 | | 433.50 |
| 29 | | 434.56 |
| 30 | | 432.50 |

TABLE 2-continued

List of final synthesized compounds

| Example | Structure of the compound | Molecular Weight |
|---|---|---|
| 31 | | 403.48 |
| 32 | | 377.49 |
| 33 | | 434.56 |
| 34 | | 477.58 |
| 35 | | 455.57 |

TABLE 2-continued

List of final synthesized compounds

| Example | Structure of the compound | Molecular Weight |
|---------|---------------------------|------------------|
| 36 | | 404.47 |
| 37 | | 404.47 |
| 38 | | 460.58 |
| 39 | | 418.49 |
| 40 | | 420.53 |

TABLE 2-continued

List of final synthesized compounds

| Example | Structure of the compound | Molecular Weight |
|---|---|---|
| 41 | | 421.52 |
| 42 | | 410.52 |
| 43 | | 513.7 |
| 44 | | 389.46 |
| 45 | | 389.46 |

TABLE 2-continued

List of final synthesized compounds

| Example | Structure of the compound | Molecular Weight |
|---|---|---|
| 46 | | 406.46 |
| 47 | | 408.52 |
| 48 | | 389.46 |
| 49 | | 406.46 |
| 50 | | 351.45 |

TABLE 2-continued

List of final synthesized compounds

| Example | Structure of the compound | Molecular Weight |
|---|---|---|
| 51 | | 408.52 |
| 52 | | 448.57 |
| 53 | | 378.43 |
| 54 | | 378.43 |
| 55 | | 434.54 |

TABLE 2-continued

List of final synthesized compounds

| Example | Structure of the compound | Molecular Weight |
|---------|---------------------------|------------------|
| 56 | | 392.46 |
| 57 | | 462.49 |
| 58 | | 384.48 |
| 59 | | 384.48 |
| 60 | | 455.60 |

TABLE 2-continued

List of final synthesized compounds

| Example | Structure of the compound | Molecular Weight |
|---|---|---|
| 61 | | 498.62 |
| 62 | | 415.49 |
| 63 | | 415.49 |
| 64 | | 432.50 |
| 65 | | 434.56 |

TABLE 2-continued

List of final synthesized compounds

| Example | Structure of the compound | Molecular Weight |
|---------|---------------------------|------------------|
| 66 | | 415.49 |
| 67 | | 432.50 |
| 68 | | 377.49 |
| 69 | | 404.47 |
| 70 | | 404.47 |

TABLE 2-continued

List of final synthesized compounds

| Example | Structure of the compound | Molecular Weight |
|---|---|---|
| 71 | | 418.49 |
| 72 | | 420.53 |
| 73 | | 488.53 |
| 74 | | 421.52 |
| 75 | | 410.52 |

TABLE 2-continued

List of final synthesized compounds

| Example | Structure of the compound | Molecular Weight |
|---|---|---|
| 76 | | 410.52 |
| 77 | | 417.51 |
| 78 | | 434.51 |
| 79 | | 436.57 |
| 80 | | 420.51 |

TABLE 3

Anti-bacterial activities of the compounds

| Strain | Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| MRSA 14-1 | 16 | 0.25 | 0.06 | 0.015 | 0.5 | <0.008 | 0.125 | 0.25 | 2 | 1 | 0.5 | 4 | 1 |
| MRSA 14-2 | 32 | 0.25 | 0.06 | 0.015 | 0.5 | <0.008 | 0.125 | 0.25 | 0.5 | 2 | 0.5 | 4 | 1 |
| MRSA 14-3 | 16 | 0.125 | <0.008 | <0.008 | 0.5 | <0.008 | 0.125 | 0.25 | 2 | 2 | 0.5 | 4 | 1 |
| MRSA 14-4 | 8 | 0.125 | 0.06 | <0.008 | 0.25 | <0.008 | 0.125 | 0.125 | 0.25 | 0.5 | 0.5 | 2 | 1 |
| MRSA 14-5 | 16 | 0.125 | 0.125 | 0.015 | 0.5 | <0.008 | 0.125 | 0.25 | 0.25 | 2 | 0.5 | 4 | 1 |
| MSSA 14-1 | 16 | 0.125 | 0.125 | 0.015 | 0.5 | <0.008 | 0.125 | 0.25 | 0.5 | 2 | 0.5 | 2 | 1 |
| MSSA 14-2 | 16 | 0.125 | 0.25 | 0.015 | 0.5 | <0.008 | 0.125 | 0.25 | 0.5 | 2 | 0.5 | 2 | 1 |
| MSSA 14-3 | 16 | 0.125 | 0.06 | 0.015 | 0.5 | <0.008 | 0.125 | 0.125 | 0.25 | 2 | 0.5 | 2 | 1 |
| MSSA 14-4 | 16 | 0.03 | 0.03 | <0.008 | 0.25 | <0.008 | 0.06 | 0.125 | 0.25 | 1 | 0.25 | 1 | 0.5 |
| MRSA 14-1 | 8 | 0.06 | 0.03 | <0.008 | 0.25 | <0.008 | 0.06 | 0.25 | 0.125 | 0.5 | 0.25 | 0.5 | 0.5 |
| MRSE 14-2 | 8 | 0.06 | 0.015 | <0.008 | 0.125 | <0.008 | 0.06 | 0.06 | 0.125 | 1 | 0.125 | 0.5 | 0.25 |
| MRSE 14-3 | 4 | 0.125 | 0.03 | <0.008 | 0.5 | <0.008 | 0.125 | 0.25 | 0.5 | 0.5 | 0.5 | 4 | 1 |
| MRSE 14-4 | 8 | 0.03 | 0.03 | 0.015 | 0.125 | <0.008 | 0.06 | 0.125 | 0.125 | 0.5 | 0.125 | 1 | 0.25 |
| MSSE 14-1 | 4 | 0.125 | 0.125 | <0.008 | 0.25 | <0.008 | 0.125 | 0.25 | 0.5 | 2 | 0.5 | 1 | 0.5 |
| MSSE 14-2 | 16 | 0.03 | 0.015 | <0.008 | 0.25 | <0.008 | 0.06 | 0.125 | 0.25 | 0.5 | 0.125 | 0.5 | 0.5 |
| MSSE 14-3 | 4 | 0.03 | 0.015 | 0.015 | 0.25 | <0.008 | 0.125 | 0.25 | 0.5 | 2 | 0.5 | 1 | 0.5 |
| MSSE 14-4 | 4 | 0.03 | 0.015 | 0.015 | 0.25 | <0.008 | 0.125 | 0.25 | 0.5 | 2 | 0.5 | 1 | 0.5 |
| ECO⁻ 14-1 | >128 | 128 | 64 | >128 | >64 | 32 | 32 | 128 | >64 | 32 | 64 | 128 | 128 |
| ECO⁻ 14-2 | >128 | 64 | 64 | >128 | 64 | 32 | 32 | 128 | >64 | 32 | 64 | 64 | 128 |
| ECO⁺ 14-1 | 16 | 1 | 1 | 4 | 2 | 0.125 | 0.5 | 1 | 2 | 0.5 | 1 | 0.5 | 2 |
| ECO⁺ 14-2 | 128 | 64 | 64 | >128 | 64 | 32 | 32 | 64 | >64 | 32 | 32 | 64 | 128 |
| EFA 14-1 | 64 | 0.25 | 0.5 | 0.03 | 2 | 0.125 | 0.25 | 0.5 | 0.5 | 8 | 2 | 4 | 4 |
| EFA 14-2 | 64 | 0.5 | 0.5 | 0.015 | 2 | 0.5 | 0.25 | 1 | 0.5 | 8 | 2 | 8 | 8 |

TABLE 3-continued

Anti-bacterial activities of the compounds

| Strain | \multicolumn{13}{c}{Example} |
| | 14 | 15 | 16 | 17 | 18 | 19 | 20 | 21 | 22 | 23 | 24 | 25 | 26 |
|---|---|---|---|---|---|---|---|---|---|---|---|---|---|
| EFA 14-3 | 64 | 0.5 | 0.5 | 0.03 | 2 | 0.5 | 0.25 | 1 | 1 | 8 | 2 | 8 | 8 |
| EFA 14-5 | >128 | 128 | >128 | >128 | 2 | 0.25 | 0.5 | 1 | 0.5 | 64 | 2 | 8 | 8 |
| MRSA 15-1 | 1 | 0.125 | 0.06 | 1 | 2 | 0.125 | 32 | 0.25 | 0.06 | 0.25 | 8 | 0.25 | 0.25 |
| MRSA 15-2 | 1 | 0.25 | 0.25 | 1 | 2 | 0.125 | 32 | 0.5 | 0.25 | 2 | 32 | 0.25 | 0.25 |
| MRSA 15-3 | 1 | 0.125 | 0.25 | 1 | 2 | 0.03 | 32 | 0.5 | 0.06 | 0.25 | 32 | 0.25 | 0.25 |
| MRSA 15-4 | 1 | 0.25 | 1 | 1 | 2 | 0.25 | 32 | 0.5 | 0.25 | 2 | 8 | 0.25 | 0.25 |
| MSSA 15-3 | 1 | 0.25 | 1 | 1 | 2 | 0.125 | 8 | 0.5 | 0.06 | 1 | 8 | 0.25 | 0.25 |
| MSSA 15-4 | 1 | 0.125 | 0.25 | 1 | 2 | 0.125 | 4 | 0.25 | 0.06 | 1 | 8 | 0.25 | 0.25 |
| MSSA 15-5 | 0.25 | 0.125 | 0.125 | 0.25 | 2 | 0.03 | 4 | 0.25 | 0.03 | 0.25 | 8 | 0.25 | 0.25 |
| MSSA 15-6 | 1 | 0.125 | 1 | 1 | 2 | 0.25 | 4 | 0.5 | 0.06 | 0.25 | 8 | 0.25 | 0.25 |
| MRSE 15-1 | 0.25 | 0.125 | 0.06 | 0.25 | 2 | 0.06 | 4 | 0.25 | 0.03 | 0.25 | 8 | 0.06 | 0.125 |
| MRSE 15-2 | 0.25 | 0.25 | 1 | 0.5 | 2 | 0.125 | 4 | 0.25 | 0.06 | 0.25 | 8 | 0.25 | 0.5 |
| MRSE 15-3 | 1 | 0.25 | 0.25 | 0.5 | 2 | 0.125 | 4 | 0.25 | 0.125 | 0.25 | 8 | 0.25 | 0.5 |
| MRSE 15-7 | 1 | 0.25 | 0.25 | 1 | 2 | 0.125 | 4 | 0.25 | 0.125 | 1 | 8 | 0.25 | 0.5 |
| MSSE 15-3 | 0.25 | 0.25 | 1 | 1 | 2 | 0.125 | 8 | 0.5 | 0.06 | 0.25 | 8 | 0.25 | 0.125 |
| MSSE 15-4 | 0.25 | 0.06 | 0.06 | 0.5 | 2 | 0.125 | 8 | 0.25 | 0.03 | 0.25 | 2 | 0.25 | 0.5 |
| MSSE 15-5 | 0.25 | 0.06 | 0.06 | 0.5 | 2 | 0.03 | 4 | 0.03 | 0.03 | 0.25 | 2 | 0.25 | 0.5 |
| MSSE 15-6 | 0.125 | 0.06 | 0.06 | 0.25 | 2 | 0.015 | 4 | 0.03 | 0.03 | 0.25 | 8 | 0.25 | 0.5 |
| ECO+ 15-1 | >32 | 32 | 32 | 32 | 32 | 32 | >32 | 32 | 16 | >32 | 8 | 32 | 32 |
| ECO+ 15-2 | >32 | 64 | >32 | 32 | 32 | >32 | >32 | 32 | 64 | >32 | 16 | >32 | 32 |
| ECO+ 15-3 | >32 | 32 | >32 | >32 | 32 | >32 | >32 | 64 | 32 | >32 | 16 | >32 | 32 |
| ECO+ 15-4 | >32 | 32 | >32 | >32 | 32 | >32 | >32 | 64 | 32 | >32 | 16 | >32 | 32 |
| ECO− 15-1 | >32 | 32 | 32 | 16 | >32 | >32 | >32 | 64 | 32 | >32 | 8 | >32 | 32 |

TABLE 3-continued

Anti-bacterial activities of the compounds

| | | | | | | | | | | |
|---|---|---|---|---|---|---|---|---|---|---|
| ECO-15-2 | >32 | 64 | >32 | 32 | >32 | >32 | 64 | 64 | >32 | 32 |
| ECO-15-3 | >32 | 64 | >32 | >32 | 32 | >32 | 64 | 64 | >32 | 32 |
| ECO-15-4 | >32 | 64 | >32 | 32 | >32 | >32 | 64 | 64 | >32 | 32 |
| EFA 15-1 | 8 | 1 | 4 | 8 | 32 | 8 | 2 | 16 | 2 | 2 |
| EFA 15-2 | 8 | 1 | 4 | 8 | 32 | 8 | 2 | 16 | 2 | 2 |
| EFA 15-3 | 2 | 1 | 0.25 | 2 | 8 | 8 | 1 | 1 | 0.5 | 0.5 |
| EFA 15-4 | 8 | 1 | 4 | 8 | 32 | 8 | 2 | 32 | 2 | 2 |
| EFA 15-5 | 8 | 4 | 4 | 8 | 32 | 8 | 2 | 32 | 2 | 2 |
| EFA 15-6 | 8 | 4 | 4 | 8 | 32 | 8 | 2 | 32 | 2 | 2 |
| EFA 15-9 | 8 | 1 | 4 | 8 | 32 | 8 | 2 | 32 | 2 | 2 |
| EFM 15-1 | 1 | 1 | 0.5 | 1 | 8 | 8 | 0.5 | 1 | 4 | 1 | 0.5 |
| EFM 15-2 | 2 | 1 | 1 | 2 | 8 | 4 | 1 | 2 | 8 | 0.5 | 0.5 |
| EFM 15-3 | 0.5 | 0.125 | 0.25 | 0.5 | 2 | 0.25 | 4 | 0.5 | 0.5 | 2 | 0.25 |
| EFM 15-4 | 4 | 1 | 2 | 2 | 8 | 2 | 16 | 1 | 8 | 0.25 | 0.5 |
| EFM 15-5 | 0.5 | 0.125 | 0.25 | 1 | 4 | 0.25 | 4 | 0.5 | 4 | 0.5 | 0.25 |
| EFM 15-6 | 2 | 1 | 1 | 2 | 8 | 2 | 16 | 2 | 8 | 1 | 0.5 |
| SPN 16-2 | 8 | 0.015 | 4 | 8 | 16 | 4 | 4 | 2 | 15 | 0.5 | 0.25 |
| SPN 16-4 | 0.5 | 0.5 | 0.25 | 1 | 4 | 0.25 | 0.5 | 0.5 | 1 | 1 | 2 |
| BCA 14-1 | 4 | 0.5 | 0.5 | 4 | 16 | 1 | 16 | 0.5 | 8 | 2 | 0.5 |
| BCA 14-4 | 2 | 0.5 | 1 | 2 | 8 | 1 | 16 | 0.5 | 32 | 0.5 | 0.5 |
| BCA 14-5 | 2 | 0.125 | 0.25 | 1 | 4 | 0.125 | 4 | 0.25 | 16 | 0.25 | 0.25 |
| BCA 14-6 | 2 | 1 | 1 | 2 | 16 | 0.5 | 16 | 0.06 | 8 | 0.5 | 0.5 |
| BCA 14-7 | 1 | 0.125 | 0.25 | 1 | 4 | 0.25 | 8 | 0.06 | 32 | 1 | 0.5 |
| BCA 14-8 | 2 | 0.5 | 0.25 | 2 | 4 | 0.25 | 8 | 0.125 | 2 | 2 | 0.25 |
| BCA 14-10 | 0.5 | 0.125 | 0.25 | 1 | 4 | 0.125 | 4 | 0.5 | 0.5 | 1 | 0.25 | 0.25 |

TABLE 3-continued

Anti-bacterial activities of the compounds

| Strain | Example | | | | | | | | | | | | |
|---|---|---|---|---|---|---|---|---|---|---|---|---|---|
| | 27 | 28 | 29 | 30 | 31 | 32 | 33 | 34 | 35 | 36 | 37 | 38 | 39 |
| MRSA 15-1 | 0.125 | 0.125 | 0.125 | 0.5 | 2 | 1 | 0.03 | 1 | 16 | 4 | 0.5 | 0.125 | 1 |
| MRSA 15-2 | 0.125 | 0.125 | 0.125 | 0.5 | 2 | 1 | 0.06 | 1 | 32 | 8 | 1 | 0.125 | 1 |
| MRSA 15-3 | 0.125 | 0.125 | 0.06 | 0.5 | 2 | 1 | <0.008 | 1 | 16 | 4 | 0.5 | 0.125 | 1 |
| MRSA 15-4 | 0.125 | 0.125 | 0.125 | 0.5 | 2 | 1 | 0.06 | 0.5 | 32 | 8 | 0.2 | 0.25 | 1 |
| MSSA 15-3 | 0.125 | 0.125 | 0.125 | 0.5 | 2 | 2 | 0.06 | 1 | 32 | 8 | 1 | 0.25 | 1 |
| MSSA 15-4 | 0.125 | 0.125 | 0.125 | 0.5 | 2 | 1 | 0.03 | 1 | 32 | 8 | 1 | 0.25 | 1 |
| MSSA 15-5 | 0.125 | 0.125 | 0.125 | 0.5 | 2 | 2 | 0.03 | 1 | 32 | 4 | 0.5 | 0.125 | 1 |
| MSSA 15-6 | 0.06 | 0.125 | 0.06 | 0.5 | 0.5 | 1 | 0.06 | 1 | 16 | 4 | 1 | 0.125 | 1 |
| MRSE 15-1 | 0.125 | 0.5 | 0.125 | 2 | 2 | 2 | 0.015 | 0.25 | 32 | 8 | 0.5 | 0.25 | 1 |
| MRSE 15-2 | 0.125 | 0.5 | 0.125 | 2 | 2 | 8 | 0.125 | 4 | 32 | 8 | 1 | 0.25 | 1 |
| MRSE 15-3 | 0.125 | 0.5 | 0.125 | 2 | 2 | 8 | 0.125 | 4 | 32 | 8 | 1 | 0.25 | 1 |
| MRSE 15-7 | 0.125 | 0.125 | 0.125 | 2 | 2 | 2 | 0.125 | 4 | 32 | 8 | 1 | 0.25 | 1 |
| MSSE 15-3 | 0.125 | 0.125 | 0.125 | 2 | 2 | 2 | 0.125 | 4 | 32 | 8 | 1 | 0.25 | 1 |
| MSSE 15-4 | 0.125 | 0.125 | 0.125 | 2 | 2 | 2 | 0.125 | 4 | 32 | 8 | 1 | 0.25 | 1 |
| MSSE 15-5 | 0.125 | 0.125 | 0.125 | 0.5 | 2 | 2 | 0.125 | 1 | 32 | 8 | 1 | 0.25 | 1 |
| MSSE 15-6 | 0.125 | 0.06 | 0.06 | 0.5 | 2 | 2 | 0.03 | 1 | 32 | 8 | 1 | <0.008 | 1 |
| ECO+ 15-1 | 16 | 16 | 16 | 32 | 32 | 32 | >32 | 128 | 32 | 8 | 32 | 16 | 16 |
| ECO+ 15-2 | 32 | 64 | 32 | >32 | >32 | >32 | >32 | 128 | >32 | >32 | 32 | 32 | 32 |
| ECO+ 15-3 | 32 | 64 | 16 | >32 | >32 | >32 | >32 | 128 | >32 | >32 | 32 | 16 | 16 |
| ECO+ 15-4 | 32 | 32 | 16 | >32 | >32 | 32 | >32 | 128 | >32 | >32 | 32 | 16 | 16 |
| ECO- 15-1 | 32 | 32 | 16 | >32 | >32 | >32 | >32 | 128 | >32 | >32 | 32 | 16 | 32 |
| ECO- 15-2 | 32 | 32 | 16 | >32 | >32 | >32 | >32 | 128 | >32 | 32 | 32 | 32 | 32 |
| ECO- 15-3 | 32 | 64 | 32 | >32 | >32 | >32 | >32 | 128 | >32 | 32 | 32 | 32 | 32 |

TABLE 3-continued

Anti-bacterial activities of the compounds

| | 32 | 64 | 16 | >32 | >32 | >32 | 128 | >32 | 32 | 32 | 32 |
|---|---|---|---|---|---|---|---|---|---|---|---|
| ECO-15-4 | 32 | 32 | 16 | >32 | >32 | >32 | 128 | >32 | 32 | 32 | 32 |
| EFA 15-1 | 2 | 2 | 4 | 4 | 32 | 8 | 4 | 32 | 16 | 4 | 4 |
| EFA 15-2 | 2 | 2 | 4 | 4 | 32 | 8 | 4 | 32 | 16 | 4 | 4 |
| EFA 15-3 | 2 | 2 | 1 | 4 | 32 | 8 | 2 | 32 | 16 | 4 | 0.25 |
| EFA 15-4 | 2 | 2 | 4 | 4 | 32 | 8 | 4 | 32 | 16 | 4 | 4 |
| EFA 15-5 | 2 | 2 | 4 | 4 | 32 | 8 | 4 | 32 | 16 | 4 | 4 |
| EFA 15-6 | 2 | 2 | 4 | 2 | 32 | 8 | 4 | 32 | 16 | 4 | 4 |
| EFA 15-9 | 0.25 | 0.5 | 1 | 2 | 4 | 4 | 2 | 16 | 16 | 2 | 1 |
| EFM 15-1 | 1 | 1 | 1 | 1 | 4 | 4 | 2 | 16 | 8 | 2 | 1 |
| EFM 15-2 | 0.25 | 0.125 | 0.5 | 0.25 | 2 | 1 | 0.25 | 2 | 2 | 2 | 0.5 |
| EFM 15-3 | 0.5 | 1 | 1 | 1 | 4 | 4 | 4 | 16 | 8 | 2 | 1 |
| EFM 15-4 | 0.25 | 1 | 1 | 1 | 2 | 4 | 4 | 8 | 8 | 1 | 0.25 |
| EFM 15-5 | 0.5 | 1 | 1 | 4 | 4 | 4 | 4 | 16 | 8 | 2 | 0.5 |
| EFM 15-6 | 0.25 | 0.125 | 0.125 | 1 | 1 | 1 | 0.06 | 0.125 | 16 | 2 | 0.5 | 0.25 |
| SPN 16-2 | 2 | 1 | 4 | 4 | 16 | 8 | 1 | 4 | 32 | 0.5 | 4 |
| SPN 16-4 | 2 | 1 | 0.5 | 1 | 4 | 4 | 0.25 | 4 | 16 | 4 | 2 | 0.5 |
| BCA 14-1 | 2 | 1 | 0.5 | 2 | 16 | 4 | 0.25 | 4 | 16 | 2 | 2 | 1 |
| BCA 14-4 | 0.25 | 0.25 | 0.125 | 1 | 2 | 2 | 0.06 | 1 | 16 | 4 | 2 | 1 |
| BCA 14-5 | 0.125 | 1 | 0.25 | 2 | 8 | 8 | 0.06 | 4 | 32 | 16 | 2 | 0.5 |
| BCA 14-6 | 0.25 | 0.125 | 0.125 | 1 | 2 | 1 | 0.03 | 2 | 16 | 4 | 2 | 1 |
| BCA 14-7 | 0.5 | 0.5 | 0.25 | 4 | 4 | 8 | 0.125 | 2 | 32 | 4 | 3 | 0.25 |
| BCA 14-8 | 0.5 | 0.25 | 0.25 | 1 | 2 | 1 | 0.06 | 2 | 32 | 8 | 2 | 0.25 |
| BCA 14-10 | 0.5 | 0.25 | 0.25 | 0.5 | 2 | 1 | 0.06 | 2 | 32 | 2 | 3 | 0.5 |

TABLE 3-continued

Anti-bacterial activities of the compounds

| Strain | Example | | | | | | | | | | | | |
|---|---|---|---|---|---|---|---|---|---|---|---|---|---|
| | 40 | 41 | 42 | 43 | 44 | 45 | 46 | 47 | 48 | 49 | 50 | 51 | 52 |
| MRSA 15-1 | 0.5 | 0.5 | 2 | 1 | 0.5 | 0.5 | 0.25 | 0.25 | 2 | 8 | >23 | 0.25 | >32 |
| MRSA 15-2 | 0.5 | 1 | 2 | 4 | 1 | 1 | 1 | 0.5 | 8 | 164 | >32 | 1 | >32 |
| MRSA 15-3 | 0.25 | 0.5 | 1 | 1 | 1 | 1 | 1 | 0.25 | 2 | 16 | >32 | 0.2 | >32 |
| MRSA 15-4 | 0.25 | 1 | 1 | 4 | 1 | 1 | 1 | 0.5 | 8 | 16 | >32 | 0.5 | >32 |
| MSSA 15-3 | 0.5 | 1 | 2 | 4 | 0.5 | 0.5 | 0.25 | 0.5 | 8 | 16 | >32 | 0.25 | >32 |
| MSSA 15-4 | 0.5 | 0.5 | 2 | 4 | 1 | 1 | 1 | 0.5 | 8 | 16 | >32 | 0.125 | >32 |
| MSSA 15-5 | 0.5 | 0.5 | 1 | 1 | 1 | 1 | 1 | 0.5 | 8 | >32 | >32 | 0.06 | >32 |
| MSSA 15-6 | 0.5 | 0.5 | 2 | 4 | >32 | >32 | >32 | >32 | >32 | >32 | >32 | 0.5 | >32 |
| MRSE 15-1 | 0.5 | 0.5 | 2 | 1 | 1 | 1 | 1 | 0.5 | 8 | >32 | >32 | 0.06 | >32 |
| MRSE 15-2 | 0.5 | 1 | 2 | 4 | 1 | 1 | 1 | 0.5 | 8 | >32 | >32 | 0.25 | >32 |
| MRSE 15-3 | 0.5 | 1 | 2 | 4 | 1 | 1 | 1 | 0.5 | 8 | >32 | >32 | 0.25 | >32 |
| MRSE 15-7 | 0.5 | 1 | 2 | 1 | 1 | 1 | 1 | 0.5 | 8 | >32 | >32 | 0.25 | >32 |
| MSSE 15-3 | 0.5 | 1 | 2 | 1 | 1 | 1 | 1 | 0.5 | 8 | >32 | >32 | 0.125 | >32 |
| MSSE 15-4 | 0.5 | 1 | 2 | 1 | 1 | 1 | 1 | 0.5 | 32 | >32 | >32 | 0.125 | >32 |
| MSSE 15-5 | 0.25 | 1 | 2 | 1 | 1 | 1 | 1 | 0.5 | 8 | >32 | >32 | 0.06 | >32 |
| MSSE 15-6 | 0.25 | 1 | 2 | 1 | 1 | 1 | 1 | 0.5 | 8 | >32 | >32 | 0.06 | >32 |
| ECO+ 15-1 | 32 | 32 | 16 | 1 | 32 | 32 | 32 | 32 | 8 | >32 | >32 | 16 | >32 |
| ECO+ 15-2 | 32 | 32 | 32 | >32 | >32 | >32 | >32 | >32 | >32 | >32 | >32 | >32 | >32 |
| ECO+ 15-3 | 32 | 32 | 32 | >32 | >32 | >32 | >32 | >32 | 32 | >32 | >32 | >32 | >32 |
| ECO+ 15-4 | 32 | 32 | 16 | 1 | 32 | 32 | 1 | 0.5 | 32 | >32 | >32 | 32 | >32 |
| ECO− 15-1 | 32 | 32 | 32 | >32 | >32 | >32 | >32 | >32 | >32 | >32 | >32 | >32 | >32 |
| ECO− 15-2 | 32 | 32 | 32 | >32 | >32 | >32 | >32 | >32 | >32 | >32 | >32 | >32 | >32 |
| ECO− 15-3 | 32 | 32 | 32 | >32 | >32 | >32 | >32 | >32 | >32 | >32 | >32 | >32 | >32 |

TABLE 3-continued

Anti-bacterial activities of the compounds

| | | | | | | | | | |
|---|---|---|---|---|---|---|---|---|---|
| ECO-15-4 | 32 | 32 | 32 | >32 | >32 | >32 | >32 | >32 | >32 |
| EFA 15-1 | 4 | 4 | 16 | >32 | >32 | >32 | >32 | 8 | >32 |
| EFA 15-2 | 4 | 4 | 16 | >32 | >32 | >32 | >32 | 8 | >32 |
| EFA 15-3 | 4 | 1 | 4 | >32 | >32 | >32 | >32 | 2 | >32 |
| EFA 15-4 | 4 | 4 | 16 | >32 | >32 | >32 | >32 | 8 | >32 |
| EFA 15-5 | 4 | 4 | 16 | >32 | >32 | >32 | >32 | 8 | >32 |
| EFA 15-6 | 4 | 4 | 16 | >32 | >32 | >32 | >32 | 8 | >32 |
| EFA 15-9 | 4 | 1 | 2 | 16 | 16 | 4 | 4 | 2 | >32 |
| EFM 15-1 | 1 | 2 | 4 | >32 | >32 | >32 | >32 | 2 | >32 |
| EFM 15-2 | 1 | 0.25 | 1 | >32 | >32 | >32 | >32 | 0.5 | >32 |
| EFM 15-3 | 0.25 | 1 | 4 | >32 | >32 | >32 | >32 | 2 | >32 |
| EFM 15-4 | 1 | 1 | 2 | 1 | 0.5 | 0.25 | 1 | 1 | 16 |
| EFM 15-5 | 1 | 2 | 4 | 2 | 0.5 | 1 | 8 | 2 | 16 |
| EFM 15-6 | 0.25 | 1 | 1 | 1 | 0.5 | 0.5 | 8 | 8 | 8 |
| SPN 16-2 | 0.25 | 0.25 | 16 | 1 | 0.5 | 0.5 | 4 | 0.5 | 8 |
| SPN 16-4 | 4 | 4 | 1 | 2 | 1 | 4 | >32 | 2 | >32 |
| BCA 14-1 | 1 | 1 | 2 | 4 | 1 | >32 | >32 | 2 | >32 |
| BCA 14-4 | 1 | 2 | 2 | 4 | 1 | 4 | 8 | 2 | >32 |
| BCA 14-5 | 0.5 | 0.25 | 2 | 1 | 0.5 | 0.25 | 4 | 0.5 | >32 |
| BCA 14-6 | 0.5 | 4 | 2 | 2 | 0.5 | 2 | >32 | 1 | >32 |
| BCA 14-7 | 0.25 | 1 | 1 | 4 | 1 | 1 | 16 | 0.5 | >32 |
| BCA 14-8 | 0.5 | 4 | 4 | 4 | 1 | 2 | 16 | 1 | >32 |
| BCA 14-10 | 0.2 | 0.5 | 1 | 2 | 1 | 0.5 | >32 | 0.5 | >32 |

TABLE 3-continued

Anti-bacterial activities of the compounds

| Strain | Example | | | | | | | | | | | | |
|---|---|---|---|---|---|---|---|---|---|---|---|---|---|
| | 53 | 54 | 55 | 56 | 57 | 58 | 59 | 60 | 61 | 62 | 63 | 64 | 65 |
| MRSA 15-1 | 16 | >32 | 0.25 | 0.25 | 0.5 | >32 | >32 | >32 | 1 | 0.125 | 0.125 | 0.03 | 0.06 |
| MRSA 15-2 | >32 | >32 | 0.5 | 2 | 0.5 | >32 | >32 | >32 | 1 | 0.5 | 0.25 | 0.06 | 0.125 |
| MRSA 15-3 | 16 | >32 | 0.5 | 0.5 | 0.5 | >32 | >32 | >32 | 1 | 0.5 | 0.125 | 0.03 | 0.06 |
| MRSA 15-4 | >32 | >32 | 0.5 | 2 | 0.5 | >32 | >32 | >32 | 1 | 0.5 | 0.25 | 0.06 | 0.125 |
| MSSA 15-3 | >32 | >32 | 0.5 | 0.25 | 0.5 | >32 | >32 | >32 | 1 | 0.5 | 0.125 | 0.06 | 0.125 |
| MSSA 15-4 | >32 | >32 | 1 | 0.125 | 0.125 | >32 | >32 | >32 | 1 | 0.5 | 0.125 | 0.03 | 0.015 |
| MSSA 15-5 | >32 | >32 | 1 | 0.25 | 0.125 | >32 | >32 | >32 | >32 | 16 | 16 | 16 | 16 |
| MSSA 15-6 | >32 | >32 | >32 | 0.125 | 0.125 | >32 | >32 | >32 | 1 | 16 | 0.25 | 0.06 | 0.015 |
| MRSE 15-1 | >32 | >32 | 1 | 2 | 0.125 | >32 | >32 | >32 | 1 | 16 | 0.25 | 0.06 | 0.125 |
| MRSE 15-2 | >32 | >32 | 1 | 0.25 | 0.25 | >32 | >32 | >32 | 1 | 0.5 | 0.25 | 0.06 | 0.125 |
| MRSE 15-3 | >32 | >32 | 1 | 0.5 | 0.25 | >32 | >32 | >32 | 1 | 0.5 | 0.25 | 0.06 | 0.125 |
| MRSE 15-7 | >32 | >32 | 1 | 0.25 | 0.125 | >32 | >32 | >32 | 1 | 0.5 | 0.125 | 0.03 | 0.0.15 |
| MSSE 15-3 | >32 | >32 | 1 | 0.06 | 0.125 | >32 | >32 | >32 | 1 | 0.5 | 0.25 | 0.06 | 0.125 |
| MSSE 15-4 | >32 | >32 | 1 | 0.06 | 0.06 | >32 | >32 | >32 | 1 | 0.5 | 0.25 | 0.06 | 0.06 |
| MSSE 15-5 | >32 | >32 | 1 | 0.06 | 0.06 | >32 | >32 | >32 | 32 | 0.5 | 0.125 | >0.008 | 0.015 |
| MSSE 15-6 | >32 | >32 | 32 | >16 | 32 | >32 | >32 | >32 | >32 | 0.5 | 16 | 16 | 8 |
| ECO+ 15-1 | >32 | >32 | >32 | >16 | >32 | >32 | >32 | >32 | >32 | 0.5 | 32 | 32 | 8 |
| ECO+ 15-2 | >32 | >32 | >32 | >16 | >32 | >32 | >32 | >32 | 1 | 0.5 | 16 | 16 | 16 |
| ECO+ 15-3 | >32 | >32 | >32 | >16 | >32 | >32 | >32 | >32 | 1 | 0.5 | 16 | 16 | 16 |
| ECO+ 15-4 | >32 | >32 | >32 | >16 | >32 | >32 | >32 | >32 | >32 | 16 | 16 | 16 | 8 |
| ECO− 15-1 | >32 | >32 | >32 | >16 | >32 | >32 | >32 | >32 | >32 | 16 | 16 | 16 | 16 |
| ECO− 15-2 | >32 | >32 | >32 | >16 | >32 | >32 | >32 | >32 | >32 | 16 | 32 | 32 | 16 |
| ECO− 15-3 | >32 | >32 | >32 | >16 | >32 | >32 | >32 | >32 | >32 | 16 | 32 | 32 | 16 |

TABLE 3-continued

Anti-bacterial activities of the compounds

| | 1 | 2 | 3 | 4 | 5 | 6 | 7 | 8 | 9 | 10 |
|---|---|---|---|---|---|---|---|---|---|---|
| ECO-15-4 | >32 | >32 | >16 | >32 | >32 | >32 | 16 | 16 | 16 | 8 |
| EFA 15-1 | >32 | >32 | 16 | 8 | >32 | >32 | >32 | >32 | 32 | |
| EFA 15-2 | >32 | >32 | 16 | 8 | >32 | >32 | >32 | >32 | 32 | |
| EFA 15-3 | >32 | >32 | 16 | 8 | >32 | >32 | >32 | >32 | 32 | |
| EFA 15-4 | >32 | >32 | 16 | 8 | >32 | >32 | >32 | >32 | 32 | |
| EFA 15-5 | >32 | >32 | 16 | 8 | >32 | >32 | >32 | >32 | 32 | |
| EFA 15-6 | >32 | 32 | 16 | 8 | >32 | >32 | >32 | >32 | 4 | |
| EFA 15-9 | >32 | >32 | 1 | 1 | >32 | >32 | 8 | 4 | 4 | |
| EFM 15-1 | >32 | >32 | 4 | 2 | >32 | >32 | >32 | >32 | >32 | |
| EFM 15-2 | >32 | >32 | 1 | 0.25 | >32 | >32 | >32 | >32 | >32 | |
| EFM 15-3 | >32 | >32 | 4 | 1 | >32 | >32 | >32 | >32 | >32 | |
| EFM 15-4 | 32 | 0.5 | 1 | 0.5 | 8 | 16 | 0.215 | 0.5 | 0.25 | |
| EFM 15-5 | 32 | 2 | 8 | 4 | 8 | 16 | 1 | 0.5 | 0.25 | 0.125 |
| EFM 15-6 | 32 | 8 | 4 | 2 | 8 | 8 | 32 | 0.25 | 0.25 | 1 |
| SPN 16-2 | 32 | 4 | 1 | 0.25 | >32 | 16 | 2 | 0.5 | 0.5 | 0.125 |
| SPN 16-4 | 32 | 4 | 1 | 0.25 | >32 | 8 | 2 | 0.5 | 0.125 | 0.06 |
| BCA 14-1 | >32 | >32 | 4 | 0.5 | >32 | >32 | 8 | 2 | 0.25 | 0.5 |
| BCA 14-4 | >32 | >32 | 4 | 0.5 | >32 | >32 | 8 | 2 | 1 | 0.5 |
| BCA 14-5 | >32 | 32 | 1 | 0.5 | >32 | 16 | 1 | 0.5 | 1 | 0.125 |
| BCA 14-6 | >32 | >32 | 2 | 1 | >32 | >32 | 1 | 2 | 1 | 0.125 |
| BCA 14-7 | >32 | >32 | 4 | 0.25 | >32 | >32 | 8 | 4 | 1 | 0.5 |
| BCA 14-8 | >32 | >32 | 2 | 0.25 | >32 | >32 | 8 | 0.5 | 0.125 | 0.5 |
| BCA 14-10 | >32 | >32 | 2 | 0.25 | >32 | >32 | 8 | 1 | 0.125 | 0.125 |

TABLE 3-continued

Anti-bacterial activities of the compounds

| Strain | 66 | 67 | 68 | 69 | 70 | 71 | 72 | 73 | 74 | 75 | 76 | 77 | 78 |
|---|---|---|---|---|---|---|---|---|---|---|---|---|---|
| MRSA 15-1 | 0.5 | 0.25 | >32 | 2 | 0.5 | 0.125 | 0.06 | 0.03 | 4 | 1 | >32 | 0.25 | 0.06 |
| MRSA 15-2 | 2 | 0.5 | >32 | 8 | 1 | 1 | 0.125 | 0.06 | 8 | 2 | >32 | 0.5 | 0.5 |
| MRSA 15-3 | 0.5 | 0.25 | >32 | 2 | 0.5 | 0.125 | 0.06 | 0.06 | 5 | 1 | >32 | 0.25 | 0.125 |
| MRSA 15-4 | 1 | 0.5 | >32 | 8 | 1 | 0.5 | 0.125 | 0.06 | 8 | 1 | >32 | 0.5 | 0.5 |
| MSSA 15-3 | 1 | 0.5 | >32 | 8 | 2 | 0.25 | 0.125 | 0.06 | 4 | 2 | >32 | 0.5 | 0.5 |
| MSSA 15-4 | 0.5 | 0.125 | >32 | 2 | 0.5 | 0.1254 | 0.06 | 0.06 | 4 | 0.5 | >32 | 0.125 | 0.125 |
| MSSA 15-5 | 0.5 | 0.125 | >32 | 2 | 0.25 | 0.06 | 0.03 | 0.03 | 2 | 0.5 | >32 | 0.125 | 0.03 |
| MSSA 15-6 | 32 | 32 | >32 | >32 | 16 | 0.25 | 16 | 0.06 | 4 | 16 | >32 | >32 | >32 |
| MRSE 15-1 | 0.25 | 0.5 | >32 | 8 | 0.5 | 0.06 | 0.03 | <0.008 | 0.5 | 1 | >32 | 0.5 | 0.125 |
| MRSE 15-2 | 1 | 0.5 | >32 | 8 | 2 | 0.125 | 0.125 | 0.015 | 1 | 2 | >32 | 2 | 1 |
| MRSE 15-3 | 1 | 0.5 | >32 | 8 | 2 | 0.125 | 0.125 | <0.008 | 1 | 4 | >32 | 2 | 1 |
| MRSE 15-7 | 1 | 0.5 | >32 | 8 | 2 | 0.25 | 0.06 | 0.06 | 4 | 4 | >32 | 2 | 1 |
| MSSE 15-3 | 0.06 | 0.25 | >32 | 1 | 0.5 | 0.16 | 0.06 | 0.015 | 1 | 1 | >32 | 0.5 | 0.25 |
| MSSE 15-4 | 1 | 0.5 | >32 | 8 | 1 | 0.06 | 0.125 | <0.008 | 1 | 1 | >32 | 2 | 0.25 |
| MSSE 15-5 | 1 | 0.5 | >32 | 8 | 1 | 0.06 | 0.125 | <0.008 | 1 | 1 | >32 | 2 | 0.25 |
| MSSE 15-6 | 0.06 | 0.125 | >32 | 2 | 0.25 | 0.06 | <0.008 | <0.008 | 1 | 0.5 | >32 | 0.125 | 0.03 |
| ECO+ 15-1 | 16 | 16 | >32 | 32 | 16 | 16 | 16 | 16 | 32 | 16 | >32 | 0.125 | 16 |
| ECO+ 15-2 | 32 | 16 | >32 | 32 | 32 | 16 | 16 | 32 | >32 | 32 | >32 | >32 | >32 |
| ECO+ 15-3 | 16 | 32 | >32 | 32 | 32 | 32 | 16 | 32 | >32 | 32 | >32 | >32 | >32 |
| ECO+ 15-4 | 16 | 32 | >32 | 16 | 16 | 32 | 16 | 32 | >32 | 16 | >32 | >32 | >32 |
| ECO− 15-1 | 16 | 32 | >32 | 32 | 16 | 16 | 16 | 32 | >32 | 16 | >32 | >32 | >32 |
| ECO− 15-2 | 16 | 32 | >32 | 32 | 32 | 16 | 16 | 32 | >32 | 32 | >32 | >32 | >32 |
| ECO− 15-3 | 32 | 32 | >32 | 32 | 32 | 16 | 16 | 32 | >32 | 32 | >32 | >32 | >32 |

TABLE 3-continued

Anti-bacterial activities of the compounds

| | | | | | | | | | |
|---|---|---|---|---|---|---|---|---|---|
| ECO-15-4 | 8 | 32 | 32 | 16 | 32 | 16 | 32 | >32 | >32 |
| EFA 15-1 | 4 | 32 | >32 | 32 | 2 | 32 | >32 | >32 | >32 |
| EFA 15-2 | 4 | 32 | >32 | 32 | 2 | 32 | >32 | >32 | >32 |
| EFA 15-3 | 2 | 32 | >32 | 32 | 0.5 | 32 | 16 | >32 | >32 |
| EFA 15-4 | 16 | 32 | >32 | 32 | 2 | 32 | >32 | >32 | >32 |
| EFA 15-5 | 16 | 32 | >32 | 32 | 2 | 32 | >32 | >32 | >32 |
| EFA 15-6 | 16 | 32 | 32 | >32 | 1 | 2 | >32 | >32 | >32 |
| EFA 15-9 | 16 | 32 | >32 | >32 | 0.5 | 32 | 16 | >32 | >32 |
| EFM 15-1 | 16 | 32 | >32 | >32 | 2 | 32 | 32 | >32 | >32 |
| EFM 15-2 | 16 | >32 | >32 | >32 | 0.25 | 0.125 | 4 | >32 | >32 |
| EFM 15-3 | 16 | >32 | >32 | >32 | 1 | 1 | 32 | >32 | >32 |
| EFM 15-4 | 1 | 2 | 32 | 32 | 2 | 1 | 32 | 16 | 2 |
| EFM 15-5 | 0.125 | 4 | 8 | 0.2 | 0.125 | 0.125 | 4 | 16 | 0.25 |
| EFM 15-6 | 0.5 | 4 | 8 | 2 | 0.5 | 1 | 2 | 32 | 1 |
| SPN 16-2 | 0.25 | 2 | 2 | 0.5 | 2 | 1 | 1 | 8 | 0.03 |
| SPN 16-4 | 0.25 | 1 | 1 | 0.25 | 0.25 | 0.125 | 0.5 | 4 | 0.25 |
| BCA 14-1 | 2 | 32 | >32 | 1 | 0.5 | 1 | 4 | 2 | 0.5 |
| BCA 14-4 | 2 | 32 | >32 | 2 | 0.5 | 0.5 | 8 | >32 | 1 |
| BCA 14-5 | 2 | 4 | 8 | 2 | 0.25 | 0.125 | 2 | >32 | 2 |
| BCA 14-6 | 2 | 32 | >32 | 2 | 0.5 | 1 | 8 | >32 | 0.125 |
| BCA 14-7 | 2 | 32 | >32 | 4 | 0.5 | 0.125 | 4 | >32 | 0.5 |
| BCA 14-8 | 2 | 32 | >32 | 1 | 0.25 | 0.25 | 4 | >32 | 0.5 |
| BCA 14-10 | 0.5 | 2 | 4 | 1 | 0.125 | 0.125 | 2 | >32 | 0.25 |

TABLE 3-continued

Anti-bacterial activities of the compounds

| Strain | Example 79 | 80 | LBM415 | levofloxacin |
|---|---|---|---|---|
| MRSA 15-1 | 0.25 | 1 | 1 | 64 |
| MRSA 15-2 | 0.25 | 2 | 1 | >128 |
| MRSA 15-3 | 0.125 | 1 | 1 | >128 |
| MRSA 15-4 | 0.25 | 2 | 0.5 | >128 |
| MSSA 15-3 | 0.5 | 2 | 0.5 | 16 |
| MSSA 15-4 | 0.125 | 1 | 0.5 | 16 |
| MSSA 15-5 | 0.125 | 0.5 | 0.5 | 0.5 |
| MSSA 15-6 | >32 | 1 | 0.5 | 64 |
| MRSE 15-1 | 0.25 | 0.25 | 0.125 | 16 |
| MRSE 15-2 | 2 | 0.5 | 0.125 | 16 |
| MRSE 15-3 | 2 | 0.5 | 0.06 | 16 |
| MRSE 15-7 | 2 | 2 | 0.125 | 16 |
| MSSE 15-3 | 0.25 | 1 | 0.06 | 0.5 |
| MSSE 15-4 | 1 | 0.25 | 0.5 | 0.5 |
| MSSE 15-5 | 1 | 0.25 | 0.06 | 0.5 |
| MSSE 15-6 | 0.03 | 0.25 | 0.06 | 0.25 |
| ECO+ 15-1 | 32 | >16 | 128 | 32 |
| ECO+ 15-2 | >32 | 16 | 64 | 64 |
| ECO+ 15-3 | 32 | >16 | 64 | 32 |
| ECO+ 15-4 | 32 | >16 | 64 | 1 |
| ECO− 15-1 | 32 | >16 | 64 | 0.03 |
| ECO− 15-2 | >32 | >16 | 64 | 128 |
| ECO− 15-3 | >32 | >16 | 64 | 0.06 |
| ECO− 15-4 | >32 | >16 | 64 | 0.06 |
| EFA 15-1 | 32 | 16 | 2 | >128 |
| EFA 15-2 | 32 | >16 | 2 | >128 |
| EFA 15-3 | 32 | 8 | 2 | 32 |
| EFA 15-4 | 32 | >16 | 2 | 1 |
| EFA 15-5 | 32 | >16 | 2 | >128 |
| EFA 15-6 | 32 | >16 | 128 | 128 |
| EFA 15-9 | 32 | >16 | 128 | 0.06 |
| EFM 15-1 | 32 | 8 | 2 | >128 |
| EFM 15-2 | 32 | 4 | 4 | >128 |
| EFM 15-3 | 32 | 8 | 8 | >128 |
| EFM 15-4 | 1 | 4 | 4 | >128 |
| EFM 15-5 | 1 | 2 | 4 | >128 |
| EFM 15-6 | 1 | 8 | 2 | 128 |
| SPN 16-2 | 0.06 | 4 | 2 | 1 |
| SPN 16-4 | 0.25 | 8 | 2 | 1 |
| BCA 14-1 | 0.25 | 4 | 2 | 1 |
| BCA 14-4 | 1 | 8 | 1 | 2 |
| BCA 14-5 | 0.25 | 2 | 2 | 2 |
| BCA 14-6 | 1 | 8 | 2 | 4 |
| BCA 14-7 | 0.5 | 4 | 0.5 | 8 |
| BCA 14-8 | 0.5 | 8 | 0.5 | 1 |
| BCA 14-10 | 0.25 | 4 | 0.5 | 2 |

TABLE 4

Anti-proliferation inhibition rate activity of the compounds on colorectal cancer cell at a concentration of 30 μM

| Example | 1 | 2 | 3 | 4 | 5 | 6 | 7 | 8 | 9 | 10 | 11 | 12 | 13 |
|---|---|---|---|---|---|---|---|---|---|---|---|---|---|
| HCT116 inhibition rate/% | 7 | 2 | 2 | 18 | −15 | 86 | 23 | 11 | 6 | 10 | 17 | 13 | 13 |
| Example | 14 | 15 | 16 | 17 | 18 | 19 | 20 | 21 | 22 | 23 | 24 | 25 | 26 |
| HCT116 inhibition rate/% | 21 | 24 | 24 | 13 | 5 | 6 | 13 | 8 | 52 | 7 | 2 | 35 | 18 |
| Example | 27 | 28 | 29 | 30 | 31 | 32 | 33 | 34 | 35 | 36 | 37 | 38 | 39 |
| HCT116 inhibition rate/% | 17 | 21 | 94 | 17 | 19 | 30 | 31 | 36 | −1 | 60 | 16 | 52 | −10 |
| Example | 40 | 41 | 42 | 43 | 44 | 45 | 46 | 47 | 48 | 49 | 50 | 51 | 52 |
| HCT116 inhibition rate/% | 78 | 24 | 14 | 6 | 21 | 25 | 58 | 20 | 20 | 8 | −11 | 65 | −1 |
| Example | 53 | 54 | 55 | 56 | 57 | 58 | 59 | 60 | 61 | 62 | 63 | 64 | 65 |
| HCT116 inhibition rate/% | −18 | 8 | 30 | 10 | 52 | 24 | 12 | −2 | 35 | 79 | 68 | 87 | 83 |
| Example | 66 | 67 | 68 | 69 | 70 | 71 | 72 | 73 | 74 | 75 | 76 | 77 | 78 |
| HCT116 inhibition rate/% | 75 | 44 | 21 | 15 | 64 | 30 | 75 | 78 | 1 | 59 | 87 | 30 | 52 |
| Example | 79 | 80 | | | | | | | | | | | |
| HCT116 inhibition rate/% | 75 | 11 | | | | | | | | | | | |

The results showed that the inhibition rates of 21 compounds in Examples 6, 22, 29, 36, 38, 40, 46, 51, 57, 62, 63, 64, 65, 66, 70, 72, 73, 75, 76, 78, 79 at a concentration of 30 μM on the proliferation of colorectal cancer cell HCT116 was in excess of 50%, wherein, the compound of Example 29 had the highest proliferation inhibition rate of 94%. It was indicated that the synthesized compounds have significant inhibiting effects on the proliferation of colorectal cancer cell HCT116 at a concentration of 30 μM.

TABLE 5

Inhibition activity of preferred compounds on the proliferation of colorectal cancer cells, lung cancer cells, gastric cancer cells, liver cancer cells and the like, at a concentration of 30 μM

| Example | Colorectal cancer HCT116 | Lung cancer A549 | Gastric cancer MGC-803 | Liver cancer BEL-7402 |
|---|---|---|---|---|
| 6 | 86 | 26 | 66 | 74 |
| 22 | 52 | 21 | 14 | 51 |
| 25 | 35 | 30 | 27 | 65 |
| 29 | 94 | 36 | 78 | 79 |
| 32 | 30 | 14 | 14 | 46 |
| 33 | 31 | 20 | 27 | 57 |
| 34 | 36 | 35 | 26 | 63 |
| 36 | 60 | 26 | 46 | 73 |
| 38 | 52 | 38 | 50 | 75 |
| 40 | 78 | 30 | 63 | 73 |
| 46 | 58 | 60 | 48 | 70 |
| 51 | 65 | 44 | 40 | 68 |
| 55 | 30 | 49 | 33 | 59 |
| 57 | 52 | 52 | 34 | 57 |
| 61 | 35 | 10 | 31 | 50 |
| 62 | 79 | 59 | 64 | 75 |
| 63 | 68 | 63 | 58 | 74 |
| 64 | 87 | 61 | 63 | 81 |
| 65 | 83 | 67 | 72 | 81 |
| 66 | 75 | 56 | 60 | 74 |
| 67 | 44 | 36 | 39 | 57 |
| 70 | 64 | 54 | 50 | 62 |
| 71 | 30 | 5 | 34 | 49 |
| 72 | 75 | 50 | 63 | 76 |
| 73 | 78 | 63 | 65 | 81 |
| 75 | 59 | 45 | 51 | 70 |
| 76 | 87 | 94 | 64 | 67 |
| 77 | 30 | 16 | 19 | 49 |
| 78 | 52 | 54 | 44 | 67 |
| 79 | 75 | 50 | 54 | 77 |

30 compounds that had good inhibition effect on the proliferation of colorectal cancer cell HCT116 (inhibition rate≥30%) in Examples 6, 22, 25, 29, 32, 33, 34, 36, 38, 40, 46, 51, 55, 57, 61, 62, 63, 64, 65, 66, 67, 70, 71, 72, 73, 75, 76, 77, 78, 79 were selected, and their inhibition rate activities on the proliferation of other cancer cells such as lung cancer cells, gastric cancer cells, liver cancer cells, and the like were examined. The results showed that: the inhibiton rates of 13 compounds in Examples 46, 57, 62, 63, 64, 65, 66, 70, 72, 73, 76, 78, 79 at a concentration of 30 μM on the proliferation of lung cancer cell A549 was in excess of 50%, wherein the compound of Example 76 had the highest proliferation inhibition rate of 94%; the inhibiton rates of 14 compounds of Examples 6, 29, 38, 40, 62, 63, 64, 65, 66, 72, 73, 75, 76, 79 at a concentration of 30 μM on the proliferation of gastric cancer cell MGC-803 was in excess of 50%, wherein, the compound of Example 29 had the highest proliferation inhibition rate of 78%; the inhibiton rates of 27 compounds of Examples 6, 22, 25, 29, 33, 34, 36, 38, 40, 46, 51, 55, 57, 62, 63, 64, 65, 66, 67, 70, 72, 73, 75, 76, 77, 78, 79 at a concentration of 30 μM on the proliferation of liver cancer cell BEL-7402 was in excess of 50%, wherein, the compounds of Examples 64, 65 and 73 had the highest proliferation inhibition rate of 81%.

TABLE 6

IC50 values (μM) of preferred compounds against colorectal cancer cell, lung cancer cell, gastric cancer cell, and liver cancer cell

| Examples | Liver cancer cell BEL-7402 | Lung cancer cell A549 | Colorectal cancer cell HCT-116 | Gastric cancer cell MGC-803 |
|---|---|---|---|---|
| 29 | 7.57 | 13.63 | 8.962 | 7.843 |
| 55 | 25.95 | 12.12 | 15.24 | 29.54 |
| 64 | 5 | 4.86/ | 4.88 | 6.11 |
| 73 | 10 | 5.12 | 6.21 | 12.65 |
| 76 | 8.58 | 9.293 | 10.77 | 16.56 |

TABLE 7

Inhibition rate on growth of different tumor cells of Example 64 (IC50, μM)

| Source of tissue for cells | Name of cells | IC$_{50}$ (μM) |
|---|---|---|
| Rectal cancer | HCT-116 | 4.88 |
| T-cell leukemia | Jurkat | 7.61 |
| Acute myeloid leukemia | HL60 | 1.21 |
| Liver cancer | BEL7402 | 5.00 |
| Lung cancer | A549 | 4.86 |
| Cervical cancer | Hela | 11.45 |
| Gastric cancer | MGC-803 | 6.11 |
| Breast cancer | MCF-7 | 6.62 |
| Prostate cancer | PC3 | 6.17 |
| Steosarcoma | SAOS-2 | 2 |

Example 1

Synthesis of (S)-5-((R)-2-4N-hydroxyformamido)methyl)hexanamido)-N-(1H-pyrazol-3-yl)-5-azaspiro[2.4]heptane-6-amide

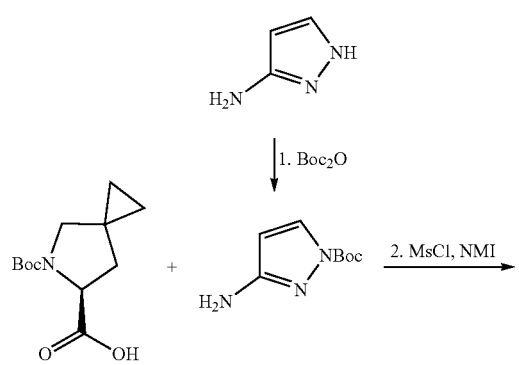

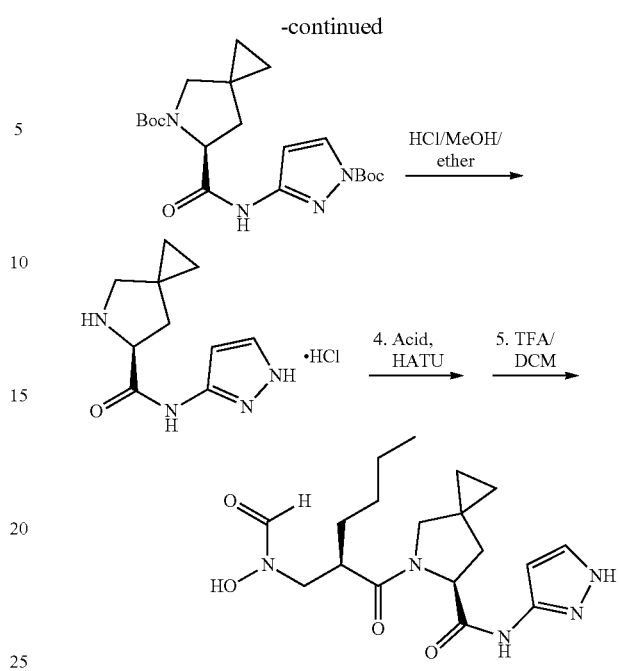

Step 1: 3-aminopyrazole (1.50 g, 18.0 mmol), trimethylamine (4.5 g, 20.6 mmol), and 4-(dimethylamino)pyridine (0.15 g, 1.2 mmol) were added into 60 mL of dioxane. The mixture was stirred and dissolved, and then added with Boc$_2$O, and heated to reflux for 8 hours. After completion of the reaction, the solvent was removed by rotary evaporation. The residue was then diluted with EA, and extracted, and washed with 10% citric acid and saturated sodium chloride successively. Oil obtained by the concentration of organic phase was passed column (PE/DCM=2/1) to give a white solid product (1.6 g, 48% yield).

Step 2: The procedure was the same as the Step 1 in the synthesis of the general formula (X1). To an acid (2.05 g, 8.5 mmol) was added 20 mL of DMF, and N-methylimidazole (1.54 g, 18.7 mmol) under ice bath, and then was slowly dropwise added MsCl (1.07 g, 9.4 mmol). The mixture was stirred for 15 min, and then was added with Boc-protected amine (1.56 g, 8.5 mmol). The reaction was monitored by TLC. After the completion of the reaction, the reaction mixture was diluted with EA, and washed with 10% citric acid. The aqueous phase was extracted twice with 50 mL of EA. The combined organic phase was washed with saturated sodium bicarbonate and saturated sodium chloride successively. The oil product was obtained through organic phase concentration.

Step 3: 20 mL and 10 mL of 5 M HCl/MeOH solution were added to the oil, and the mixture was reacted at room temperature overnight. After the completion of the reaction, the mixture was dried by rotary evaporation to give an oil product (2.0 g, two-step yield of 100%).

$^1$H NMR (400 MHz, DMSO) δ 11.53 (s, 1H), 10.66 (d, J=4.0 Hz, 1H), 8.94 (s, 1H), 7.79 (s, 1H), 6.52 (s, 1H), 4.70-4.51 (m, 1H), 3.31-3.24 (m, 1H), 3.21-3.15 (m, 1H), 2.43-2.27 (m, 1H), 2.01 (dd, J=12.7, 7.5 Hz, 1H), 0.80-0.57 (m, 4H).

$^{13}$C NMR (101 MHz, DMSO) δ 165.97, 144.77, 96.15, 55.94, 51.54, 37.61, 18.42, 10.22, 9.83.

Step 4: The procedure was the same as the Step 3 in the synthesis of the general formula (X2).

Step 5: The procedure was the same as the Step 4 in the synthesis of the general formula (X2). The yield reached 18% through two-step synthesis process.

LC-MS (ESI): [M+1]$^+$=378.15, $t_R$=1.88 min.

$^1$H NMR (400 MHz, CDCl$_3$) δ 8.36-7.98 (m, 1H), 7.80-7.75 (m, 1H), 6.00-5.84 (m, 1H), 5.67-5.41 (m, 1H), 5.15 (s, 1H), 4.40-3.87 (m, 2H), 3.86-3.31 (m, 2H), 3.26-2.72 (m, 1H), 2.44-2.36 (m, 1H), 2.07-1.83 (m, 1H), 1.84-1.65 (m, 1H), 1.67-1.21 (m, 5H), 0.97-0.82 (m, 3H), 0.76-0.42 (m, 4H).

$^{13}$C NMR (101 MHz, CDCl$_3$) δ 172.19, 167.99, 158.69, 157.56, 129.84, 101.83, 58.87, 54.75, 51.31, 40.60, 37.93, 29.81, 28.93, 22.74, 20.77, 13.96, 12.89, 8.80.

HRMS (ESI): calculated for C$_{18}$H$_{27}$N$_5$O$_4$Na [M+Na]$^+$ =400.1961; found 400.1949.

Example 2

Synthesis of 5-fluoro-2-((S)-5-((R)-2-4N-hydroxy-formamido)methyl)hexylcarbonyl)-5-azaspiro[2.4]heptane-6-amido)pyridine N-nitrogen oxide

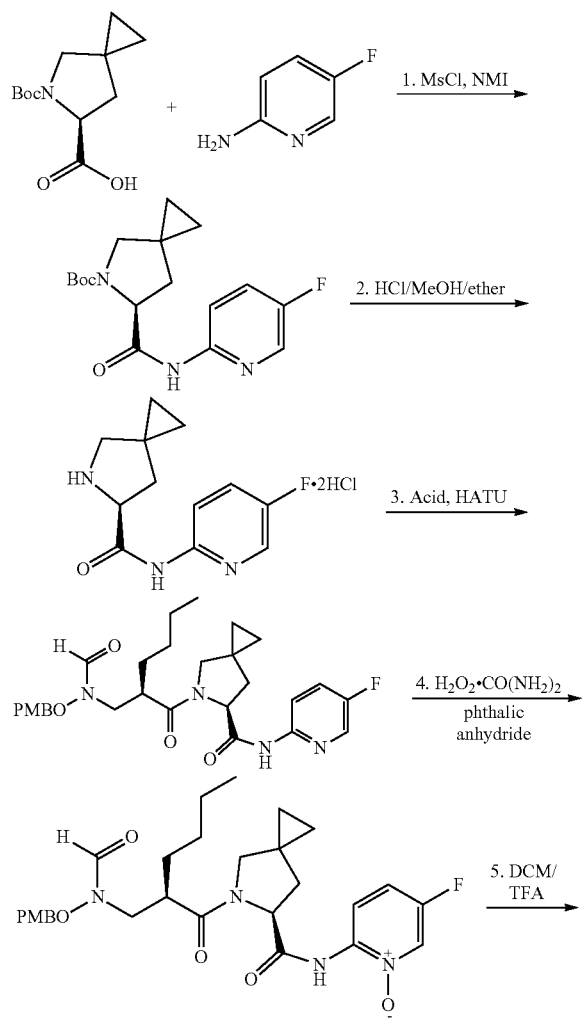

Step 1: The procedure was the same as the Step 1 in the synthesis of the general formula (X1).

Step 2: The procedure was the same as the Step 2 in the synthesis of the general formula (X1) (2.1 g, white solid, two-step yield of 68%).

Step 3: The procedure was the same as the Step 3 in the synthesis of the general formula (X2).

Step 4: In ethyl acetate (3 mL) was dissolved the obtained oil product (242 mg, 0.46 mmol), and then was added hydrogen peroxide urea complex (133 mg, 1.40 mmol) and phthalic anhydride (207 mg, 1.40 mmol). The mixture was stirred at room temperature for 2 hours. After the completion of the reaction, the reaction was quenched with sodium thiosulfate, and the mixture was extracted with ethyl acetate. The organic phase was dried and concentrated to give a crude product.

Step 5: The procedure was the same as the Step 4 in the synthesis of the general formula (X2). The yield reached 45% through three-step synthesis process.

LC-MS (ESI): [M+1]$^+$=423.02, $t_R$=1.80 min.

$^1$H NMR (400 MHz, CDCl$_3$) δ 10.55 (s, 1H), 8.49 (dd, J=9.4, 6.6 Hz, 1H), 8.21-8.18 (m, 1H), 7.79 (s, 1H), 7.19-7.09 (m, 1H), 4.97 (dd, J=8.5, 3.6 Hz, 1H), 4.00-3.78 (m, 2H), 3.50-3.26 (m, 2H), 3.17-2.80 (m, 1H), 2.40-2.25 (m, 1H), 2.11-1.92 (m, 1H), 1.80-1.46 (m, 2H), 1.44-1.26 (m, 4H), 0.89 (t, J=6.8 Hz, 3H), 0.76-0.61 (m, 4H).

$^{13}$C NMR (101 MHz, CDCl$_3$) δ 173.35, 170.54, 157.91, 154.73 (d, J=248.1 Hz), 141.69, 127.21 (d, J=36.5 Hz), 115.69 (d, J=20.1 Hz), 114.77 (d, J=7.8 Hz), 61.81, 54.81, 51.31, 40.55, 36.87, 29.81, 28.96, 22.67, 21.25, 13.87, 12.94, 8.46.

HRMS (ESI): calculated for C$_{20}$H$_{27}$N$_4$O$_5$NaF[M+Na]$^+$ =445.1863; found 445.1845.

Example 3

Synthesis of (S)—N-(5-(tert-butypisoxazol-3-yl)-5-((R)-2-((N-hydroxyformamido)methyl)hexylcarbonyl)-5-azaspiro[2.4]heptane-6-amide

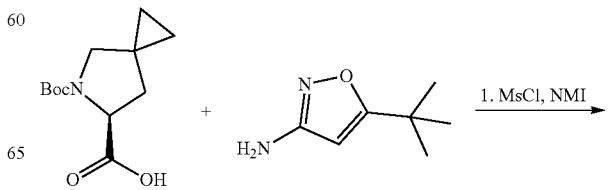

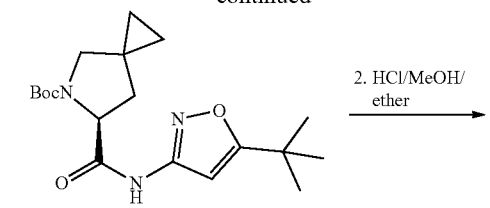

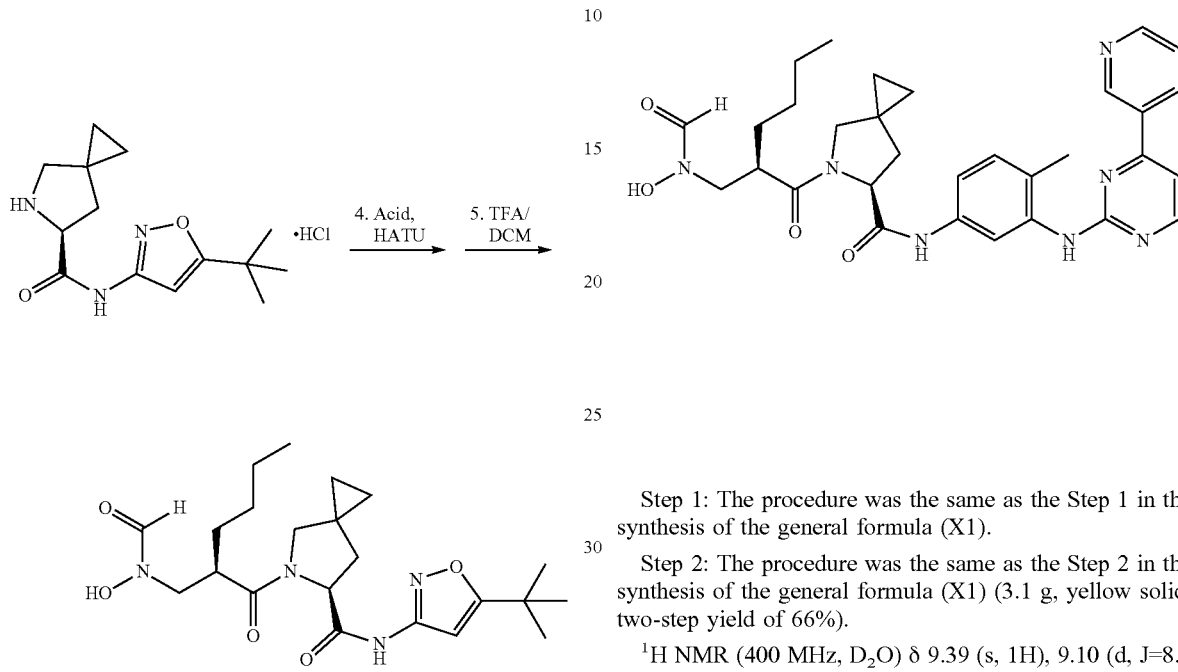

Step 1: The procedure was the same as the Step 1 in the synthesis of the general formula (X1).

Step 2: The procedure was the same as the Step 2 in the synthesis of the general formula (X1) (1.4 g, white solid, two-step yield of 47%).

1H NMR (400 MHz, D$_2$O) δ 6.14 (s, 1H), 4.44-4.41 (m, 1H), 3.12-2.93 (m, 2H), 2.19 (dd, J=13.4, 8.9 Hz, 1H), 1.86 (dd, J=13.4, 6.1 Hz, 1H), 0.52-0.29 (m, 4H).

$^{13}$C NMR (101 MHz, D$_2$O) δ 183.22, 167.90, 157.06, 93.24, 60.23, 52.67, 37.13, 32.51, 27.67, 20.09, 9.86, 8.49.

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 28%.

LC-MS (ESI): [M+1]$^+$=435.24, $t_R$=2.25 min.

$^1$H NMR (400 MHz, CDCl$_3$) δ 9.94 (s, 1H), 7.81 (s, 1H), 6.69 (s, 1H), 4.84 (dd, J=8.2, 4.2 Hz, 1H), 4.07-3.68 (m, 2H), 3.68-3.30 (m, 2H), 3.20-2.80 (m, 1H), 2.36-1.95 (m, 2H), 1.74-1.43 (m, 2H), 1.39-1.23 (m, 13H), 0.91-0.82 (m, 3H), 0.76-0.60 (m, 4H).

$^{13}$C NMR (101 MHz, CDCl$_3$) δ 181.38, 173.47, 169.95, 157.67, 157.62, 93.55, 61.29, 55.06, 51.36, 40.77, 36.21, 32.98, 29.85, 28.92, 28.64, 22.70, 21.28, 13.85, 12.41, 9.18.

HRMS (ESI): calculated for C$_{22}$H$_{34}$N$_4$O$_5$Na [M+Na]$^+$=457.2427; found 457.2426.

Example 4

Synthesis of (S)-5-((R)-2-4N-hydroxyformamido)methyl)hexylcarbonyl)-N-(4-methyl-3-((4-(pyridin-3-yl))pyrimidin-2-yl)amino)phenyl)-5-azaspiro[2.4]heptane-6-amide Step 1: The procedure was the same as the Step 1 in the synthesis of the general formula (X1).

Step 2: The procedure was the same as the Step 2 in the synthesis of the general formula (X1) (3.1 g, yellow solid, two-step yield of 66%).

$^1$H NMR (400 MHz, D$_2$O) δ 9.39 (s, 1H), 9.10 (d, J=8.1 Hz, 1H), 8.87 (d, J=5.5 Hz, 1H), 8.39 (d, J=6.1 Hz, 1H), 8.16-8.11 (m, 1H), 7.63 (s, 1H), 7.55 (d, J=6.2 Hz, 1H), 7.25 (d, J=8.2 Hz, 1H), 7.16 (d, J=7.9 Hz, 1H), 4.66-4.60 (m, 1H), 3.27 (d, J=3.3 Hz, 2H), 2.39 (dd, J=13.1, 8.9 Hz, 1H), 2.12 (s, 3H), 2.10-2.00 (m, 1H), 0.73-0.57 (m, 4H).

$^{13}$C NMR (101 MHz, D$_2$O) δ 167.92, 164.58, 155.40, 151.87, 145.43, 143.57, 141.24, 135.16, 134.34, 133.74, 131.92, 131.34, 127.79, 120.66, 118.45, 108.22, 60.22, 52.71, 37.45, 20.18, 16.50, 9.61, 8.85.

Step 3: The procedure was the same as the Step 3 in the synthesis of the general formula (X2).

Step 4: The procedure was the same as the Step 4 in the synthesis of the general formula (X2). Light yellow solid was obtained through column chromatography (DCM:MeOH=10:1), with a two-step yield of 38%.

LC-MS (ESI): [M+1]$^+$=572.27, $t_R$=2.11 min.

$^1$H NMR (400 MHz, CDCl$_3$) δ 9.38 (s, 1H), 9.24 (s, 1H), 8.67 (d, J=4.0 Hz, 1H), 8.51-8.25 (m, 3H), 7.87 (s, 1H), 7.49-7.39 (m, 1H), 7.38-7.05 (m, 4H), 5.06-4.61 (m, 1H), 4.13-3.61 (m, 2H), 3.57-3.22 (m, 2H), 3.19-2.84 (m, 1H), 2.32-2.24 (m, 3H), 2.21-2.09 (m, 2H), 1.85-1.38 (m, 2H), 1.36-1.12 (m, 4H), 0.94-0.69 (m, 3H), 0.71-0.54 (m, 4H).

$^{13}$C NMR (101 MHz, CDCl$_3$) δ 173.98, 168.95, 162.54, 160.62, 159.01, 157.23, 151.09, 148.33, 137.43, 136.89, 135.19, 132.84, 130.57, 124.48, 123.84, 115.34, 113.32, 108.02, 61.63, 55.45, 51.49, 41.14, 35.16, 30.12, 28.89, 22.66, 21.11, 18.40, 17.66, 13.70, 8.32. HRMS (ESI): calculated for C$_{31}$H$_{38}$N$_7$O$_4$ [M+H]$^+$=572.2985; found 572.2980.

Example 5

Synthesis of (S)—N-(3-fluoropyridin-2-yl)-5-((R)-2-((N-hydroxyformamido)methyl)hexylcarbonyl)-5-azaspiro[2.4]heptane-6-amide

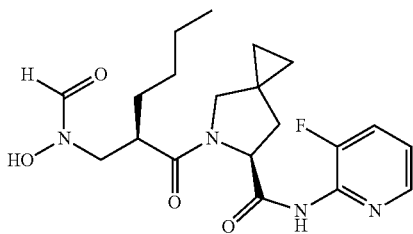 [SMILES: CCCC[C@H](CN(O)C=O)C(=O)N1CC2(CC2)C[C@H]1C(=O)Nc1ncccc1F]

Step 1: The procedure was the same as the Step 1 in the synthesis of the general formula (X1).

Step 2: The procedure was the same as the Step 2 in the synthesis of the general formula (X1) (1.7 g, white solid, 45% yield throught two steps).

$^1$H NMR (400 MHz, D$_2$O) δ 8.20 (d, J=5.5 Hz, 1H), 8.06 (t, J=9.0 Hz, 1H), 7.56-7.50 (m, 1H), 4.90-4.79 (m, 1H), 3.31 (s, 2H), 2.61-2.39 (m, 1H), 2.15 (dd, J=13.4, 6.1 Hz, 1H), 0.76-0.54 (m, 4H).

$^{13}$C NMR (101 MHz, D$_2$O) δ 169.94, 150.12 (d, J=255.5 Hz), 138.18, 137.92 (d, J=13.4 Hz), 130.12 (d, J=16.9 Hz), 123.10 (d, J=5.8 Hz), 60.39, 52.83, 37.21, 20.06, 9.96, 8.50.

Step 3: The procedure was the same as the Step 3 in the synthesis of the general formula (X2).

Step 4: The procedure was the same as the Step 4 in the synthesis of the general formula (X2). Yellow solid was obtained through column chromatography (DCM:MeOH=10:1), with a two-step yield of 37%.

LC-MS (ESI): [M+1]$^+$=406.70, t$_R$=2.35 min.

$^1$H NMR (400 MHz, CDCl$_3$) δ 8.40-8.15 (m, 1H), 8.01-7.79 (m, 1H), 7.65-7.35 (m, 1H), 7.33-7.00 (m, 1H), 5.05-4.66 (m, 1H), 4.30-3.64 (m, 2H), 3.62-3.21 (m, 2H), 3.05 (m, 1H), 2.78-1.90 (m, 2H), 1.84-1.40 (m, 2H), 1.41-1.14 (m, 4H), 1.00-0.51 (m, 7H).

$^{13}$C NMR (101 MHz, CDCl$_3$) δ 73.98, 168.98, 157.19, 150.39 (d, J=258.5 Hz), 143.63 (d, J=5.6 Hz), 140.45 (d, J=12.1 Hz), 123.73 (d, J=17.4 Hz), 121.04, 61.31, 55.35, 51.28, 40.97, 35.11, 30.08, 28.90, 22.67, 21.10, 13.85, 13.71, 8.13.

HRMS (ESI): calculated for C$_{20}$H$_{28}$FN$_4$O$_4$ [M+H]$^+$ =407.2110; found 407.2126.

Example 6

Synthesis of (S)-5-((R)-2-((N-hydroxyformamido)methyl)hexylcarbonyl)-N-(5-methylthiazol-2-yl)-5-azaspiro[2.4]heptane-6-amide

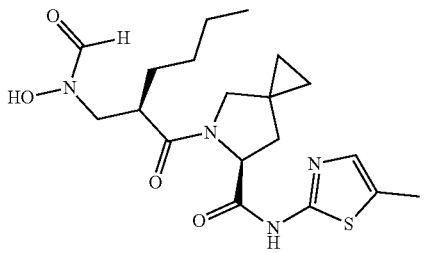 [SMILES: CCCC[C@H](CN(O)C=O)C(=O)N1CC2(CC2)C[C@H]1C(=O)Nc1ncc(C)s1]

Step 1: The procedure was the same as the Step 1 in the synthesis of the general formula (X1).

Step 2: The procedure was the same as the Step 2 in the synthesis of the formula (X1) (680 mg, white solid, two-step yield of 100%).

$^1$H NMR (400 MHz, D$_2$O) δ 7.24 (s, 1H), 4.77 (dd, J=8.9, 6.5 Hz, 1H), 3.24 (s, 2H), 2.38 (dd, J=13.4, 9.1 Hz, 1H), 2.28 (s, 3H), 2.05 (dd, J=13.4, 6.3 Hz, 1H), 0.72-0.45 (m, 4H).

$^{13}$C NMR (101 MHz, D$_2$O) δ 168.01, 159.21, 129.86, 124.06, 60.16, 52.75, 36.68, 20.02, 11.03, 9.78, 8.73.

Step 3: The procedure was the same as the Step 3 in the synthesis of the general formula (X2).

Step 4: The procedure was the same as the Step 4 in the synthesis of the general formula (X2). Off-white solid was obtained through column chromatography (DCM:MeOH=10:1), with a two-step yield of 42%.

LC-MS (ESI): [M+1]$^+$=408.72, t$_R$=2.67 min.

$^1$H NMR (400 MHz, CDCl$_3$) δ 7.70 (s, 1H), 7.64 (s, 1H), 4.68 (d, J=7.6 Hz, 1H), 4.24 (t, J=10.5 Hz, 1H), 3.93 (d, J=11.5 Hz, 1H), 3.41 (d, J=12.5 Hz, 1H), 3.02 (d, J=11.5 Hz, 1H), 2.62 (s, 1H), 2.40 (dd, J=12.2, 8.0 Hz, 1H), 2.30 (s, 3H), 2.13 (d, J=12.3 Hz, 1H), 1.73-1.41 (m, 2H), 1.39-1.16 (m, 4H), 0.88 (t, J=6.6 Hz, 3H), 0.72-0.50 (m, 2H), 0.30-0.05 (m, 2H).

$^{13}$C NMR (101 MHz, CDCl$_3$) δ 174.04, 171.12, 158.73, 153.63, 135.01, 126.02, 61.53, 53.99, 53.60, 43.50, 39.25, 31.29, 29.17, 22.90, 19.23, 13.84, 13.26, 11.72, 5.98.

HRMS (ESI): calculated for C$_{19}$H$_{29}$N$_4$O$_4$S [M+H]$^+$ =409.1910; found 409.1922.

Example 7

Synthesis of (S)-5-((R)-2-((N-hydroxyformamido)methyl)hexylcarbonyl)-N-(3-(pyridin-3-yl)phenyl)-5-5-azaspiro[2.4]heptane-6-amide

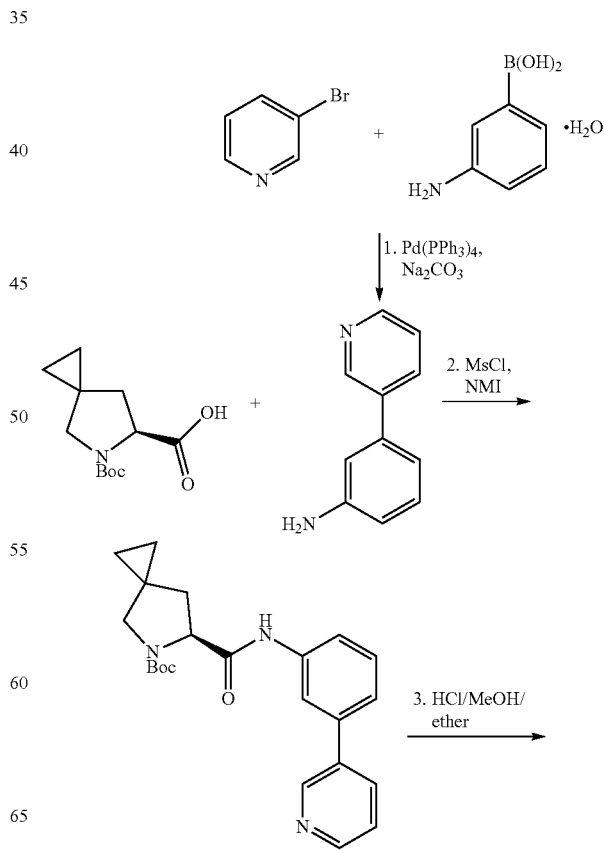

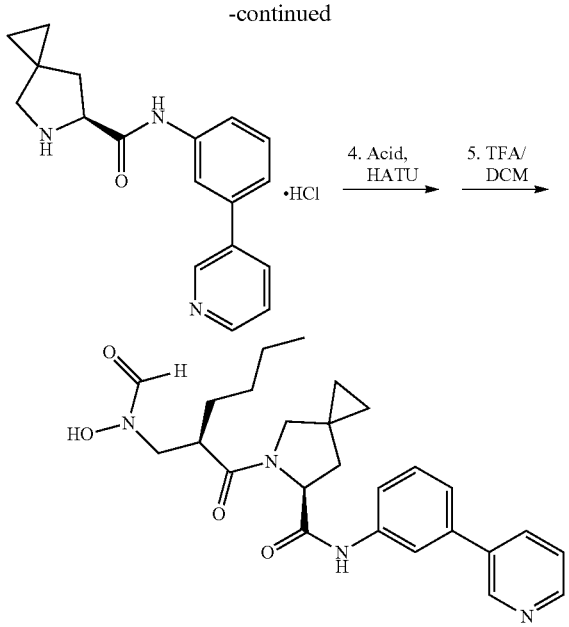

Step 1: To a mixture of 3-bromopyridine (2.37 g, 15 mmol), 3-aminophenylboronic acid monohydrate (2.32 g, 15 mmol) and Pd(PPh$_3$)$_4$ (520 mg, 0.45 mmol), ethylene glycol dimethyl ether (30 mL) and water (15 mL) were added. The whole reaction system was replaced three times with nitrogen, and heated to reflux for 12 h. After the completion of the reaction, the mixture was cooled, and the solvent was removed. The residue was then went through column chromatography (DCM/EA: 5/1 to 2/1) to give a yellow semi-solid product (680 mg, 27% yield).

$^1$H NMR (400 MHz, CDCl$_3$) δ 8.81 (d, J=2.0 Hz, 1H), 8.57 (J=4.7 Hz, 1H), 7.84 (d, J=7.9 Hz, 1H), 7.34 (dd, J=7.9, 4.8 Hz, 1H), 7.26 (dd, J=8.8, 6.8 Hz, 1H), 6.96 (d, J=7.6 Hz, 1H), 6.88 (s, 1H), 6.73 (dd, J=8.0, 2.1 Hz, 1H), 3.83 (brs, 2H).

$^{13}$C NMR (101 MHz, CDCl$_3$) δ 148.31, 148.21, 147.06, 138.96, 136.88, 134.41, 130.05, 123.52, 117.48, 114.82, 113.63.

Step 2: The procedure was the same as the Step 1 in the synthesis of the general formula (X1). (S)-5-(tert-butyl)-5-azaspiro[2.4]heptane-6-carboxylic acid (950 mg, 3.94 mmol) was dissolved in DMF (5 mL), then NMI (0.7 mL, 8.67 mmol) was added. After cooling to 0° C., MsCl (451 mg, 3.94 mmol) was added dropwise, and the mixture was stirred for 15 min. Then 3-(pyridin-3-yl)aniline (670 mg, 3.94 mmol) was added. The progress of the reaction was monitored by TLC. After the completion of the reaction, the reaction mixture was diluted with ethyl acetate, and washed with 10% citric acid queous solution. The aqueous phase was extracted with ethyl acetate (2×20 mL). The organic phases were combined, and washed with saturated sodium carbonate aqueous solution and saturated sodium chloride successively. The crude product was obtained by concentration under reduced pressure through rotary evaporation.

Step 3: In 10 mL of ethyl ether was dissolved the crude product, and then was added 5 mL of HCl/MeOH solution (5 M). The mixture was stirred at room temperature overnight. The precipitate was collected and dried to give a brown solid (900 mg, two-step yield of 69%).

$^1$H NMR (400 MHz, D$_2$O) δ 8.54 (s, 1H), 8.35 (d, J=5.7 Hz, 1H), 8.31 (d, J=8.2 Hz, 1H), 7.69 (dd, J=7.8, 6.2 Hz, 1H), 7.38 (s, 1H), 7.15-7.05 (m, 2H), 4.44-4.38 (m, 1H), 3.08 (d, J=11.4 Hz, 1H), 3.03 (d, J=11.4 Hz, 1H), 2.16 (dd, J=13.2, 8.8 Hz, 1H), 1.80 (dd, J=13.3, 6.6 Hz, 1H), 0.54-0.29 (m, 4H).

$^{13}$C NMR (101 MHz, D$_2$O) δ 167.95, 144.27, 139.57, 138.97, 138.77, 137.47, 133.84, 130.50, 127.45, 124.14, 122.41, 119.26, 60.25, 52.75, 37.49, 20.24, 9.55, 9.03.

Step 4: The procedure was the same as the Step 3 in the synthesis of the general formula (X2).

Step 5: The procedure was the same as the Step 4 in the synthesis of the general formula (X2). Off-white solid was obtained through column chromatography (DCM:MeOH=10:1), with a two-step yield of 19%.

LC-MS (ESI): [M+1]$^+$=464.85, $t_R$=2.33 min.

$^1$H NMR (400 MHz, CDCl$_3$) δ 9.68 (s, 1H), 8.65 (d, J=1.6 Hz, 1H), 8.43 (d, J=3.8 Hz, 1H), 7.84-7.71 (m, 2H), 7.66 (s, 1H), 7.39 (d, J=7.6 Hz, 1H), 7.23 (dd, J=7.8, 4.7 Hz, 1H), 7.16 (t, J=7.9 Hz, 1H), 7.05 (d, J=7.6 Hz, 1H), 4.81 (t, 5.2 Hz), 3.92-3.58 (m, 2H), 3.56-3.32 (m, 2H), 3.15-3.02 (m, 1H), 2.14-1.98 (m, 1H), 1.72-1.34 (m, 2H), 1.36-1.11 (m, 4H), 0.80-0.64 (m, 3H), 0.63-0.48 (s, 4H).

$^{13}$C NMR (101 MHz, CDCl$_3$) δ 173.77, 169.72, 157.20, 147.90, 147.76, 139.28, 137.91, 136.55, 134.85, 129.36, 123.65, 122.19, 119.26, 118.10, 61.64, 55.59, 51.68, 50.53, 41.17, 36.00, 30.12, 28.87, 22.66, 21.12, 13.73, 9.05.

HRMS (ESI): calculated for C$_{26}$H$_{32}$N$_4$O$_4$Na [M+Na]$^+$ =487.2321; found 487.2318.

Example 8

Synthesis of (S)-5-((R)-2-((N-hydroxyamido)methyl)hexylcarbonyl)-N-(3-(2-pyridylamino)phenyl)-5-azaspiro[2.4]heptane-6-amide

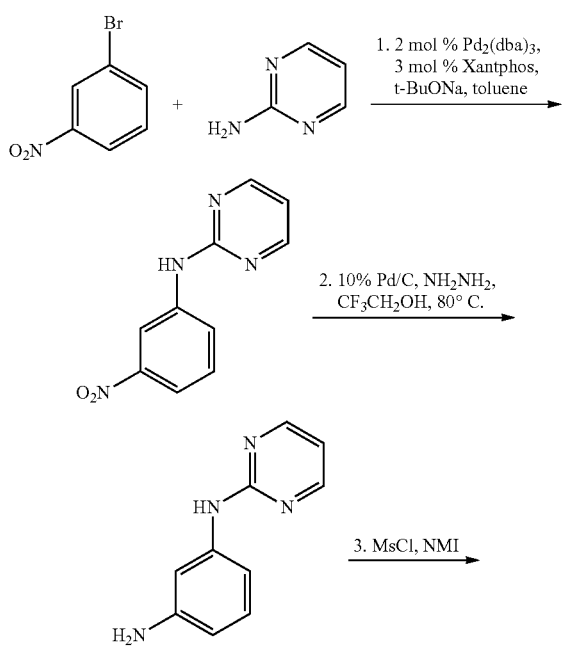

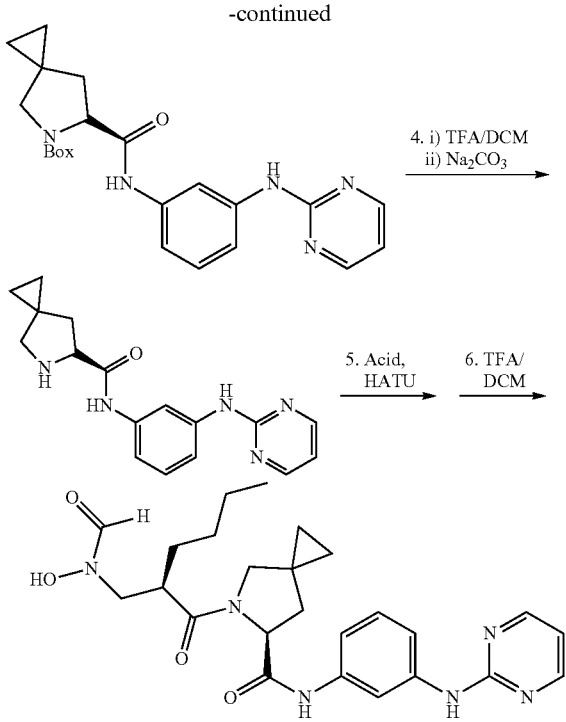

Step 1: Xantphos (347 mg, 3 mol %), Pd$_2$(dba)$_3$ (366 mg, 2 mol %), 2-aminopyrimidine (1.92 g, 20 mmol) and sodium tert-butoxide (1.92 g, 20 mmol) were added to a reaction flask. The system was replaced three times with nitrogen. A solution of 3-bromo-1-nitrobenzene (4.04 g, 20 mmol) in toluene (20 mL) was added to the reaction. The mixture was heated to 95° C. for reacting for 18 hours. The reaction mixture was cooled and filtered through celite (the filter cake was washed with 200 mL of toluene to remove impurities, and then eluted with a mixture of 10% MeOH in ethyl acetate (500 mL)) to yield a crude product. Yellow solid product was obtained through pulping with ethyl acetate (2.6 g, 60% yield).

LC-MS (ESI): [M+1]$^+$=217.00, $t_R$=2.45 min.

$^1$H NMR (400 MHz, CDCl$_3$) δ 8.74 (s, 1H), 8.51 (d, J=4.7 Hz, 2H), 7.90-7.83 (m, 2H), 7.70 (s, 1H), 7.47 (t, J=8.1 Hz, 1H), 6.85 (t, J=4.7 Hz, 1H).

$^{13}$C NMR (101 MHz, CDCl$_3$) δ 159.57, 158.12, 148.86, 140.74, 129.51, 124.47, 116.94, 113.74, 113.61.

Step 2: The trifluoroethanol solution (20 mL) containing 10% Pd/C (50 mg), N-(3-nitrophenyl)pyrimidin-2-amine (1.3 g, 6.0 mmol) and 80% hydrazine hydrate (1 mL) was heated to 80° C. for reacting for 5 hours. After the completion of the reaction, the catalyst was filtered off, and the obtained filtrate was concentrated to give a product (1.1 g, 100% yield).

LC-MS (ESI): [M+1]$^+$=186.76, $t_R$=1.17 min.

$^1$H NMR (400 MHz, CDCl$_3$) δ 8.39 (d, J=4.8 Hz, 2H), 7.86 (brs, 1H), 7.16 (t, J=1.9 Hz, 1H), 7.09 (t, J=8.0 Hz, 1H), 6.94-6.83 (m, 1H), 6.66 (t, J=4.8 Hz, 1H), 6.37 (dd, J=7.9, 2.0 Hz, 1H), 3.67 (brs, 2H).

$^{13}$C NMR (101 MHz, CDCl$_3$) δ 160.29, 157.96, 147.26, 140.52, 129.71, 112.29, 109.95, 109.75, 106.28.

Step 3: The procedure was the same as the Step 1 in the synthesis of the general formula (X1). (S)-5-(tert-butoxycarbonyl)-5-azaspiro[2.4]heptane-6-carboxylic acid (965 mg, 4.0 mmol) was dissolved in DMF (8 mL), and then NMI (722 mg, 8.8 mmol) was added. The mixture was cooled to 0° C., and then added with MsCl (460 mg, 4.0 mmol) dropwise. The mixture was then stirred for 15 min. After that, N-(2-pyrimidinyl)benzene-1,3-diamine (745 mg, 4.0 mmol) was added. After the completion of the reaction, the mixture was diluted with ethyl acetate, and washed with 10% citric acid aqueous solution. The organic phase was extracted with ethyl acetate (2×50 mL). The combined organic phases was washed with saturated sodium carbonate and sodium chloride. Yellow solid was obtained through concentration under reduced pressure.

Step 4: The solid was dissolved in 2:1 DCM/TFA (8 mL/4 mL) solution, and allowed to react at room temperature for 1 hour. After the completion of the reaction, the mixture was added with a few drops of water and neutralized with solid sodium carbonate. After drying over anhydrous Na$_2$SO$_4$, insoluble solid was filtered off, and the filtrate was concentrated to give free alkali (500 mg, two-step yield of 50%).

$^1$H NMR (400 MHz, CDCl$_3$) δ 9.81 (brs, 1H), 8.34 (m, 2H), 8.00-7.90 (m, 1H), 7.72-7.50 (m, 1H), 7.46-7.25 (m, 1H), 7.26-7.09 (m, 1H), 6.71-6.47 (m, 1H), 4.19-3.76 (m, 1H), 3.16-2.85 (m, 1H), 2.91-2.52 (m, 1H), 2.28-2.05 (m, 1H), 2.00-1.77 (m, 1H), 0.82-0.21 (m, 4H).

$^{13}$C NMR (101 MHz, CDCl$_3$) δ 172.97, 160.08, 157.97, 140.14, 138.46, 129.36, 115.19, 113.66, 112.55, 110.39, 61.41, 54.68, 39.12, 22.40, 10.88, 9.55.

Step 5: The procedure was the same as the Step 3 in the synthesis of the general formula (X2).

Step 6: The procedure was the same as the Step 4 in the synthesis of the general formula (X2). Off-white solid was obtained through column chromatography (DCM:MeOH=10:1), with a two-step yield of 37%.

$^1$H NMR (400 MHz, CDCl$_3$) δ 9.81 (brs, 1H), 8.34 (m, 2H), 8.00-7.90 (m, 1H), 7.72-7.50 (m, 1H), 7.46-7.25 (m, 1H), 7.26-7.09 (m, 1H), 6.71-6.47 (m, 1H), 4.19-3.76 (m, 1H), 3.16-2.85 (m, 1H), 2.91-2.52 (m, 1H), 2.28-2.05 (m, 1H), 2.00-1.77 (m, 1H), 0.82-0.21 (m, 4H).

$^{13}$C NMR (101 MHz, CDCl$_3$) δ 172.97, 160.08, 157.97, 140.14, 138.46, 129.36, 115.19, 113.66, 112.55, 110.39, 61.41, 54.68, 39.12, 22.40, 10.88, 9.55.

LC-MS (ESI): [M+1]$^+$=481.36, $t_R$=2.35 min.

$^1$H NMR (400 MHz, CDCl$_3$) δ 9.30 (s, 1H), 8.37 (d, J=4.7 Hz, 2H), 8.12 (s, 1H), 7.87 (s, 1H), 7.77 (s, 1H), 7.47 (d, J=7.5 Hz, 1H), 7.24-7.07 (m, 2H), 6.66 (t, J=4.8 Hz, 1H), 5.06-4.47 (m, 1H), 4.08-3.56 (m, 2H), 3.55-3.30 (m, 2H), 3.23-2.76 (m, 1H), 2.29-1.88 (m, 2H), 1.75-1.41 (m, 2H), 1.40-1.19 (m, 4H), 1.05-0.70 (m, 3H), 0.74-0.45 (m, 4H).

$^{13}$C NMR (101 MHz, CDCl$_3$) δ 173.78, 169.36, 159.92, 157.93, 157.38, 139.95, 138.86, 129.19, 115.26, 114.12, 112.26, 110.94, 61.66, 55.48, 51.60, 41.14, 35.63, 30.14, 28.92, 22.68, 21.13, 13.78, 12.95, 8.90.

HRMS (ESI): calculated for C$_{25}$H$_{33}$N$_6$O$_4$ [M+1]$^+$ =481.2563; found 481.2566.

Example 9

Synthesis of (S)-5-((R)-2-((N-hydroxyformamido)methyl)hexylcarbonyl)-N-(4-(3-pyridyl)pyrimidin-2-yl)-5-azaspiro[2.4]heptane-6-amide

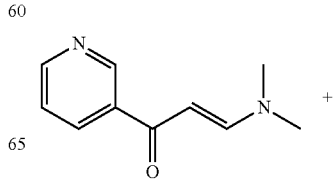

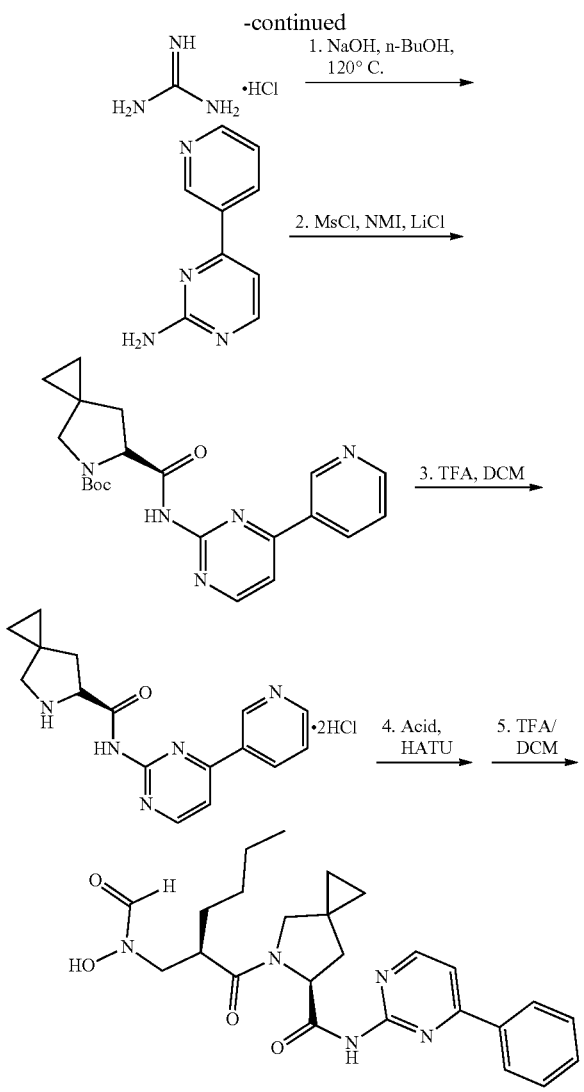

Step 1: 3-dimethylamino-1-(3-pyridyl)-2-propenyl-1-one (1.76 g, 10.0 mmol) was suspended in n-butanol (20 mL), followed by the addition of guanidine hydrochloride (1.15 g, 12.0 mmol) and NaOH (480 mg, 12.0 mmol). The mixture was heated to 120° C. for reacting overnight. The precipitated solid was collected and washed with water (50 mL), followed by vacuum drying to give a light yellow crystal (1.51 g, 88% yield).

$^1$H NMR (400 MHz, DMSO) δ 9.23 (d, J=2.0 Hz, 1H), 8.67 (dd, J=4.7, 1.3 Hz, 1H), 8.38 (dt, J=8.0, 1.8 Hz, 1H), 8.36 (d, J=5.1 Hz, 1H), 7.52 (dd, J=8.0, 4.8 Hz, 1H), 7.20 (d, J=5.1 Hz, 1H), 6.81 (s, 2H).

$^{13}$C NMR (101 MHz, DMSO) δ 163.78, 161.53, 159.36, 151.11, 147.93, 134.11, 132.44, 123.72, 105.99.

Step 2: (S)-5-(tert-butoxycarbonyl)-5-azaspiro[2.4]heptane-6-carboxylic acid (2.0 g, 8.5 mmol) was dissolved in DMF (20 mL), followed by the addition of NMI (2.1 g, 25.5 mmol). The mixture was cooled to 0° C., into which MsCl (978 mg, 8.5 mmol) was added dropwise. The mixture was stirred for 15 min. Then 4-(3-pyridyl)pyrimidin-2-amine (980 mg, 5.7 mmol) and lithium chloride (721 mg, 17.0 mmol) were added. After reacting at room temperature for 48 hours under stirring, the reaction mixture was diluted with ethyl acetate, and washed with 10% citric acid aqueous solution. The aqueous phase was extracted with ethyl acetate (2×50 mL). The organic phase was washed with saturated sodium carbonate and sodium chloride. After concentrating under reduced pressure, pure product (1.0 g, 44% yield) was obtained by the purification of the crude product through silica gel column (DCM/MeOH=100/1-30/1).

$^1$H NMR (400 MHz, CDCl$_3$) (two rotamers were observed) δ 9.98 (brs, 0.5H), 9.28 (d, J=2.0 Hz, 1H), 9.06 (brs, 0.5H), 8.83-8.70 (m, 2H), 8.42 (d, J=8.0 Hz, 1H), 7.56-7.40 (m, 2H), 4.96-4.60 (m, 1H), 3.65-3.50 (m, 1H), 3.45-3.10 m, 1H), 2.50-2.25 (m, 1H), 2.20-2.05 (m, 1H), 1.51 (s, 9H), 0.78-0.54 (s, 4H).

Step 3: The obtained product was separated and dissolved in 10 mL of diethyl ether, followed by adding with 5 mL of HCl/MeOH (5M). The mixture was stirred for reacting overnight at room temperature. The precipitate was collected and dried to give a white solid (584 mg, 63% yield).

$^1$H NMR (400 MHz, D$_2$O) δ 9.09 (s, 1H), 8.65 (d, J=5.4 Hz, 1H), 8.62 (d, J=3.9 Hz, 1H), 8.47 (d, J=8.1 Hz, 1H), 7.68 (d, J=5.3 Hz, 1H), 7.61 (dd, J=8.0, 5.2 Hz, 1H), 4.79-4.76 (m, 1H), 3.42-3.27 (m, 2H), 2.50 (dd, J=13.4, 9.0 Hz, 1H), 2.15 (dd, J=13.2, 6.1 Hz, 1H), 0.94-0.60 (m, 4H).

$^{13}$C NMR (101 MHz, D$_2$O) δ 162.87, 159.54, 149.77, 146.43, 138.16, 137.44, 134.43, 132.17, 124.98, 114.33, 60.83, 52.79, 37.24, 26.35, 20.10, 18.44, 9.85, 8.57.

Step 4: The procedure was the same as the Step 3 in the synthesis of the general formula (X2).

Step 5: The procedure was the same as the Step 4 in the synthesis of the general formula (X2). Off-white solid was obtained through column chromatography (DCM:MeOH=10:1), with a two-step yield of 19%.

LC-MS (ESI): [M+1]$^+$=466.74, t$_R$=2.20 min.

$^1$H NMR (400 MHz, CDCl$_3$) δ 9.91 (s, 1H), 9.37-9.08 (m, 1H), 8.85-8.53 (m, 1H), 8.37 (s, 2H), 7.87 (s, 1H), 7.65-7.12 (m, 2H), 5.55-5.00 (m, 1H), 4.14-3.64 (m, 2H), 3.55-3.10 (m, 2H), 3.02-2.58 (m, 1H), 2.45-2.10 (m, 2H), 2.05-1.46 (m, 2H), 1.45-1.10 (m, 4H), 1.00-0.30 (m, 7H).

$^{13}$C NMR (101 MHz, CDCl$_3$) δ 180.38, 173.69, 162.72, 159.32, 157.91, 157.76, 151.70, 148.31, 134.89, 131.89, 123.83, 111.79, 61.70, 55.39, 51.35, 42.84, 41.02, 35.71, 30.09, 28.87, 22.71, 21.02, 13.75, 8.41.

HRMS (ESI): calculated for C$_{24}$H$_{31}$N$_6$O$_4$ [M+1]$^+$=467.2407; found 467.2399.

Example 10

Synthesis of N—((R)-2-((S)-6-(1H-benzimidazol-2-yl)-5-azaspiro[2.4]heptane-5-carbonyl)hexyl)-N-hydroxyformamide

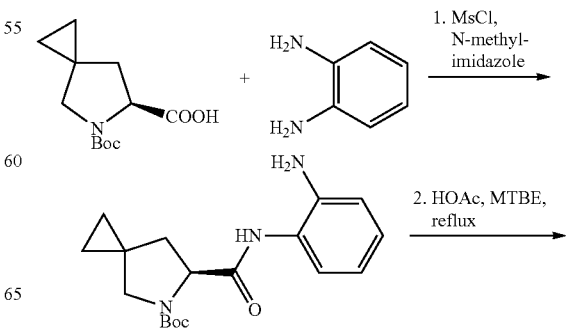

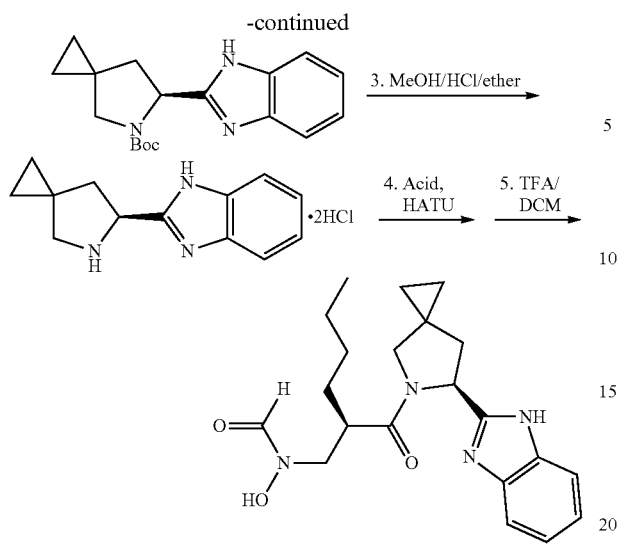

Step 1: (S)-5-(tert-butoxycarbonyl)-5-azaspiro[2.4]heptane-6-carboxylic acid (2.4 g, 10 mmol) was added into a flask. Then N,N-dimethylformamide DMF (25 mL) was added and dissolved, followed by the addition of N-methylimidazole NMI (1.8 mL, 22 mmol) under ice bath, and dropwise addition of methanesulfonyl chloride (0.78 mL, 10 mmol). The mixture was stirred at 0° C. for 15 minutes. Then o-phenylenediamine (2.8 g, 20 mmol) was added. The reaction system was stirred at room temperature for 6 hours. After the completion of the reaction, the reaction solution was diluted with ethyl acetate, and the organic phase was washed three times with 10% citric acid aqueous solution to remove excess o-phenylenediamine. Finally, the organic phase was dried and concentrated to give a crude pink solid, which was foamed solid.

Step 2: The obtained solid was dissolved in 20 mL of methyl tert-butyl ether, and 4 mL of acetic acid was added. The solution was heated to reflux for 3 hours. After the completion of the reaction, saturated $Na_2CO_3$ solution was added to neutralize pH to neutral. The organic layer was isolated and concentrated to give a product of ring closing reaction.

Step 3: In 20 mL of diethyl ether was dissolved the oily ring closing product, and was added 5 M HCl/MeOH solution (10 mL). The mixture was stirred for overnight. The precipitated white solid was collected and dried in vacuo to give 1.3 g of product, with the total yield reaching 45% through three-step synthesis process.

$^1$H NMR (400 MHz, $D_2O$) δ 7.67-7.58 (m, 2H), 7.49-7.39 (m, 2H), 5.41 (t, J=8.6 Hz, 1H), 3.55-3.46 (m, 1H), 3.25-3.15 (m, 1H), 2.68-2.57 (m, 1H), 2.39-2.28 (m, 1H), 0.85-0.60 (m, 4H).

$^{13}$C NMR (101 MHz, $D_2O$) δ 144.90, 130.95, 127.05, 114.21, 36.52, 20.20, 11.92, 7.25.

Step 4: The procedure was the same as the Step 3 in the synthesis of the general formula (X2).

Step 5: The procedure was the same as the Step 4 in the synthesis of the general formula (X2). A semi-solid was obtained by column chromatography (DCM:MeOH=10:1), with a two-step yield of 32%.

LC-MS (ESI): [M+1]$^+$=385.06, $t_R$=1.51 min.

$^1$H NMR (400 MHz, $CDCl_3$) δ 12.10 (s, 1H), 8.30-7.79 (m, 1H), 7.74-7.34 (m, 2H), 7.29-7.16 (m, 2H), 5.58-5.42 (m, 1H), 4.21-4.01 (m, 1H), 3.97-3.87 (m, 1H), 3.84-3.68 (m, 1H), 3.55-3.40 (m, 1H), 3.31-3.11 (m, 1H), 2.76-2.57 (m, 1H), 2.40-2.07 (m, 1H), 1.70-1.45 (m, 2H), 1.39-1.22 (m, 4H), 0.94-0.83 (m, 3H), 0.73-0.49 (m, 2H), 0.32-0.15 (m, 2H).

$^{13}$C NMR (101 MHz, $CDCl_3$) δ 174.59, 161.90, 154.44, 123.20, 122.92, 56.75, 53.81, 48.09, 43.15, 41.24, 29.69, 29.11, 22.86, 19.00, 14.11, 13.86, 5.90.

HRMS (ESI): calculated for $C_{21}H_{28}N_4O_3$ [M+1]$^+$=385.2060; found 385.2013.

Example 11

Synthesis of N-hydroxy-N—((R)-2-((S)-6-(3-(pyridin-3-yl)-1,2,4-oxadiazol-5-yl)-5-azaspiro[2.4]heptane-5-carbonyl)hexyl)carboxamide

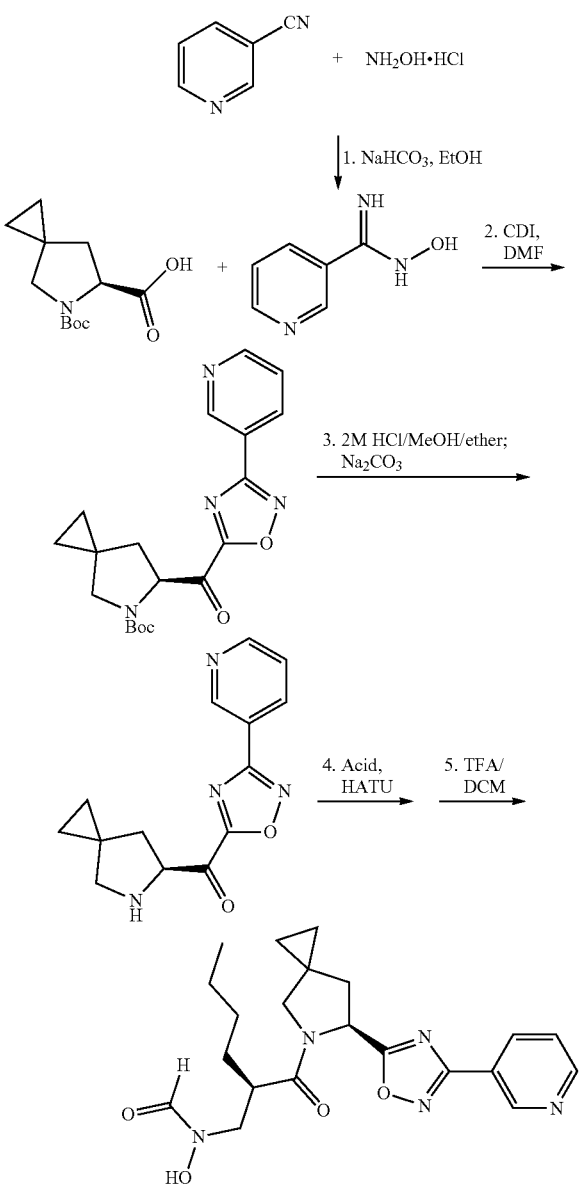

Step 1: To a solution of 3-cyanopyridine (5.2 g, 50 mmol) dissolved in 50 mL of ethyl alcohol, hydroxylamine hydrochloride (4.2 g, 60 mmol), $NaHCO_3$ (5.0 g, 60 mmol) and water (3 mL) were added. The mixture was heated to reflux for 12 hours, followed by the addition of anhydrous Na₂SO₄. The mixture was filtrated, and then diluted with diethyl ether (50 mL) to precipitate a white crystal (6.6 g, 96% yield).

¹H NMR (400 MHz, DMSO) δ 9.87 (s, 1H), 8.87 (d, J=2.1 Hz, 1H), 8.57 (dd, J=4.8, 1.5 Hz, 1H), 8.03 (dt, J=8.0, 1.9 Hz, 1H), 7.41 (dd, J=8.0, 4.8 Hz, 1H), 6.01 (s, 2H).

¹³C NMR (101 MHz, DMSO) δ 149.72, 148.92, 146.56, 132.82, 129.01, 123.22.

Step 2: (S)-5-(tert-butoxycarbonyl)-5-azaspiro[2.4]heptane-6-carboxylic acid (2.49 g, 10.3 mmol) was dissolved in DMF (25 mL), and then N,N'-carbonyldiimidazole (CDI, 1.75 g, 10.3 mmol) was added. After stirring at room temperature for 8 hours, the mixture was added with N-hydroxy-(3-pyridyl)formamidine (1.41 g, 10.3 mmol), and then another equivalent of CDI (1.75 g, 10.3 mmol). The mixture was heated to 90° C. under a nitrogen atmosphere for reacting for 12 hours. As the reaction mixture was cooled, it was diluted with ethyl acetate (50 mL), washed with 10% citric acid aqueous solution, and extracted with ethyl acetate (50 mL). The collected organic phase was washed with 10% citric acid aqueous solution, saturated sodium bicarbonate aqueous solution and sodium chloride successively, and then was concentrated to obtain crude product (3.2 g, 84% yield).

LC-MS (ESI): [M+1]⁺=343.19, $t_R$=2.32 min.

¹H NMR (400 MHz, CDCl₃) (two rotomers were observed) δ 9.35-9.29 (m, 1H), 8.79-8.73 (m, 1H), 8.56-8.27 (m, 1H), 7.55-7.37 (m, 1H), 5.38-5.20 (m, 1H), 3.58-3.38 (m, 2H), 2.64-2.41 (m, 1H), 1.47 (s, 4H), 1.32 (s, 5H), 0.81-0.47 (m, 4H).

Step 3: To a solution of the oily substance (2.1 g, 5.67 mmol) dissolved in 10 mL of diethyl ether, 10 mL of HCl/MeOH solution (5 M) was added. The reaction was processed overnight under stirring. The reaction liquid was added with a small amount of water, and sodium carbonate solid was added to neutralized acid. After the bubbles disappeared, solid was filtered off, and the filtrate was concentrated to dry to give free alkali (1.2 g, 80% yield).

LC-MS (ESI): [M+1]⁺=243.89, $t_R$=1.13 min.

¹H NMR (400 MHz, CDCl₃) δ 9.33 (d, J=1.7 Hz, 1H), 8.74 (dd, J=4.8, 1.4 Hz, 1H), 8.37 (dt, J=7.9, 1.7 Hz, 1H), 7.43 (dd, J=7.9, 4.9 Hz, 1H), 4.76 (dd, J=7.7, 6.1 Hz, 1H), 3.14 (d, J=10.0 Hz, 1H), 3.01 (d, J=10.0 Hz, 1H), 2.30 (dd, J=12.6, 7.8 Hz, 1H), 2.19 (dd, J=12.6, 5.9 Hz, 1H), 0.65 (s, 4H).

¹³C NMR (101 MHz, CDCl₃) δ 182.26, 166.29, 151.99, 148.70, 134.72, 123.59, 123.11, 55.07, 54.87, 40.42, 22.22, 11.54, 11.38.

Step 4: The procedure was the same as the Step 3 in the synthesis of the general formula (X2).

Step 5: The procedure was the same as the Step 4 in the synthesis of the general formula (X2). Colourless oily substance was obtained by column chromatography (DCM:MeOH=10:1), with a two-step yield of 33%.

LC-MS (ESI): [M+1]⁺=413.69, $t_R$=2.33 min.

¹H NMR (400 MHz, CDCl₃) δ 9.20 (d, J=1.2 Hz, 1H), 8.79-8.57 (dd, J=3.6 Hz, 1H), 8.28 (dd, J=6.2, 1.6 Hz, 1H), 7.73 (s, 1H), 7.35 (dd, J=7.9, 4.9 Hz, 1H), 5.51 (dd, J=8.1, 4.0 Hz, 1H), 3.94-3.67 (m, 2H), 3.66-3.47 (m, 1H), 3.42-3.26 (m, 1H), 3.16-2.82 (m, 1H), 2.40 (dd, J=12.9, 8.2 Hz, 1H), 2.03-1.78 (m, 1H), 1.64-1.39 (m, 2H), 1.37-1.16 (m, 4H), 0.84 (t, J=7.0 Hz, 3H), 0.74-0.42 (m, 4H).

¹³C NMR (101 MHz, CDCl₃) δ 180.16, 172.50, 166.33, 157.43, 151.85, 148.55, 134.84, 123.63, 123.28, 54.52, 54.10, 51.66, 40.86, 38.86, 29.99, 28.76, 22.77, 21.17, 13.87, 12.48, 8.58.

HRMS (ESI): calculated for C₂₁H₂₈N₅O₄ [M+1]⁺=414.2141; found 414.2146.

Example 12

Synthesis of N-hydroxy-N—((R)-2-((S)-6-(5-(pyridin-2-yl)-1,3,4-oxadiazol-2-yl)-5-azaspiro[2.4]heptane-5-carbonyl)hexyl)carboxamide

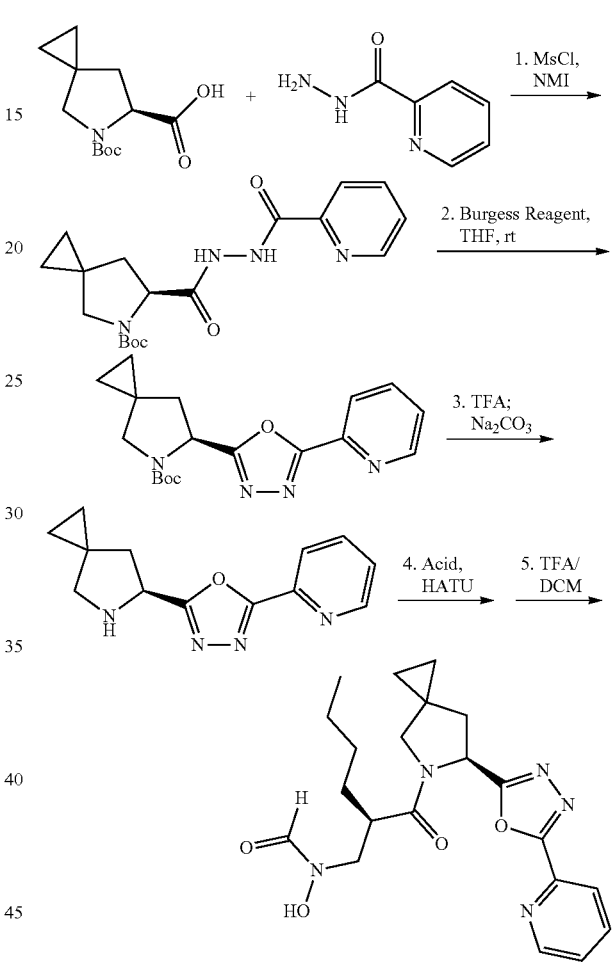

Step 1: To a solution of (S)-5-(tert-butoxycarbonyl)-5-azaspiro[2.4]heptane-6-carboxylic acid (1.0 g, 4.14 mmol) dissolved in DMF (10 mL), NMI (1.8 mL, 22 mmol) was added. and MsCl (475 mg, 4.14 mmol) was added dropwise at 0° C. The mixture was stirred for 15 min. Then 2-pyridineformylhydrazide (569 mg, 4.14 mmol) was added. After reacting for 6 hours, the reaction mixture was diluted with ethyl acetate and washed with 10% citric acid aqueous solution. The aqueous phase was extracted with ethyl acetate (2×50 mL). The combined organic phases was washed with saturated sodium bicarbonate aqueous solution and sodium chloride successively, and then was concentrated to yield a colourless oily product (1.5 g, 100% yield).

LC-MS (ESI): [M+1]⁺=361.09, $t_R$=2.10 min.

Step 2: To a solution of the oily substance (1.5 g, 4.14 mmol) dissolved in THF (20 mmol), Burgess regent (2.9 g, 10.35 mmol) was added in batches. The mixture was stirred at room temperature for 3 hours. After the completion of the reaction, the reaction solution was diluted with diethyl ether, and then was added with water. The separated organic phase was washed twice with saturated sodium chloride, dried over anhydrous Na$_2$SO$_4$, filtered and concentrated to give a crude product (1.4 g, 100% yield).

LC-MS (ESI): [M+1]$^+$=343.13, $t_R$=2.53 min.

Step 3: The oily substance (1.4 g, 4.13 mmol) was dissolved in 2:1 DCM/TFA (6 mL/3 mL), and the mixture was stirred at room temperature for 1 hour. After the completion of the reaction, the reaction solution was added with a few drops of water, and neutralized with sodium carbonate solid, followed by drying over anhydrous sodium sulfate, filtering to remove insoluble material. The filtrate was concentrated to dry to give free alkali (1.0 g, 100% yield).

LC-MS (ESI): [M+1]$^+$=243.08, $t_R$=1.34 min.

$^1$H NMR (400 MHz, CDCl$_3$) δ 8.78 (d, J=4.6 Hz, 1H), 8.25 (d, J=7.9 Hz, 1H), 7.89 (td, J=7.8, 1.6 Hz, 1H), 7.46 (ddd, J=7.6, 4.9, 0.9 Hz, 1H), 4.78 (dd, J=7.4, 6.4 Hz, 1H), 3.14 (d, J=10.0 Hz, 1H), 2.98 (d, J=10.0 Hz, 1H), 2.37-2.15 (m, 2H), 0.74-0.52 (m, 4H).

$^{13}$C NMR (101 MHz, CDCl$_3$) δ 169.54, 164.25, 150.23, 143.57, 137.21, 125.79, 123.10, 54.79, 54.16, 39.87, 22.21, 11.59, 11.32.

Step 4: The procedure was the same as the Step 3 in the synthesis of the general formula (X2).

Step 5: The procedure was the same as the Step 4 in the synthesis of the general formula (X2). Colourless oily substance was obtained by column chromatography (DCM:MeOH=10:1), with a two-step yield of 25%.

LC-MS (ESI): [M+1]$^+$=413.76, $t_R$=2.47 min.

$^1$H NMR (400 MHz, CDCl$_3$) δ 8.45 (d, J=4.0 Hz, 1H), 8.19-7.85 (m, 1H), 7.75-7.25 (m, 2H), 7.22-7.00 (m, 1H), 5.50-4.92 (m, 1H), 4.04-3.44 (m, 2H), 3.42-2.96 (m, 2H), 2.98-2.60 (m, 1H), 2.58-2.07 (m, 1H), 2.06-1.57 (m, 1H), 1.45-1.17 (m, 2H), 1.16-0.92 (m, 4H), 0.72-0.53 (m, 3H), 0.47-0.16 (m, 4H).

$^{13}$C NMR (101 MHz, CDCl$_3$) δ 175.27, 172.56, 167.63, 166.49, 164.20, 163.74, 161.76, 157.54, 150.29, 150.15, 143.56, 141.99, 138.38, 137.11, 126.75, 125.69, 123.48, 123.00, 54.59, 53.87, 53.56, 53.09, 51.04, 47.66, 41.11, 40.99, 38.69, 38.64, 30.74, 30.04, 29.13, 28.77, 22.91, 22.74, 21.02, 19.07, 15.71, 13.86, 13.78, 12.41, 8.83, 8.68, 6.36.

HRMS (ESI): calculated for C$_{21}$H$_{28}$N$_5$O$_4$ [M+1]$^+$=414.2141; found 414.2157.

Example 13

Synthesis of N—((R)-2-((S)-6-([1,2,4]triazole[4,3-a]pyridin-3-yl)-5-azaspiro[2.4]heptane-5-carbonyl)hexyl)-N-hydroxyamide

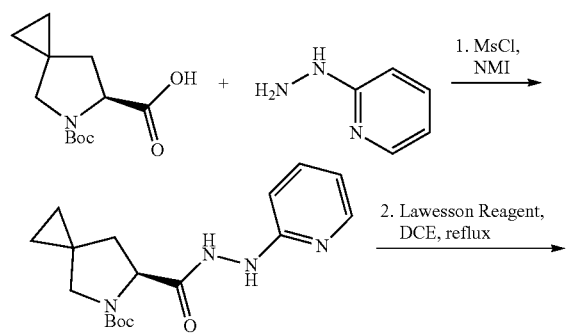

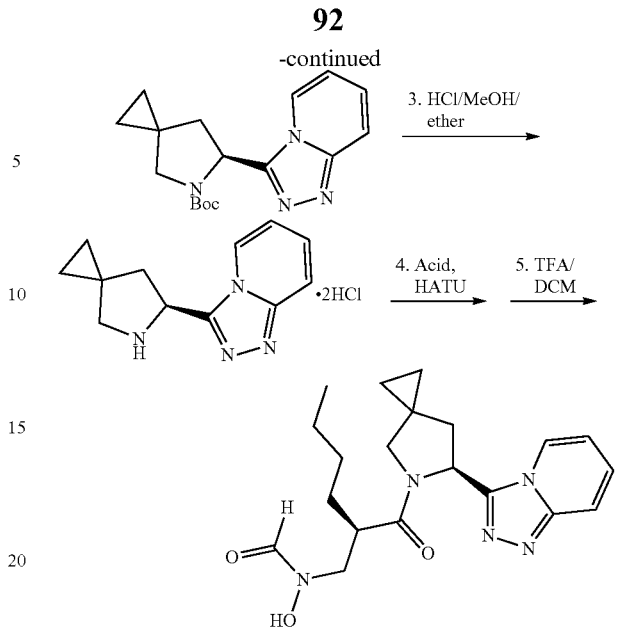

Step 1: To a solution of (S)-5-(tert-butoxycarbonyl)-5-azaspiro[2.4]heptane-6-carboxylic acid (2.4 g, 10 mmol) dissolved in DMF (25 mL), NMI (1.8 mL, 22 mmol) was added. After cooling to 0° C., MsCl (0.78 mL, 10 mmol) was added dropwise. The mixture was stirred for 15 min, followed by adding with 2-pyridine hydrazine (1.1 g, 10 mmol). After reacting for 6 hours, the reaction mixture was diluted with ethyl acetate, added with water (100 mL), and extracted with ethyl acetate (2×50 mL). The organic phase was washed with saturated sodium chloride, followed by rotary evaporation to give a crude product. Off-white solid was obtained through pulping with diethyl ether (2.35 g, 71% yield).

LC-MS (ESI): [M+1]$^+$=332.86, $t_R$=1.74 min.

Step 2: To a solution of the solid (2.35 g, 7.1 mmol) dissolved in dichloroethane DCE (30 mL), Lawesson reagent (2.9 g, 7.1 mmol) was added. The mixture was heated to 80° C. under nitrogen atmosphere for reacting for 3 hours. After the completion of the reaction, the reaction solution was washed with saturated sodium carbonate solution, 10% citric acid aqueous solution, and saturated sodium chloride successively. The concentrated reaction mixture was purified through silica gel column (eluent: DCM/MeOH=50/1 to 30/1) to give a colourless oily substance (2.0 g, 90% yield).

LC-MS (ESI): [M+1]$^+$=315.22, $t_R$=2.19 min.

Step 3: To a solution of the oily substance (2.0 g, 6.36 mmol) dissolved in 20 mL of diethyl ether, 10 mL of HCl/MeOH solution (5 M) was added. The mixture was stirred at room temperature overnight. The collected resulting precipitate was dried to give a white solid (820 mg, 45% yield).

LC-MS (ESI): [M+1]$^+$=214.79, $t_R$=1.17 min.

$^1$H NMR (400 MHz, D$_2$O) δ 8.68 (d, J=11.1 Hz, 1H), 8.10-7.95 (m, 2H), 7.55 (d, J=3.7 Hz, 1H), 5.76 (dd, J=6.8 Hz, 1H), 3.61 (d, J=11.4 Hz, 1H), 3.48 (d, J=11.4 Hz, 1H), 2.70-2.53 (m, 2H), 0.95-0.71 (m, 4H).

$^{13}$C NMR (101 MHz, D$_2$O) δ 145.96, 143.31, 137.51, 124.76, 118.88, 111.94, 52.75, 52.36, 36.80, 19.88, 10.36, 9.63.

Step 4: The procedure was the same as the Step 3 in the synthesis of the general formula (X2).

Step 5: The procedure was the same as the Step 4 in the synthesis of the general formula (X2). Colourless oily substance was obtained through column chromatography (DCM:MeOH=10:1), with a two-step yield of 23%.

LC-MS (ESI): [M+1]⁺=386.03, $t_R$=2.00 min.

¹H NMR (400 MHz, CDCl₃) δ 8.49-8.35 (m, 1H), 7.85 (s, 1H), 7.77-7.71 (m, 1H), 7.28-7.21 (m, 1H), 7.03-6.76 (m, 1H), 5.79-5.39 (m, 1H), 4.04-3.77 (m, 2H), 3.78-3.37 (m, 2H), 3.24-2.90 (m, 1H), 2.87-2.59 (m, 1H), 2.40-2.16 (m, 1H), 1.62-1.30 (m, 2H), 1.22-0.99 (m, 4H), 0.93-0.47 (m, 7H).

¹³C NMR (101 MHz, CDCl₃) δ 172.93, 157.21, 149.67, 147.19, 127.20, 123.46, 116.01, 113.42, 54.93, 51.40, 48.34, 41.16, 39.13, 29.91, 28.77, 22.45, 21.39, 13.72, 11.62, 10.36.

HRMS (ESI): calculated for $C_{20}H_{27}N_5O_3Na$ [M+Na]⁺ =408.2012; found 408.2029.

Example 14

Synthesis of (S)-5-((R)-2-((N-hydroxyformamido) methyl)hexylcarbonyl)-N-(4-morpholinophenyl)-5-azaspiro[2.4]heptane-6-amide

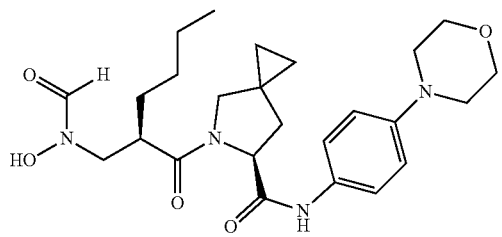 [SMILES: CCCC[C@H](CN(O)C=O)C(=O)N1CC2(CC2)C[C@H]1C(=O)Nc1ccc(N2CCOCC2)cc1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=302.05, $t_R$=1.06 min.

¹H NMR (400 MHz, DMSO) δ 10.82 (s, 1H), 7.52 (d, J=8.8 Hz, 2H), 6.93 (d, J=8.8 Hz, 2H), 4.55 (t, J=7.9 Hz, 1H), 3.78-3.67 (m, 4H), 3.19 (dd, J=37.9, 11.2 Hz, 2H), 3.08-3.02 (m, 4H), 2.33 (dd, J=12.9, 8.2 Hz, 1H), 2.01 (dd, J=12.9, 7.6 Hz, 1H), 0.78-0.53 (m, 4H).

¹³C NMR (101 MHz, DMSO) δ 165.87, 147.72, 130.32, 120.50, 115.35, 66.04, 59.59, 51.66, 48.71, 37.81, 20.35, 10.34, 9.73.

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 30%.

LC-MS (ESI): [M+1]⁺=473.29, $t_R$=1.79 min.

¹H NMR (400 MHz, CDCl₃) δ 7.80 (s, 1H), 7.40 (d, J=7.4 Hz, 2H), 6.82 (d, J=6.8 Hz, 2H), 4.83 (s, 1H), 4.17-3.64 (m, 7H), 3.53-3.27 (m, 2H), 3.08 (s, 5H), 2.16 (s, 2H), 1.28 (d, J=20.0 Hz, 6H), 0.84 (s, 3H), 0.80-0.50 (m, 4H).

Example 15

Synthesis of (S)-5-((R)-2-((N-hydroxyformamido) methyl)hexylcarbonyl)-N-(pyrazin-2-yl)-5-azaspiro [2.4]heptane-6-amide

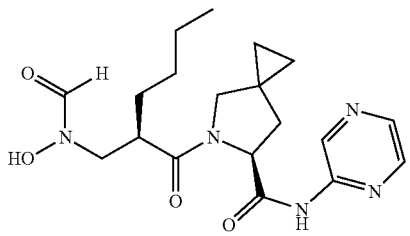 [SMILES: CCCC[C@H](CN(O)C=O)C(=O)N1CC2(CC2)C[C@H]1C(=O)Nc1cnccn1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=219.14, $t_R$=0.57 min.

¹H NMR (400 MHz, D₂O) δ 8.98 (d, J=96.9 Hz, 1H), 8.31 (t, J=81.8 Hz, 2H), 4.66-4.49 (m, 1H), 3.26-2.81 (m, 2H), 2.29-1.62 (m, 2H), 0.63-0.09 (m, 4H).

¹³C NMR (101 MHz, D₂O) δ 148.55, 144.82, 137.12, 133.80, 60.43, 52.76, 37.11, 20.13, 9.77, 8.95, 8.64.

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 26%.

LC-MS (ESI): [M+1]⁺=390.19, $t_R$=1.56 min.

¹H NMR (400 MHz, CDCl₃) δ8.48-8.12 (m, 3H), 7.82 (s, 1H), 5.31 (s, 1H), 4.96 (s 1H), 3.89 (d, J=9.2 Hz, 1H), 3.76-2.54 (m, 4H), 2.30-2.20 (m, 1H), 1.77-1.28 (m, 7H), 0.86 (s, 3H), 0.81-0.58 (m, 4H).

Example 16

Synthesis of (S)-5-((R)-2-((N-hydroxyformamido) methyl)hexanoyl)-N-(pyrimidin-4-yl)-5-spiro[2.4] heptane-6-carboxamide

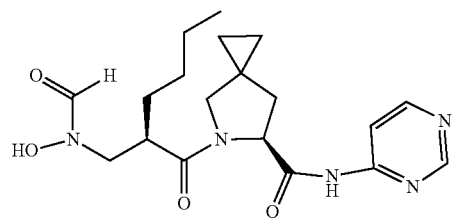 [SMILES: CCCC[C@H](CN(O)C=O)C(=O)N1CC2(CC2)C[C@H]1C(=O)Nc1ccncn1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=219.14, $t_R$=0.43 min.

¹H NMR (400 MHz, D₂O) δ 9.08 (s, 1H), 8.78 (d, J=6.8 Hz, 1H), 8.42 (t, J=31.2 Hz, 1H), 4.82 (dd, J=8.7, 6.4 Hz, 1H), 3.50-3.15 (m, 2H), 2.57-2.00 (m, 2H), 0.88-0.58 (m, 4H).

$^{13}$C NMR (101 MHz, D$_2$O) δ 169.77, 152.74, 150.17, 111.15, 60.98, 52.82, 36.76, 20.08, 9.91, 8.50.

Step 3: The procedure was the same as the Step 3 in the synthesis of the general formula (X2).

Step 4: The procedure was the same as the Step 4 in the synthesis of the formula (X2). White solid was obtained through chromatography (DCM:MeOH=10:1), with a two-step yield of 28%.

LC-MS (ESI): [M+1]$^+$=390.19, $t_R$=1.76 min.

$^1$H NMR (400 MHz, CDCl$_3$) δ 9.84 (d, J=23.5 Hz, 2H), 9.05-6.75 (m, 4H), 4.97 (t, J=36.3 Hz, 1H), 4.27-2.60 (m, 5H), 1.58-0.98 (m, 8H), 0.97-0.30 (m, 7H).

Example 17

Synthesis of (S)-5-((R)-2-((N-hydroxyformamido) methyl)hexylcarbonyl)-N-(isoxazol-5-yl)-5-azaspiro [2.4]heptane-6-amide

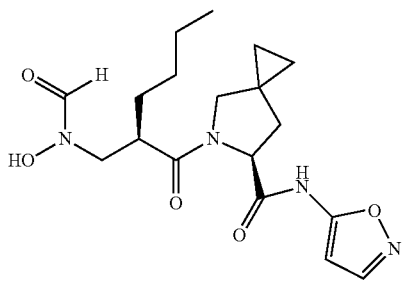 [SMILES: CCCC[C@H](CN(O)C=O)C(=O)N1CC2(CC2)C[C@H]1C(=O)Nc1ccno1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=208.11, $t_R$=0.57 min.

$^1$H NMR (400 MHz, DMSO) δ 10.66 (s, 1H), 9.01 (s, 1H), 8.51 (d, J=1.6 Hz, 1H), 6.29 (d, J=1.6 Hz, 1H), 4.98-4.32 (m, 1H), 3.29-2.98 (m, 2H), 2.45-1.87 (m, 2H), 0.85-0.47 (m, 4H).

$^{13}$C NMR (101 MHz, DMSO) δ 165.75, 160.13, 152.15, 88.25, 59.47, 51.64, 37.35, 20.12, 10.27, 9.78

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 27%.

LC-MS (ESI): [M+1]$^+$=379.17, $t_R$=1.88 min.

$^1$H NMR (400 MHz, CDCl$_3$) δ 8.14 (s, 1H), 7.78 (d, J=23.1 Hz, 1H), 6.38 (d, J=41.7 Hz, 1H), 5.03-4.72 (m, 1H), 3.97-3.79 (m, 2H), 3.54-2.85 (m, 3H), 2.11 (d, J=12.2 Hz, 1H), 1.74-1.17 (m, 7H), 0.88 (s, 3H), 0.78-0.60 (m, 4H).

Example 18

Synthesis of (S)-5-((R)-3-cyclopentyl-2-4N-hydroxyformamido)methyl)hexanoyl)-N-cyclopropyl-5-azaspiro[2.4]heptane-6-carboxamide

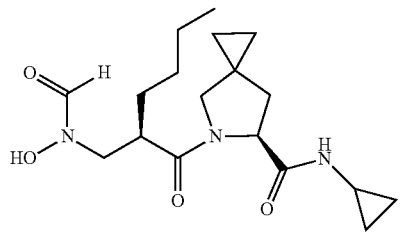 [SMILES: CCCC[C@H](CN(O)C=O)C(=O)N1CC2(CC2)C[C@H]1C(=O)NC1CC1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=182.98, =0.55 min $^1$H NMR (400 MHz, CDCl$_3$) δ 7.82 (s, 1H), 3.93 (dd, J=8.7, 5.2 Hz, 1H), 3.00-2.95 (m, 1H), 2.89 (s, 1H), 2.77-2.71 (m, 2H), 2.24-1.78 (m, 2H), 0.97-0.25 (m, 8H). $^{13}$C NMR (101 MHz, CDCl$_3$) δ 175.92, 60.94, 54.70, 39.27, 22.37, 22.09, 11.00, 9.48, 6.30, 6.27.

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 28%.

LC-MS (ESI): [M+1]$^+$=352.14, $t_R$=1.46 min $^1$H NMR (400 MHz, CDCl$_3$) δ 8.35 (d, J=16.0 Hz, 1H), 8.02-7.48 (m, 1H), 7.10-6.43 (m, 1H), 4.84-4.32 (m, 1H), 4.02-3.80 (m, 1H), 3.77-3.41 (m, 2H), 3.18-3.02 (m, 1H), 3.01-2.38 (m, 2H), 2.27-1.90 (m, 2H), 1.45-1.05 (m, 6H), 0.99-0.78 (m, 4H), 0.76-0.35 (m, 7H).

Example 19

Synthesis of (S)-5-((R)-2-((N-hydroxyformamido) methyphexanoyl)-N-(4-methylthiazol-2-yl)-5-spiro [2.4]heptane-6-carboxamide

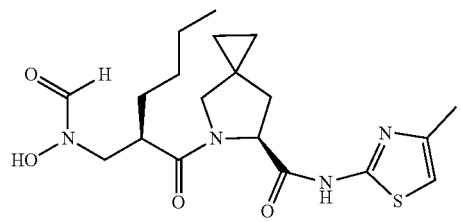 [SMILES: CCCC[C@H](CN(O)C=O)C(=O)N1CC2(CC2)C[C@H]1C(=O)Nc1nc(C)cs1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=237.60, $t_R$=0.66 min.

$^1$H NMR (400 MHz, DMSO) δ 9.09 (d, J=4.8 Hz, 1H), 6.89 (d, J=0.9 Hz, 1H), 4.92-4.46 (m, 1H), 3.42-2.98 (m, 2H), 2.48-1.85 (m, 5H), 0.88-0.41 (m, 4H).

$^{13}$C NMR (101 MHz, DMSO) δ 167.14, 157.01, 146.07, 108.59, 59.22, 51.52, 37.47, 20.13, 16.53, 10.22, 9.90.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 28%.

LC-MS (ESI): [M+1]$^+$=409.53, $t_R$=1.90 min.

$^1$H NMR (400 MHz, CDCl$_3$) δ 11.53 (s, 1H), 7.84 (S, 1H), 6.86 (s, 1H), 5.31 (s, 1H), 5.13-2.78 (m, 5H), 2.68-1.89 (m, 4H), 1.42 (dd, J=104.6, 66.9 Hz, 7H), 1.11-0.17 (m, 7H).

Example 20

Synthesis of (S)-5-((R)-3-cyclopropyl-2-((N-hydroxyformamido)methyl)propionyl)-N-(oxazol-2-yl)-5-azaspiro[2.4]heptane-6-carboxamide

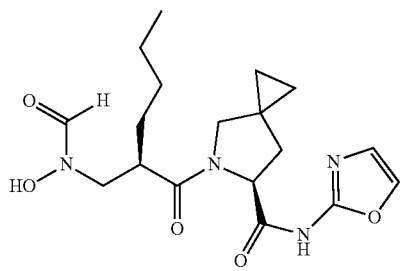 [SMILES: CCCC[C@H](CN(O)C=O)C(=O)N1CC2(CC2)C[C@H]1C(=O)Nc1ncco1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=208.32, $t_R$=0.36 min.

$^1$H NMR (400 MHz, DMSO) δ 10.77 (s, 1H), 7.95 (s, 1H), 7.19 (s, 1H), 4.64 (s, 1H), 3.19 (dd, J=12.2, 6.2 Hz, 2H), 2.38 (dd, J=12.9, 8.5 Hz, 1H), 2.01 (dd, J=12.8, 6.7 Hz, 1H), 0.67 (d, J=9.3 Hz, 4H).

$^{13}$C NMR (101 MHz, DMSO) δ 167.30, 152.62, 136.22, 125.77, 59.63, 51.56, 37.35, 20.08, 10.36, 9.71.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), the yield for the three steps was 22%.

LC-MS (ESI): [M+1]$^+$=379.52, $t_R$=1.83 min.

$^1$H NMR (400 MHz, CDCl$_3$) δ 7.57-7.39 (m, 1H), 7.02 (d, J=15.1 Hz, 1H), 5.32 (d, J=17.8 Hz, 1H), 3.77 (d, J=9.5 Hz, 2H), 3.48 (d, J=9.6 Hz, 1H), 3.12-2.89 (m, 2H), 2.83-2.63 (m, 2H), 1.75-1.13 (m, 11H), 0.96-0.60 (m, 4H).

Example 21

Synthesis of (S)-5-((R)-2-((N-hydroxyformamido)methyl)hexanoyl)-N-(5-methylisoxazol-3yl)-5-spiro[2.4]heptane-6-carboxamide

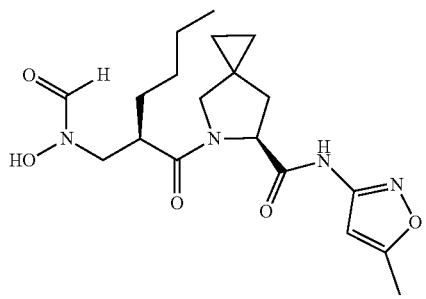 [SMILES: CCCC[C@H](CN(O)C=O)C(=O)N1CC2(CC2)C[C@H]1C(=O)Nc1cc(C)on1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=221.79, $t_R$=0.93 min.

$^1$H NMR (400 MHz, DMSO) δ 10.71 (s, 1H), 6.62 (s, 1H), 4.56 (s, 1H), 3.17 (d, J=11.9 Hz, 2H), 2.39 (s, 2H), 2.33 (dd, J=12.8, 8.5 Hz, 1H), 1.98 (dd, J=12.9, 7.0 Hz, 1H), 0.65 (d, J=14.3 Hz, 4H).

$^{13}$C NMR (101 MHz, DMSO) δ 170.05, 167.12, 157.36, 96.21, 59.47, 51.57, 37.49, 20.16, 12.10, 10.16, 9.88.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 32%.

LC-MS (ESI): [M+1]$^+$=393.22, $t_R$=1.69 min.

$^1$H NMR (400 MHz, DMSO) δ 11.00 (d, J=65.0 Hz, 1H), 8.45-7.49 (m, 1H), 6.61 (s, 1H), 4.66 (d, J=79.9 Hz, 1H), 3.73-3.15 (m, 5H), 2.43 (d, J=56.1 Hz, 5H), 2.20-1.69 (m, 2H), 1.66-1.02 (m, 6H), 0.86 (s, 3H), 0.58 (d, J=30.4 Hz, 4H).

Example 22

Synthesis of (S)-5-((R)-2-((N-hydroxyformamido)methyl)hexylcarbonyl)-N-(thiazol-2-yl)-5-azaspiro[2.4]heptane-6-amide

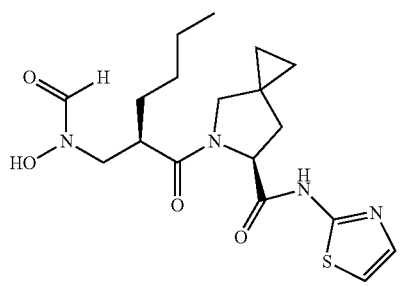 [SMILES: CCCC[C@H](CN(O)C=O)C(=O)N1CC2(CC2)C[C@H]1C(=O)Nc1nccs1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.38, $t_R$=0.92 min.

$^1$H NMR (400 MHz, DMSO) δ 10.84 (s, 1H), 7.53 (d, J=3.1 Hz, 1H), 7.34 (d, J=3.2 Hz, 1H), 4.79-4.59 (m, 1H), 3.21 (ddd, J=15.7, 10.7, 5.6 Hz, 2H), 2.37 (dd, J=12.9, 8.4 Hz, 1H), 2.03 (dd, J=13.0, 6.9 Hz, 1H), 0.77-0.57 (m, 4H).

$^{13}$C NMR (101 MHz, DMSO) δ 167.07, 157.46, 137.44, 114.41, 59.19, 51.59, 37.46, 20.16, 10.22, 9.94.

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 26%.

LC-MS (ESI): [M+1]$^+$=395.04, $t_R$=1.69 min.

$^1$H NMR (400 MHz, CDCl$_3$) δ 7.88 (s, 1H), 7.83 (s, 1H), 7.49-6.90 (m, 1H), 5.38 (d, J=29.3 Hz, 1H), 4.10 (dd, J=25.4, 13.2 Hz, 1H), 4.01 (d, J=8.4 Hz, 1H), 3.41 (dd, J=33.5, 11.2 Hz, 2H), 3.14 (s, 1H), 2.49-2.25 (m, 1H), 1.76 (d, J=5.9 Hz, 1H), 1.39-1.26 (m, 6H), 1.02-0.80 (m, 3H), 0.69-0.53 (m, 4H).

Example 23

Synthesis of (S)-5-((R)-2-((N-hydroxyformamido)methyl)hexanoyl)-N-(1,3,4-thiadiazol-2-yl)-5-azaspiro[2.4]heptane-6-carboxamide

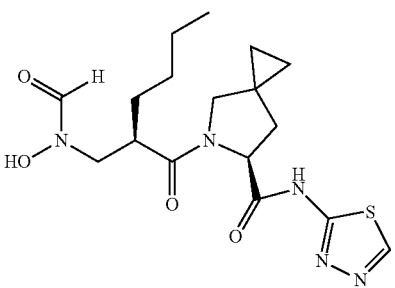 [SMILES: CCCC[C@H](CN(O)C=O)C(=O)N1CC2(CC2)C[C@H]1C(=O)Nc1nncs1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.87, $t_R$=0.63 min.

$^1$H NMR (400 MHz, DMSO) δ 10.85 (dd, J=52.8, 47.6 Hz, 1H), 9.13 (t, J=28.8 Hz, 1H), 4.96-4.50 (m, 1H), 3.47-2.92 (m, 2H), 2.46-1.89 (m, 2H), 1.15-0.23 (m, 4H).

$^{13}$C NMR (101 MHz, DMSO) δ 167.60, 158.24, 149.57, 59.31, 51.59, 37.35, 20.10, 10.31, 9.77.

Step 3: The procedure was the same as the Step 3 in the synthesis of the general formula (X2).

Step 4: The procedure was the same as the Step 4 in the synthesis of the general formula (X2). White solid was obtained through column chromatography (DCM: MeOH=10:1), with a two-step yield of 32%.

LC-MS (ESI): [M+1]$^+$=396.18, $t_R$=1.53 min.

$^1$H NMR (400 MHz, CDCl$_3$) δ 8.53 (s, 1H), 7.57 (s, 1H), 5.39-4.77 (s, 1H), 4.76-4.21 (m, 1H), 4.20-3.63 (m, 1H), 3.61-3.44 (m, 2H), 3.43-3.28 (m, 2H), 3.27-2.74 (m, 1H), 2.70-2.31 (m, 1H), 1.52-1.17 (m, 2H), 1.12-0.88 (m, 4H), 0.87-0.54 (m, 3H), 0.52-0.03 (m, 4H).

Example 24

Synthesis of N—((R)-2-((S)-6-(1-(2-(N,N-dimethypethyl)-1H-benzo[d]imidazol-2-yl)-5 azaspiro[2.4]heptane-5-carbonyl)hexanoyl)-N-hydroxyformamide

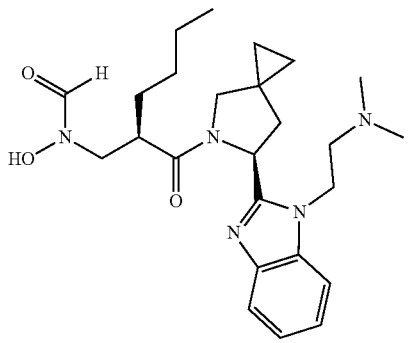 [SMILES: CCCC[C@H](CN(O)C=O)C(=O)N1CC2(CC2)C[C@H]1c1nc2ccccc2n1CCN(C)C]

Step 1: The procedure was the same as the Step 1 in Example 1.

Step 2: The procedure was the same as the Step 2 in Example 1.

Step 3: The procedure was the same as the Step 3 in Example 1.

Step 4: The product obtained in Step 3 was dissolved in THF, then 2.5-fold equivalents of NaH was added. 30 minutes later, 1.5-fold equivalents of dimethylaminochloroethane was added. The mixture was heated to reflux for reacting at 50° C. After the completion of the reaction, the reaction mixture was added with water and EA, extracted, and dried over anhydrous sodium sulfate for concentration, followed by pass through column to give a product.

LC-MS (ESI): [M+1]$^+$=285.17, $t_R$=0.57 min.

$^1$H NMR (400 MHz, D$_2$O) δ 7.80-7.61 (m, 2H), 7.58-7.39 (m, 2H), 5.50 (dd, J=9.1, 7.8 Hz, 1H), 4.93-4.76 (m, 2H), 3.69-3.22 (m, 4H), 2.96 (s, 6H), 2.67-2.22 (m, 2H), 0.88-0.63 (m, 4H).

$^{13}$C NMR (101 MHz, D$_2$O) δ 147.40, 135.78, 132.90, 126.31, 126.04, 117.18, 111.46, 54.06, 52.87, 52.72, 43.42, 39.33, 38.01, 20.39, 11.70, 7.58.

Step 5: The procedure was the same as the Step 3 in the synthesis of the general formula (X2).

Step 6: The procedure was the same as the Step 4 in the synthesis of the general formula (X2). White solid was obtained by lyophilization, with a two-step yield of 27%.

LC-MS (ESI): [M+1]$^+$=456.35, $t_R$=1.56 min.

$^1$H NMR (400 MHz, CDCl$_3$) δ 8.35 (s, 1H), 7.90-7.72 (m, 2H), 7.40-7.31 (m, 2H), 5.89-5.44 (m, 1H), 5.45-5.21 (m, 1H), 4.67-4.47 (m, 1H), 4.31-3.97 (m, 3H), 3.85-3.72 (m, 1H), 3.55-3.50 (m 1H), 3.46-3.30 (m, 1H), 2.92-2.66 (m, 8H), 2.16-1.89 (m, 1H), 1.87-1.62 (m, 1H), 1.46-1.34 (m, 2H), 1.32-1.19 (m, 5H), 0.84-0.71 (m, 3H), 0.69-049 (m, 4H).

Example 25

Synthesis of (S)-5-((R)-3-cyclopentyl-2-((N-hydroxyformamido)methyl)propionyl)-N-(4-morpholinophenyl)-5-spiro[2.4]heptane-6-carboxamide

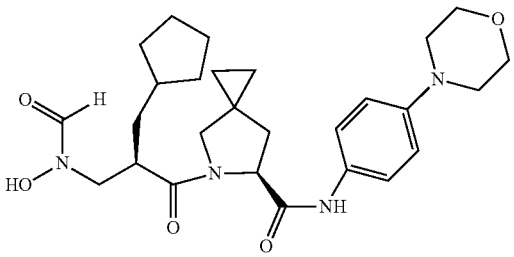 [SMILES: O=CN(O)C[C@@H](CC1CCCC1)C(=O)N1CC2(CC2)C[C@H]1C(=O)Nc1ccc(N2CCOCC2)cc1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=302.05, $t_R$=1.06 min.

$^1$H NMR (400 MHz, DMSO) δ 10.82 (s, 1H), 7.52 (d, J=8.8 Hz, 2H), 6.93 (d, J=8.8 Hz, 2H), 4.55 (t, J=7.9 Hz, 1H), 3.78-3.67 (m, 4H), 3.19 (dd, J=37.9, 11.2 Hz, 2H), 3.08-3.02 (m, 4H), 2.33 (dd, J=12.9, 8.2 Hz, 1H), 2.01 (dd, J=12.9, 7.6 Hz, 1H), 0.78-0.53 (m, 4H).

$^{13}$C NMR (101 MHz, DMSO) δ 165.87, 147.72, 130.32, 120.50, 115.35, 66.04, 59.59, 51.66, 48.71, 37.81, 20.35, 10.34, 9.73.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 35%.

LC-MS (ESI): [M+1]$^+$=499.31, $t_R$=1.76 min.

$^1$H NMR (400 MHz, CDCl$_3$) δ 7.84 (d, J=17.4 Hz, 1H), 7.54-7.32 (m, 2H), 6.87 (dd, J=13.7, 10.3 Hz, 2H), 5.05-4.71 (m, 1H), 4.22-3.80 (m, 8H), 3.23-3.00 (m, 5H), 2.06 (d, J=8.2 Hz, 4H), 1.90-1.37 (m, 10H), 0.75-0.40 (m, 3H).

Example 26

Synthesis of (S)-5-((R)-3-cyclopentyl-2-((N-hydroxyformamido)methyl)propylcarbonyl)-N-(pyrazin-2-yl)-5-azaspiro[2.4]heptane-6-amide

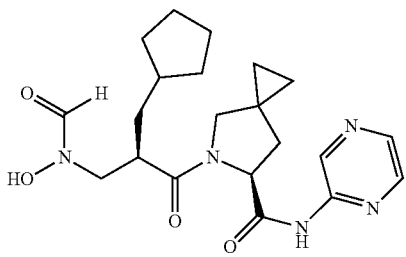 [SMILES: O=CN(O)C[C@@H](CC1CCCC1)C(=O)N1CC2(CC2)C[C@H]1C(=O)Nc1cnccn1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.57 min.

$^1$H NMR (400 MHz, D$_2$O) δ 8.98 (d, J=96.9 Hz, 1H), 8.31 (t, J=81.8 Hz, 2H), 4.66-4.49 (m, 1H), 3.26-2.81 (m, 2H), 2.29-1.62 (m, 2H), 0.63-0.09 (m, 4H).

$^{13}$C NMR (101 MHz, D$_2$O) δ 148.55, 144.82, 137.12, 133.80, 60.43, 52.76, 37.11, 20.13, 9.77, 8.95, 8.64.

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 32%.

LC-MS (ESI): [M+1]$^+$=416.21, $t_R$=1.65 min.

$^1$H NMR (400 MHz, CDCl$_3$) δ 9.48 (s, 1H), 8.42-8.25 (m, 1H), 8.22 (d, J=10.1 Hz, 1H), 7.76 (d, J=46.4 Hz, 1H), 4.93 (s, 1H), 4.03-3.50 (m, 3H), 3.36 (m, 1H), 3.19 (d, J=6.3 Hz, 1H), 2.23 (d, J=12.1 Hz, 1H), 2.02-1.19 (m, 12H), 0.83-0.59 (m, 4H).

Example 27

Synthesis of (S)-5-((R)-3-cyclopentyl-2-((N-hydroxyformamido)methyl)propionyl)-N-(pyrimidin-4-yl)-5-spiro[2.4]heptane-6-carboxamide

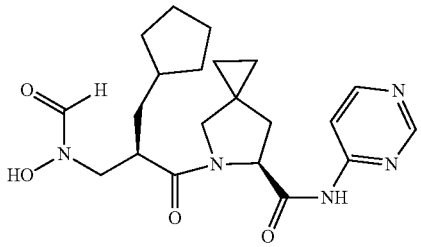 [SMILES: O=CN(O)C[C@@H](CC1CCCC1)C(=O)N1CC2(CC2)C[C@H]1C(=O)Nc1ccncn1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.43 min.

$^1$H NMR (400 MHz, D$_2$O) δ 9.08 (s, 1H), 8.78 (d, J=6.8 Hz, 1H), 8.42 (t, J=31.2 Hz, 1H), 4.82 (dd, J=8.7, 6.4 Hz, 1H), 3.50-3.15 (m, 2H), 2.57-2.00 (m, 2H), 0.88-0.58 (m, 4H).

$^{13}$C NMR (101 MHz, D$_2$O) δ 169.77, 152.74, 150.17, 111.15, 60.98, 52.82, 36.76, 20.08, 9.91, 8.50.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 28%.

LC-MS (ESI): [M+1]$^+$=416.21, $t_R$=1.26 min.

$^1$H NMR (400 MHz, CDCl$_3$) δ 11.25-9.16 (m, 2H), 9.12-8.46 (m, 2H), 8.42-7.54 (m, 2H), 5.30 (s, 1H), 4.15-3.60 (m, 2H), 3.23 (ddt, J=86.3, 30.4, 19.1 Hz, 3H), 2.36-1.19 (m, 13H), 0.80-0.24 (m, 4H).

Example 28

Synthesis of (S)-5-((R)-3-cyclopentyl-2-((N-hydroxyformamido)methyl)propionyl)-N-(5-fluoropyridin-2-yl)-5-azaspiro[2.4]heptane-6-carboxamide

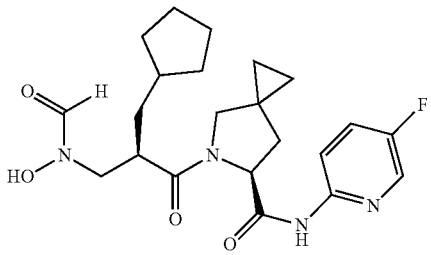 [SMILES: O=CN(O)C[C@@H](CC1CCCC1)C(=O)N1CC2(CC2)C[C@H]1C(=O)Nc1ccc(F)cn1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=236.09, $t_R$=1.00 min.

¹H NMR (400 MHz, D$_2$O) δ 8.25 (s, 1H), 7.98-7.87 (m, 1H), 7.64 (dd, J=9.2, 3.9 Hz, 1H), 4.75-4.73 (m, 1H), 3.48-3.21 (m, 2H), 2.44 (dd, J=13.3, 9.0 Hz, 1H), 2.13 (dd, J=13.3, 6.4 Hz, 1H), 0.79-0.54 (m, 4H).

¹³C NMR (101 MHz, D$_2$O) δ 169.10, 156.72 (d, ¹$J_{C-F}$=250.3 Hz), 144.96, 131.48 (d, ²$J_{C-F}$=30.9 Hz), 131.10 (d, ²$J_{C-F}$=18.7 Hz), 118.14 (d, ³$J_{C-F}$=6.2 Hz).

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 36%.

LC-MS (ESI): [M+1]⁺=434.22, $t_R$=1.95 min.

¹H NMR (400 MHz, CDCl$_3$) δ 10.33 (s, 1H), 8.64-7.75 (m, 2H), 7.61-6.95 (m, 1H), 4.71 (s, 1H), 4.11-3.74 (m, 1H), 3.71-3.49 (m, 1H), 3.46-2.87 (m, 2H), 2.86-2.50 (m, 1H), 2.47-2.07 (m, 1H), 1.72 (m, 6H), 1.53-1.17 (m, 4H), 1.16-0.76 (m, 2H), 0.73-0.21 (m, 3H).

Example 29

Synthesis of (S)-5-((R)-3-cyclopentylmethyl-2-((N-hydroxyformamido)methyl)propionyl)-N-(5-methylthiazol-2-yl)-5-spiro[2.4]heptane-6-carboxamide

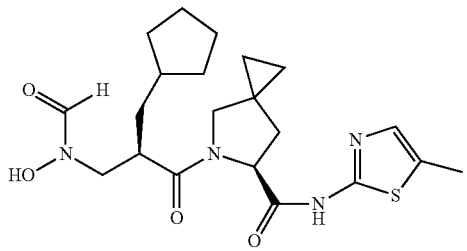 [SMILES: Cc1cnc(NC(=O)[C@@H]2CC3(CC3)CN2C(=O)[C@H](CC2CCCC2)CN(O)C=O)s1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=238.45, $t_R$=1.09 min.

¹H NMR (400 MHz, D$_2$O) δ 7.24 (s, 1H), 4.77 (dd, J=8.9, 6.5 Hz, 1H), 3.24 (s, 2H), 2.38 (dd, J=13.4, 9.1 Hz, 1H), 2.28 (s, 3H), 2.05 (dd, J=13.4, 6.3 Hz, 1H), 0.72-0.45 (m, 4H).

¹³C NMR (101 MHz, D$_2$O) δ 168.01, 159.21, 129.86, 124.06, 60.16, 52.75, 36.68, 20.02, 11.03, 9.78, 8.73.

Step 3: The procedure was the same as the Step 3 in the synthesis of the general formula (X2).

Step 4: The procedure was the same as the Step 4 in the synthesis of the formula (X2). White solid was obtained through chromatography (DCM:MeOH=10:1), with a two-step yield of 35%.

LC-MS (ESI): [M+1]⁺=435.24, $t_R$=1.93 min.

¹H NMR (400 MHz, CDCl$_3$) δ 13.75 (d, J=200.5 Hz, 1H), 10.54 (s, 1H), 7.67 (dd, J=86.8, 36.9 Hz, 1H), 7.15 (d, J=89.5 Hz, 1H), 5.67-4.98 (m, 1H), 4.85-2.78 (m, 5H), 2.58-1.06 (m, 17H), 0.96-0.31 (m, 4H).

Example 30

Synthesis of (S)-5-((R)-3-cyclopentyl-2-((N-hydroxyformamido)methyl)propionyl)-N-(3-fluoropyridin-2-yl)-5-spiro[2.4]heptane-6-carboxamide

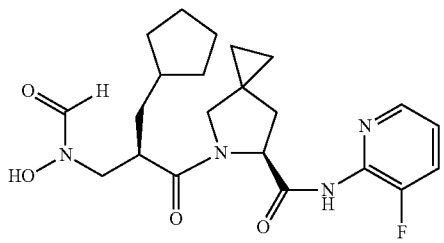 [SMILES: O=CN(O)C[C@@H](CC1CCCC1)C(=O)N1CC2(CC2)C[C@H]1C(=O)Nc1ncccc1F]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=235.90, $t_R$=0.60 min.

¹H NMR (400 MHz, D$_2$O) δ 8.20 (d, J=5.5 Hz, 1H), 8.06 (t, J=9.0 Hz, 1H), 7.56-7.50 (m, 1H), 4.90-4.79 (m, 1H), 3.31 (s, 2H), 2.61-2.39 (m, 1H), 2.15 (dd, J=13.4, 6.1 Hz, 1H), 0.76-0.54 (m, 4H).

¹³C NMR (101 MHz, D$_2$O) δ 169.94, 150.12 (d, J=255.5 Hz), 138.18, 137.92 (d, J=13.4 Hz), 130.12 (d, J=16.9 Hz), 123.10 (d, J=5.8 Hz), 60.39, 52.83, 37.21, 20.06, 9.96, 8.50.

Step 3: The procedure was the same as the Step 3 in the synthesis of the general formula (X2).

Step 4: The procedure was the same as the Step 4 in the synthesis of the formula (X2). White solid was obtained through chromatography (DCM:MeOH=10:1), with a two-step yield of 38%.

LC-MS (ESI): [M+1]⁺=433.22, $t_R$=1.65 min.

¹H NMR (400 MHz, CDCl$_3$) δ 9.40 (d, J=352.7 Hz, 1H), 8.24 (dd, J=55.9, 22.9 Hz, 1H), 7.88 (d, J=28.7 Hz, 1H), 7.65-7.41 (m, 1H), 7.39-7.03 (m, 1H), 5.24-4.45 (m, 1H), 4.24-3.99 (m, 1H), 3.97-3.58 (m, 2H), 2.88 (dddd, J=100.0, 91.1, 60.9, 42.5 Hz, 2H), 2.44-1.37 (m, 11H), 1.18-0.98 (m, 2H), 0.93-0.50 (m, 4H).

Example 31

Synthesis of (S)-5-((R)-3-cyclopentyl-2-((N-hydroxyformamido)methyl)propionyl)-N-(1H-pyrazol-3-yl)-5-azaspiro[2.4]heptane-6-carboxamide

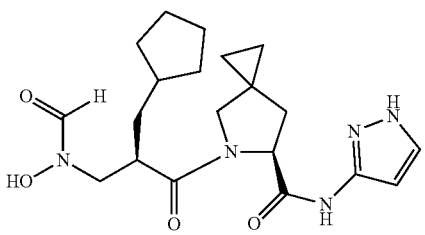 [SMILES: O=CN(O)C[C@@H](CC1CCCC1)C(=O)N1CC2(CC2)C[C@H]1C(=O)Nc1cc[nH]n1]

Step 1: The procedure was the same as the Step 1 in the synthesis of the general formula (X1).

Step 2: The procedure was the same as the Step 2 in the synthesis of the general formula (X1).

$^1$H NMR (400 MHz, DMSO) δ 11.53 (s, 1H), 10.66 (d, J=4.0 Hz, 1H), 8.94 (s, 1H), 7.79 (s, 1H), 6.52 (s, 1H), 4.70-4.51 (m, 1H), 3.31-3.24 (m, 1H), 3.21-3.15 (m, 1H), 2.43-2.27 (m, 1H), 2.01 (dd, J=12.7, 7.5 Hz, 1H), 0.80-0.57 (m, 4H).

$^{13}$C NMR (101 MHz, DMSO) δ 165.97, 144.77, 96.15, 55.94, 51.54, 37.61, 18.42, 10.22, 9.83.

Step 3: The procedure was the same as the Step 3 in the synthesis of the general formula (X2).

Step 4: The procedure was the same as the Step 4 in the synthesis of the formula (X2). White solid was obtained through column chromatography (DCM:MeOH=10:1), with a two-step yield of 31%.

LC-MS (ESI): [M+1]$^+$=404.56, $t_R$=1.16 min.

$^1$H NMR (400 MHz, CDCl$_3$) δ 11.40 (s, 1H), 11.18 (s, 1H), 7.92-7.62 (m, 1H), 7.58-7.36 (m, 1H), 6.92 (d, J=66.8 Hz, 1H), 5.51-5.21 (m, 1H), 4.60 (t, J=8.8 Hz, 1H), 4.36-3.96 (m, 2H), 3.81-3.66 (m, 2H), 2.81-2.44 (m, 2H), 2.36-1.62 (m, 11H), 0.76-0.19 (m, 4H).

Example 32

Synthesis of (S)-5-((R)-3-cyclopentyl-2-((N-hydroxyformamido)methyl)propionyl)-N-cyclopropyl-5-azaspiro[2.4]heptane-6-carboxamide

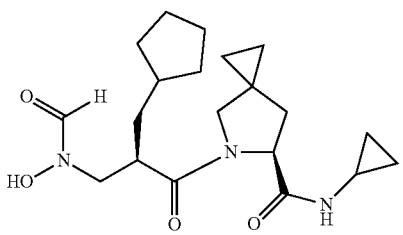 [SMILES: O=CN(O)C[C@@H](CC1CCCC1)C(=O)N1CC2(CC2)C[C@H]1C(=O)NC1CC1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=182.98, $t_R$=0.550 min $^1$H NMR (400 MHz, CDCl$_3$) δ 7.82 (s, 1H), 3.93 (dd, J=8.7, 5.2 Hz, 1H), 3.00-2.95 (m, 1H), 2.89 (s, 1H), 2.77-2.71 (m, 2H), 2.24-1.78 (m, 2H), 0.97-0.25 (m, 8H).

$^{13}$C NMR (101 MHz, CDCl$_3$) δ 175.92, 60.94, 54.70, 39.27, 22.37, 22.09, 11.00, 9.48, 6.30, 6.27.

Step 3: The procedure was the same as the Step 3 in the synthesis of the general formula (X2).

Step 4: The procedure was the same as the Step 4 in the synthesis of the formula (X2). White solid was obtained through column chromatography (DCM:MeOH=10:1), with a two-step yield of 27%.

LC-MS (ESI): [M+1]$^+$=378.16, $t_R$=1.60 min $^1$H NMR (400 MHz, CDCl$_3$) δ 8.67-7.74 (m, 1H), 7.27 (s, 1H), 7.05-6.31 (m, 1H), 4.89-4.33 (dt, J=14.5, 10.4 Hz, 1H), 4.04-3.79 (m, 1H), 3.79-3.64 (m, 1H), 3.61-3.13 (m, 2H), 3.13-2.84 (m, 1H), 2.84-2.57 (m, 1H), 2.29-2.05 (m, 1H), 1.88-1.54 (m, 6H), 1.53-1.04 (m, 4H), 1.03-0.18 (m, 7H).

Example 33

Synthesis of (S))-5-((R)-3-cyclopentylmethyl-2-((N-hydroxyformamido)methyl)propionyl)-N-(4-methyl-thiazol-2-yl)-5-spiro[2.4]heptane-6-carboxamide

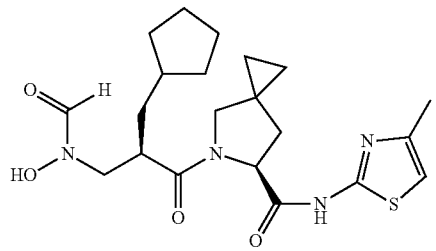 [SMILES: Cc1csc(NC(=O)[C@@H]2CC3(CC3)CN2C(=O)[C@H](CC2CCCC2)CN(O)C=O)n1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=237.60, $t_R$=0.66 min.

$^1$H NMR (400 MHz, DMSO) δ 9.09 (d, J=4.8 Hz, 1H), 6.89 (d, J=0.9 Hz, 1H), 4.92-4.46 (m, 1H), 3.42-2.98 (m, 2H), 2.48-1.85 (m, 5H), 0.88-0.41 (m, 4H).

$^{13}$C NMR (101 MHz, DMSO) δ 167.14, 157.01, 146.07, 108.59, 59.22, 51.52, 37.47, 20.13, 16.53, 10.22, 9.90.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 29%.

LC-MS (ESI): [M+1]$^+$=435.24, $t_R$=1.91 min.

$^1$H NMR (400 MHz, CDCl$_3$) δ 7.87 (s, 1H), 7.27 (s, 1H), 6.75-6.30 (m, 1H), 4.93 (s, 1H), 4.26-3.35 (m, 6H), 2.22-1.36 (m, 16H), 0.83-0.48 (m, 4H).

Example 34

Synthesis of 3-((S)-5-((R)-3-cyclopentyl-2-((N-hydroxylamino)methyl)propionyl-5-spiro[2.4]heptane-6-formyl)thiophene-2-carboxylic acid methyl ester

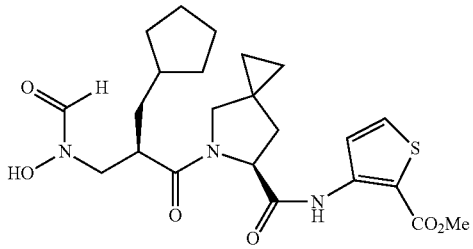 [SMILES: COC(=O)c1sccc1NC(=O)[C@@H]1CC2(CC2)CN1C(=O)[C@H](CC1CCCC1)CN(O)C=O]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=281.76, $t_R$=1.85 min.

$^1$H NMR (400 MHz, DMSO) δ 11.86 (s, 1H), 8.11 (d, J=5.4 Hz, 1H), 7.89 (d, J=5.4 Hz, 1H), 3.92 (dt, J=16.2, 8.1 Hz, 1H), 3.84 (s, 3H), 2.98 (d, J=10.0 Hz, 1H), 2.71 (d, J=10.0 Hz, 1H), 2.11 (dd, J=12.4, 9.0 Hz, 1H), 1.80 (dd, J=12.4, 4.4 Hz, 1H), 0.63-0.33 (m, 4H).

$^{13}$C NMR (101 MHz, DMSO) δ 173.46, 163.00, 143.39, 133.02, 121.38, 109.96, 61.15, 54.16, 51.94, 39.11, 22.40, 11.14, 9.04.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 37%.

LC-MS (ESI): [M+1]$^+$=478.45, $t_R$=2.19 min.

$^1$H NMR (400 MHz, CDCl$_3$) δ 11.29-10.18 (m, 1H), 8.61-7.01 (m, 3H), 4.73 (ddd, J=34.4, 10.2, 5.4 Hz, 1H), 4.17-3.27 (m, 6H), 2.14-1.00 (m, 14H), 0.94-0.37 (m, 4H).

Example 35

Synthesis of N—((R)-2-(cyclopentylmethyl)-3-((S)-6-(1,1-dioxythiomorpholine-4-carbonyl)-5-azaspiro[2.4]heptane-5-yl)-3-propylcarbonyl)-N-hydroxyformamide

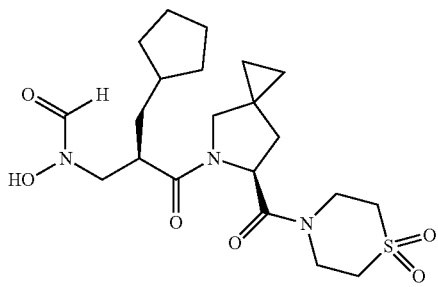 [SMILES: O=CN(O)C[C@@H](CC1CCCC1)C(=O)N1CC2(CC2)C[C@H]1C(=O)N1CCS(=O)(=O)CC1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=259.00, $t_R$=0.37 min.

$^1$H NMR (400 MHz, DMSO) δ 9.94 (t, J=76.9 Hz, 1H), 8.16 (t, J=56.7 Hz, 1H), 4.42-3.90 (m, 1H), 3.64-3.25 (m, 2H), 3.21-2.53 (m, 8H), 2.53-2.01 (m, 2H), 2.01-0.66 (m, 4H).

$^{13}$C NMR (101 MHz, DMSO) δ 167.37, 57.55, 51.79, 50.64, 50.55, 43.26, 40.80, 36.27, 33.89, 20.33, 10.13, 9.41.

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 27%.

LC-MS (ESI): [M+1]$^+$=456.16, $t_R$=1.63 min.

$^1$H NMR (400 MHz, CDCl$_3$) δ 7.88 (s, 1H), 4.99 (s, 1H), 4.66 (d, J=13.7 Hz, 1H), 4.26 (d, J=13.2 Hz, 1H), 3.98 (s, 2H), 3.93-3.66 (m, 3H), 3.61-2.94 (m, 7H), 2.09-1.94 (m, 2H), 1.92-1.20 (m, 10H), 0.80-0.50 (m, 4H).

Example 36

Synthesis of (S)-5-((R)-3-cyclopentyl-2-((N-hydroxyformamido)methyl)propylcarbonyl)-N-(oxazol-2-yl)-5-azaspiro[2.4]heptane-6-amide

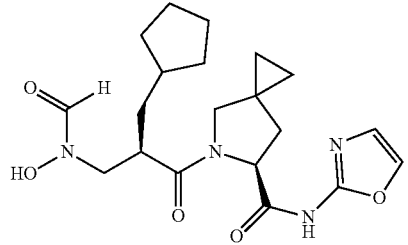 [SMILES: O=CN(O)C[C@@H](CC1CCCC1)C(=O)N1CC2(CC2)C[C@H]1C(=O)Nc1ncco1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=208.32, $t_R$=0.36 min.

$^1$H NMR (400 MHz, DMSO) δ 10.77 (s, 1H), 7.95 (s, 1H), 7.19 (s, 1H), 4.64 (s, 1H), 3.19 (dd, J=12.2, 6.2 Hz, 2H), 2.38 (dd, J=12.9, 8.5 Hz, 1H), 2.01 (dd, J=12.8, 6.7 Hz, 1H), 0.67 (d, J=9.3 Hz, 4H).

$^{13}$C NMR (101 MHz, DMSO) δ 167.30, 152.62, 136.22, 125.77, 59.63, 51.56, 37.35, 20.08, 10.36, 9.71.

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 24%.

LC-MS (ESI): [M+1]$^+$=405.06, $t_R$=1.58 min.

$^1$H NMR (400 MHz, CDCl$_3$) δ 8.72 (s, 1H), 7.59 (s, 1H), 7.14 (s, 1H), 5.36 (s, 1H), 4.18 (s, 1H), 3.65 (s, 1H), 3.42-2.94 (m, 3H), 2.20 (s, 1H), 1.93-0.72 (m, 12H), 0.42-0.13 (m, 4H).

Example 37

Synthesis of (S)-5-((R)-3-cyclopentyl-2-((N-hydroxyformamido)methyl)propionyl)-N-(isoxazol-5-yl)-5-azaspiro[2.4]heptane-6-carboxamide

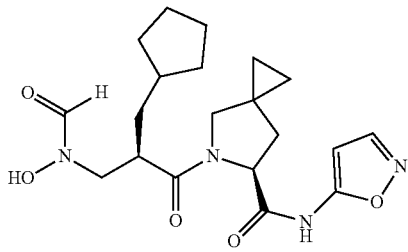 [SMILES: O=CN(O)C[C@@H](CC1CCCC1)C(=O)N1CC2(CC2)C[C@H]1C(=O)Nc1ccno1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=208.11, $t_R$=0.57 min.
$^1$H NMR (400 MHz, DMSO) δ 10.66 (s, 1H), 9.01 (s, 1H), 8.51 (d, J=1.6 Hz, 1H), 6.29 (d, J=1.6 Hz, 1H), 4.98-4.32 (m, 1H), 3.29-2.98 (m, 2H), 2.45-1.87 (m, 2H), 0.85-0.47 (m, 4H).
$^{13}$C NMR (101 MHz, DMSO) δ 165.75, 160.13, 152.15, 88.25, 59.47, 51.64, 37.35, 20.12, 10.27, 9.78
Step 3: The procedure was the same as the Step 3 in the synthesis of the general formula (X2).
Step 4: The procedure was the same as the Step 4 in the synthesis of the general formula (X2). White solid was obtained through column chromatography (DCM:MeOH=10:1), with a two-step yield of 32%.
LC-MS (ESI): [M+1]$^+$=405.53, $t_R$=1.32 min.
$^1$H NMR (400 MHz, CDCl$_3$) δ 10.59 (d, J=42.7 Hz, 1H), 8.26-8.04 (m, 1H), 7.81 (s, 1H), 6.44-6.16 (m, 1H), 4.98-4.70 (m, 1H), 3.94-3.69 (m, 2H), 3.56-3.28 (m, 2H), 2.31-2.06 (m, 2H), 1.85-1.08 (m, 11H), 0.84-0.54 (m, 4H).

Example 38

Synthesis of (S)—N-(5-(tert-butypisoxazol-3-yl)-5-((R)-3-cyclopentyl-2-((N-hydroxyformamido)methyl)propionyl)-5-azaspiro[2.4]heptane-6-carboxamide

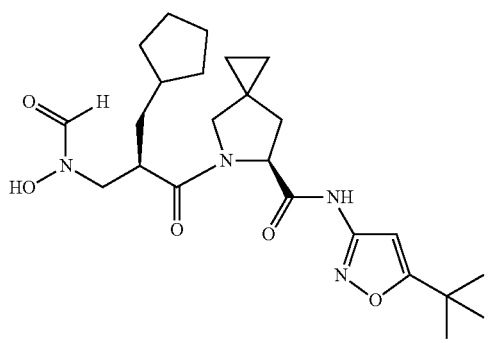 [SMILES: CC(C)(C)c1cc(NC(=O)[C@@H]2CC3(CC3)CN2C(=O)[C@H](CC2CCCC2)CN(O)C=O)no1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=265.07, $t_R$=1.44 min.
$^1$H NMR (400 MHz, D$_2$O) δ 6.14 (s, 1H), 4.44-4.41 (m, 1H), 3.12-2.93 (m, 2H), 2.19 (dd, J=13.4, 8.9 Hz, 1H), 1.86 (dd, J=13.4, 6.1 Hz, 1H), 0.52-0.29 (m, 4H).
$^{13}$C NMR (101 MHz, D$_2$O) δ 183.22, 167.90, 157.06, 93.24, 60.23, 52.67, 37.13, 32.51, 27.67, 20.09, 9.86, 8.49.
Step 3: The procedure was the same as the Step 3 in the synthesis of the general formula (X2).
Step 4: The procedure was the same as the Step 4 in the synthesis of the general formula (X2). White solid was obtained through column chromatography (DCM:MeOH=10:1), with a two-step yield of 31%.
LC-MS (ESI): [M+1]$^+$=461.66, $t_R$=1.46 min.
$^1$H NMR (400 MHz, CDCl$_3$) δ 11.25 (s, 1H), 9.77 (s, 1H), 8.36 (s, 1H), 8.02-7.46 (m, 1H), 6.68 (d, J=28.5 Hz, 1H), 4.92-4.53 (m, 1H), 4.09-3.73 (m, 2H), 3.63-3.41 (m, 2H), 3.31-2.71 (m, 2H), 1.76-1.25 (m, 20H), 0.80-0.49 (m, 4H).

Example 39

Synthesis of (S)-5-((R)-3-cyclopentyl-2-((N-hydroxyformamido)methyl)propylcarbonyl)-N-(5-methylisoxazol-3-yl)-5-azaspiro[2.4]heptane-6-amide

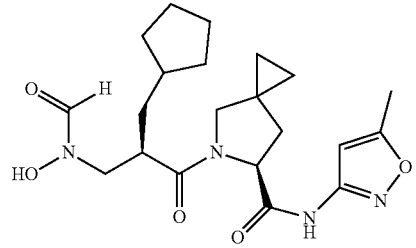 [SMILES: Cc1cc(NC(=O)[C@@H]2CC3(CC3)CN2C(=O)[C@H](CC2CCCC2)CN(O)C=O)no1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=221.79, $t_R$=0.93 min.
$^1$H NMR (400 MHz, DMSO) δ 10.71 (s, 1H), 6.62 (s, 1H), 4.56 (s, 1H), 3.17 (d, J=11.9 Hz, 2H), 2.39 (s, 2H), 2.33 (dd, J=12.8, 8.5 Hz, 1H), 1.98 (dd, J=12.9, 7.0 Hz, 1H), 0.65 (d, J=14.3 Hz, 4H).
$^{13}$C NMR (101 MHz, DMSO) δ 170.05, 167.12, 157.36, 96.21, 59.47, 51.57, 37.49, 20.16, 12.10, 10.16, 9.88.
Step 3: The procedure was the same as the Step 3 in the synthesis of the general formula (X2).
Step 4: The procedure was the same as the Step 4 in the synthesis of the general formula (X2). White solid was obtained through column chromatography (DCM:MeOH=10:1), with a two-step yield of 16%.
LC-MS (ESI): [M+1]$^+$=419.11, $t_R$=1.84 min.
$^1$H NMR (400 MHz, CDCl$_3$) δ 7.81 (s, 1H), 7.18 (s, 1H), 4.73 (d, J=74.6 Hz, 1H), 3.73 (d, J=67.7 Hz, 2H), 3.25 (m, 3H), 2.38 (s, 3H), 2.05 (m, 2H), 1.66-1.16 (m, 11H), 0.57 (m, 4H).

Example 40

Synthesis of (S)-5-((S)-3-cyclopentyl-2-((N-hydroxyformamido)methyl)propionyl)-N-(thiazol-2-yl)-5-spiro[2.4]heptane-6-carboxamide

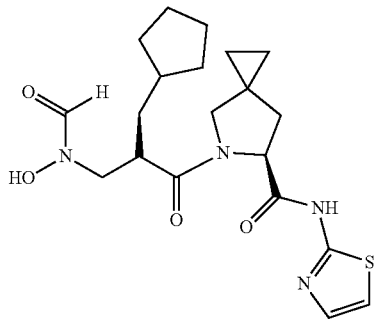

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.38, t$_R$=0.92 min.

$^1$H NMR (400 MHz, DMSO) δ 10.84 (s, 1H), 7.53 (d, J=3.1 Hz, 1H), 7.34 (d, J=3.2 Hz, 1H), 4.79-4.59 (m, 1H), 3.21 (ddd, J=15.7, 10.7, 5.6 Hz, 2H), 2.37 (dd, J=12.9, 8.4 Hz, 1H), 2.03 (dd, J=13.0, 6.9 Hz, 1H), 0.77-0.57 (m, 4H).

$^{13}$C NMR (101 MHz, DMSO) δ 167.07, 157.46, 137.44, 114.41, 59.19, 51.59, 37.46, 20.1 6, 10.22, 9.94.

Step 3: The procedure was the same as the Step 3 in the synthesis of the general formula (X2).

Step 4: The procedure was the same as the Step 4 in the synthesis of the general formula (X2). White solid was obtained through chromatography (DCM:MeOH=10:1), with a two-step yield of 42%.

LC-MS (ESI): [M+1]$^+$=421.00, t$_R$=1.84 min.

$^1$H NMR (400 MHz, CDCl$_3$) δ 11.84 (s, 1H), 10.46 (s, 1H), 8.51-7.68 (m, 1H), 7.34 (d, J=60.6 Hz, 1H), 7.04-6.56 (m, 1H), 5.26-4.62 (m, 1H), 4.43-2.80 (m, 5H), 2.34-1.68 (m, 6H), 1.44-0.98 (m, 7H), 0.72 (ddt, J=59.3, 52.3, 23.7 Hz, 4H).

Example 41

Synthesis of (S)-5-((R)-3-cyclopentyl-2-((N-hydroxyformamido)methyl)propionyl)-N-(1,3,4-thiadiazol-2-yl)-5-azaspiro[2.4]heptane-6-carboxamide

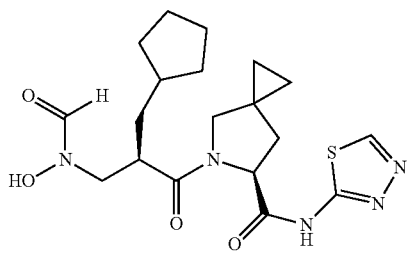 [SMILES: O=CN(O)C[C@@H](CC1CCCC1)C(=O)N1CC2(CC2)C[C@H]1C(=O)Nc1nncs1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.87, t$_R$=0.63 min.

$^1$H NMR (400 MHz, DMSO) δ 10.85 (dd, J=52.8, 47.6 Hz, 1H), 9.13 (t, J=28.8 Hz, 1H), 4.96-4.50 (m, 1H), 3.47-2.92 (m, 2H), 2.46-1.89 (m, 2H), 1.15-0.23 (m, 4H).

$^{13}$C NMR (101 MHz, DMSO) δ 167.60, 158.24, 149.57, 59.31, 51.59, 37.35, 20.10, 10.31, 9.77.

Step 3: The procedure was the same as the Step 3 in the synthesis of the general formula (X2).

Step 4: The procedure was the same as the Step 4 in the synthesis of the general formula (X2). White solid was obtained through column chromatography (DCM:MeOH=10:1), with a two-step yield of 33%.

LC-MS (ESI): [M+1]$^+$=422.14, t$_R$=1.65 min.

$^1$H NMR (400 MHz, CDCl$_3$) δ 8.80 (s, 1H), 7.27 (s, 1H), 6.06-5.12 (m, 1H), 5.15-4.62 (m, 1H), 4.29-3.82 (m, 1H), 3.79-3.02 (m, 3H), 2.99-2.34 (m, 1H), 2.31-2.15 (m, 1H), 2.10-1.50 (m, 7H), 1.48-1.26 (m, 5H), 1.17-0.95 (m, 2H), 0.86-0.69 (m, 2H).

Example 42

Synthesis of N—((R)-3-((S)-6-(1H-benzimidazol-2-yl)-5-azaspiro[2.4]heptane-5-yl)-2-(cyclopentylmethyl)-3-propylcarbonyl)-N-hydroxyformamide

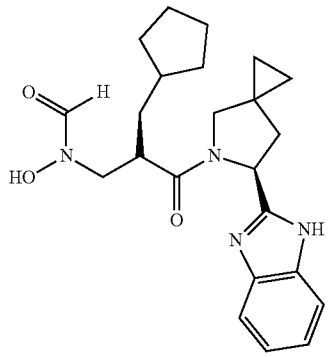

Step 1: The procedure was the same as the Step 1 in Example 1.

Step 2: The procedure was the same as the Step 2 in Example 1.

Step 3: The procedure was the same as the Step 3 in Example 1.

LC-MS (ESI): [M+1]$^+$=214.16, t$_R$=0.94 min.

$^1$H NMR (400 MHz, D$_2$O) δ 7.67-7.58 (m, 2H), 7.49-7.39 (m, 2H), 5.41 (t, J=8.6 Hz, 1H), 3.55-3.46 (m, 1H), 3.25-3.15 (m, 1H), 2.68-2.57 (m, 1H), 2.39-2.28 (m, 1H), 0.85-0.60 (m, 4H).

$^{13}$C NMR (101 MHz, D$_2$O) δ 144.90, 130.95, 127.05, 114.21, 36.52, 20.20, 11.92, 7.25.

Step 4: The procedure was the same as the Step 3 in the synthesis of the general formula (X2).

Step 5: The procedure was the same as the Step 4 in the synthesis of the general formula (X2). White solid was obtained through column chromatography (DCM:MeOH=10:1), with a two-step yield of 33%.

LC-MS (ESI): [M+1]$^+$=412.18, t$_R$=1.60 min.

$^1$H NMR (400 MHz, CDCl$_3$) δ 8.44-7.11 (m, 5H), 5.58 (s, 1H), 4.04 (s, 1H), 3.89-2.64 (m, 4H), 2.51-2.02 (m, 2H), 1.95-0.94 (m, 11H), 0.89-0.29 (m, 4H).

Example 43

Synthesis of (S)-5-((R)-2-(2-(hydroxyamino)-2-oxoethyl)hexanoyl)-N-(4-morpholinophenyl)-5-spiro[2.4]heptane-6-carboxamide

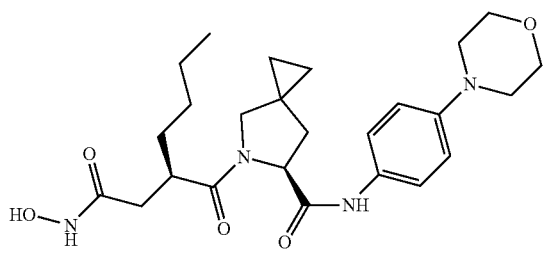 [SMILES: CCCC[C@H](CC(=O)NO)C(=O)N1CC2(CC2)C[C@H]1C(=O)Nc1ccc(N2CCOCC2)cc1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=302.05, $t_R$=1.06 min.

$^1$H NMR (400 MHz, DMSO) δ 10.82 (s, 1H), 7.52 (d, J=8.8 Hz, 2H), 6.93 (d, J=8.8 Hz, 2H), 4.55 (t, J=7.9 Hz, 1H), 3.78-3.67 (m, 4H), 3.19 (dd, J=37.9, 11.2 Hz, 2H), 3.08-3.02 (m, 4H), 2.33 (dd, J=12.9, 8.2 Hz, 1H), 2.01 (dd, J=12.9, 7.6 Hz, 1H), 0.78-0.53 (m, 4H).

$^{13}$C NMR (101 MHz, DMSO) δ 165.87, 147.72, 130.32, 120.50, 115.35, 66.04, 59.59, 51.66, 48.71, 37.81, 20.35, 10.34, 9.73.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2). The three-step yield reached 20%.

LC-MS (ESI): [M+1]$^+$=514.83, $t_R$=1.56 min.

$^1$H NMR (400 MHz, CDCl$_3$) δ 7.34 (s, 1H), 6.90 (s, 1H), 5.06 (s, 1H), 4.46 (s, 1H), 3.71 (d, J=18.0 Hz, 3H), 3.17 (d, J=17.6 Hz, 3H), 2.82 (d, J=28.7 Hz, 1H), 2.36 (s, 1H), 1.97 (s, 1H), 1.67-1.08 (m, 3H), 0.89-0.52 (m, 4H).

Example 44

Synthesis of (S)-5-((R)-2-(2-(hydroxyamino)-2-oxoethyl)hexanoyl)-N-(pyrazin-2-yl-5-spiro[2.4]heptane-6-carboxamide

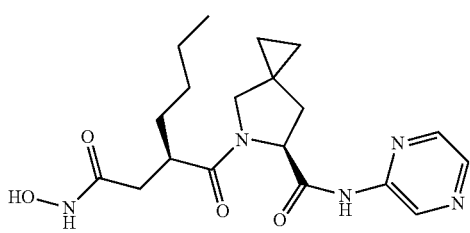 [SMILES: CCCC[C@H](CC(=O)NO)C(=O)N1CC2(CC2)C[C@H]1C(=O)Nc1cnccn1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.57 min.

$^1$H NMR (400 MHz, D$_2$O) δ 8.98 (d, J=96.9 Hz, 1H), 8.31 (t, J=81.8 Hz, 2H), 4.66-4.49 (m, 1H), 3.26-2.81 (m, 2H), 2.29-1.62 (m, 2H), 0.63-0.09 (m, 4H).

$^{13}$C NMR (101 MHz, D$_2$O) δ 148.55, 144.82, 137.12, 133.80, 60.43, 52.76, 37.11, 20.13, 9.77, 8.95, 8.64.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2). The three-step yield reached 20%.

LC-MS (ESI): [M+1]$^+$=390.52, $t_R$=1.36 min.

$^1$H NMR (400 MHz, DMSO) δ 12.86-11.39 (m, 1H), 10.31 (d, J=98.3 Hz, 1H), 7.83-6.53 (m, 3H), 5.52-4.73 (m, 1H), 4.11 (dd, J=44.5, 40.2 Hz, 1H), 3.94-3.35 (m, 2H), 3.03-0.74 (m, 13H), 0.71-0.24 (m, 4H).

Example 45

Synthesis of (S)-5-((R)-2-(2-(hydroxyamino)-2-oxoethyl)hexanoyl)-N-(pyrimidin-4-yl-5-spiro[2.4]heptane-6-carboxamide

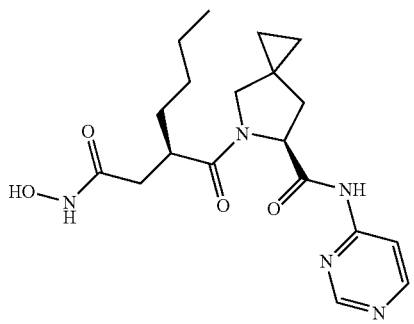 [SMILES: CCCC[C@H](CC(=O)NO)C(=O)N1CC2(CC2)C[C@H]1C(=O)Nc1ccncn1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.43 min.

$^1$H NMR (400 MHz, D$_2$O) δ 9.08 (s, 1H), 8.78 (d, J=6.8 Hz, 1H), 8.42 (t, J=31.2 Hz, 1H), 4.82 (dd, J=8.7, 6.4 Hz, 1H), 3.50-3.15 (m, 2H), 2.57-2.00 (m, 2H), 0.88-0.58 (m, 4H).

$^{13}$C NMR (101 MHz, D$_2$O) δ 169.77, 152.74, 150.17, 111.15, 60.98, 52.82, 36.76, 20.08, 9.91, 8.50.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2). The three-step yield reached 20%.

LC-MS (ESI): [M+1]$^+$=390.52, $t_R$=1.38 min.

$^1$H NMR (400 MHz, CDCl$_3$) δ 8.97 (s, 1H), 8.78 (s, 1H), 7.67 (s, 1H), 4.94 (s, 1H), 3.52-2.98 (m, 3H), 2.89-2.34 (m, 3H), 1.92-1.09 (m, 7H), 0.89 (s, 3H), 0.68-0.42 (m, 4H).

Example 46

Synthesis of (S)—N-(5-fluoropyridin-2-yl)-5-((R)-2-(2-(hydroxyamino)-2-oxoethyl)hexanoyl)-5-spiro[2.4]heptane-6-carboxamide

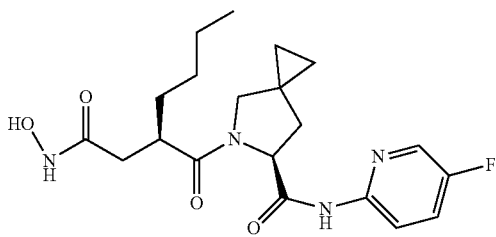 [SMILES: CCCC[C@H](CC(=O)NO)C(=O)N1CC2(CC2)C[C@H]1C(=O)Nc1ccc(F)cn1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=236.09, $t_R$=1.00 min.

¹H NMR (400 MHz, D₂O) δ 8.25 (s, 1H), 8.11-7.80 (m, 1H), 7.65 (dd, J=9.1, 3.7 Hz, 1H), 4.74 (d, J=7.9 Hz, 1H), 3.44-3.15 (m, 2H), 2.59-1.94 (m, 2H), 0.84-0.47 (m, 4H).

¹³C NMR (101 MHz, D₂O) δ 169.09, 157.99, 155.50, 144.99, 118.16, 118.10, 60.33, 52.77, 37.08, 20.12, 9.73, 8.73.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2). The three-step yield reached 36%.

LC-MS (ESI): [M+1]⁺=407.52, $t_R$=1.93 min.

¹H NMR (400 MHz, CDCl₃) δ 10.41 (d, J=191.4 Hz, 1H), 9.42 (d, J=136.3 Hz, 1H), 8.11 (dt, J=70.7, 24.8 Hz, 2H), 7.65-7.17 (m, 1H), 5.20-4.40 (m, 1H), 4.16-1.83 (m, 7H), 1.79-0.97 (m, 9H), 0.97-0.21 (m, 6H).

Example 47

Synthesis of (S)-5-((R)-2-(2-(hydroxyamino)-2-oxoethyl)hexanoyl)-N-(5-methylthiazol-2-yl)-5-azaspiro[2.4]heptane-6-amide

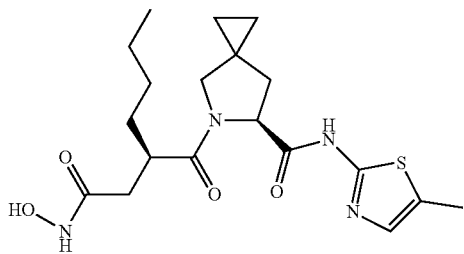 [SMILES: CCCC[C@H](CC(=O)NO)C(=O)N1CC2(CC2)C[C@H]1C(=O)Nc1ncc(C)s1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=238.45, $t_R$=1.09 min.

¹H NMR (400 MHz, D₂O) δ 7.24 (s, 1H), 4.77 (dd, J=8.9, 6.5 Hz, 1H), 3.24 (s, 2H), 2.38 (dd, J=13.4, 9.1 Hz, 1H), 2.28 (s, 3H), 2.05 (dd, J=13.4, 6.3 Hz, 1H), 0.72-0.45 (m, 4H).

¹³C NMR (101 MHz, D₂O) δ 168.01, 159.21, 129.86, 124.06, 60.16, 52.75, 36.68, 20.02, 11.03, 9.78, 8.73.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 25%.

LC-MS (ESI): [M+1]⁺=409.53, $t_R$=1.38 min.

¹H NMR (400 MHz, DMSO) δ 12.02 (d, J=79.3 Hz, 1H), 10.37 (s, 1H), 9.07-8.35 (m, 1H), 7.38-6.92 (m, 1H), 5.51-4.35 (m, 1H), 3.83-3.38 (m, 2H), 3.34 (s, 2H), 2.97-2.61 (m, 1H), 2.54-2.43 (m, 2H), 2.40-2.28 (m, 2H), 2.28-1.67 (m, 4H), 1.56-1.06 (m, 6H), 0.99-0.81 (m, 2H), 0.78-0.19 (m, 4H).

Example 48

Synthesis of (S)-5-((R)-2-(2-(hydroxyamino)-2-oxoethyl)hexanoyl)-N-(pyridazin-3-yl)-5-azaspiro[2.4]heptane-6-amide

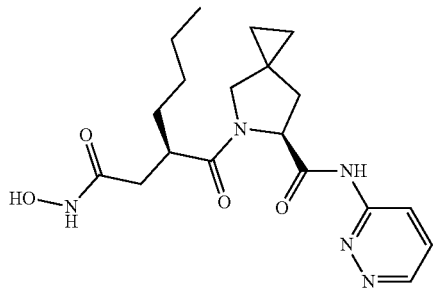 [SMILES: CCCC[C@H](CC(=O)NO)C(=O)N1CC2(CC2)C[C@H]1C(=O)Nc1cccnn1]

Step 1: The procedure was the same as the Step 1 in the synthesis of the general formula (X1).

Step 2: The procedure was the same as the Step 2 in the synthesis of the general formula (X1).

LC-MS (ESI): [M+1]⁺=219.14, $t_R$=0.55 min.

¹H NMR (400 MHz, D₂O) δ 9.19 (d, J=5.0 Hz, 1H), 8.78 (d, J=9.2 Hz, 1H), 8.29 (dd, J=9.2, 5.2 Hz, 1H), 4.92-4.78 (m, 1H), 3.47-3.15 (m, 2H), 2.50 (dd, J=13.4, 9.1 Hz, 1H), 2.20 (dd, J=13.4, 6.3 Hz, 1H), 0.85-0.59 (m, 4H).

¹³C NMR (101 MHz, D₂O) δ 169.33, 155.57, 145.59, 134.68, 128.12, 60.68, 52.82, 36.96, 20.13, 9.84, 8.65.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 20%.

LC-MS (ESI): [M+1]⁺=390.26, $t_R$=1.68 min.

¹H NMR (400 MHz, CDCl₃) δ 10.42 (s, 1H), 8.88 (s, 1H), 8.44 (t, J=36.8 Hz, 1H), 7.50 (s, 1H), 5.17-4.79 (m, 1H), 3.83-3.65 (m, 1H), 3.58 (dd, J=19.5, 9.4 Hz, 1H), 3.18 (d, J=7.0 Hz, 1H), 2.41-2.16 (m, 2H), 2.04 (t, J=18.5 Hz, 1H), 1.62 (d, J=4.2 Hz, 1H), 1.50-1.36 (m, 6H), 0.84 (s, 3H), 0.75-0.48 (m, 4H).

Example 49

Synthesis of (S)—N-(3-fluoropyridin-2-yl)-5-((R)-2-(2-(hydroxyamino)-2-oxoethyl)hexanoyl)-5-azaspiro[2.4]heptane-6-amide

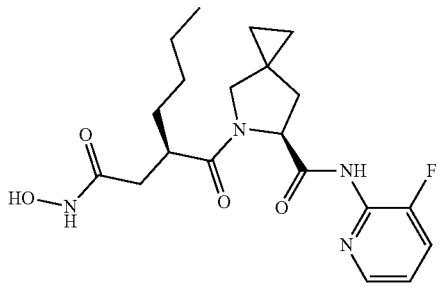 [SMILES: CCCC[C@H](CC(=O)NO)C(=O)N1CC2(CC2)C[C@H]1C(=O)Nc1ncccc1F]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=235.90, $t_R$=0.60 min.
$^1$H NMR (400 MHz, D$_2$O) δ 8.20 (d, J=5.5 Hz, 1H), 8.06 (t, J=9.0 Hz, 1H), 7.56-7.50 (m, 1H), 4.90-4.79 (m, 1H), 3.31 (s, 2H), 2.61-2.39 (m, 1H), 2.15 (dd, J=13.4, 6.1 Hz, 1H), 0.76-0.54 (m, 4H).
$^{13}$C NMR (101 MHz, D$_2$O) δ 169.94, 150.12 (d, J=255.5 Hz), 138.18, 137.92 (d, J=13.4 Hz), 130.12 (d, J=16.9 Hz), 123.10 (d, J=5.8 Hz), 60.39, 52.83, 37.21, 20.06, 9.96, 8.50.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 22%.
LC-MS (ESI): [M+1]$^+$=407.33, $t_R$=1.63 min.
$^1$H NMR (400 MHz, DMSO) δ 10.57-10.32 (m, 1H), 10.30-10.06 (m, 1H), 9.11-8.61 (m, 1H), 8.59-7.77 (m, 2H), 7.82-7.13 (m, 1H), 5.25-4.52 (m, 1H), 3.75-3.52 (m, 2H), 3.34 (s, 2H), 3.22-3.01 (m, 2H), 2.95-2.57 (m, 1H), 2.36-1.70 (m, 2H), 1.55-1.25 (m, 7H), 1.11-0.35 (m, 4H).

Example 50

Synthesis of (S)—N-cyclopropyl-5-((R)-2-(2-(hydroxyamino)-2-oxoethyl)hexanoyl)-5-azaspiro[2.4]heptane-6-carboxamide

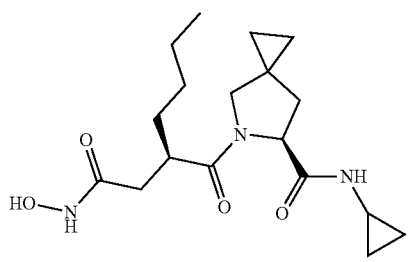 [SMILES: CCCC[C@H](CC(=O)NO)C(=O)N1CC2(CC2)C[C@H]1C(=O)NC1CC1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=182.98, $t_R$=0.550 min
$^1$H NMR (400 MHz, CDCl$_3$) δ 7.82 (s, 1H), 3.93 (dd, J=8.7, 5.2 Hz, 1H), 3.00-2.95 (m, 1H), 2.89 (s, 1H), 2.77-2.71 (m, 2H), 2.24-1.78 (m, 2H), 0.97-0.25 (m, 8H).
$^{13}$C NMR (101 MHz, CDCl$_3$) δ 175.92, 60.94, 54.70, 39.27, 22.37, 22.09, 11.00, 9.48, 6.30, 6.27.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 25%.
LC-MS (ESI): [M+1]$^+$=352.33, $t_R$=1.47 min
$^1$H NMR (400 MHz, CDCl$_3$) δ 6.13-5.33 (m, 1H), 3.72 (d, J=6.1 Hz, 2H), 3.33-2.98 (m, 2H), 2.64-1.84 (m, 1H), 1.70-1.62 (m, 1H), 1.52-1.41 (m, 12H), 1.39-1.21 (m, 4H), 1.19-0.52 (m, 3H).

Example 51

Synthesis of (S)-5-((R)-2-(2-(hydroxyamino)-2-oxoethyl)hexanoyl)-N-(4-methylthiazol-2-yl)-5-spiro[2.4]heptane-6-carboxamide

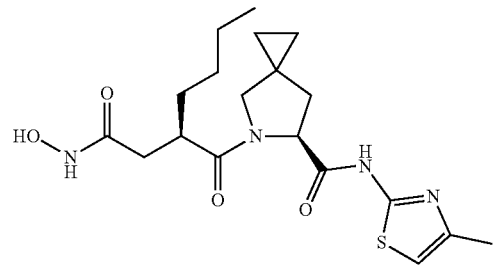 [SMILES: CCCC[C@H](CC(=O)NO)C(=O)N1CC2(CC2)C[C@H]1C(=O)Nc1nc(C)cs1]

Step 1: The procedure was the same as the Step 1 in the synthesis of the general formula (X1).
Step 1: The procedure was the same as the Step 2 in the synthesis of the general formula (X1).
LC-MS (ESI): [M+1]$^+$=219.14, $t_R$=0.43 min.
$^1$H NMR (400 MHz, DMSO) δ 9.09 (d, J=4.8 Hz, 1H), 6.89 (d, J=0.9 Hz, 1H), 4.92-4.46 (m, 1H), 3.42-2.98 (m, 2H), 2.48-1.85 (m, 5H), 0.88-0.41 (m, 4H).
$^{13}$C NMR (101 MHz, DMSO) δ 167.14, 157.01, 146.07, 108.59, 59.22, 51.52, 37.47, 20.13, 16.53, 10.22, 9.90.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 29%.
LC-MS (ESI): [M+1]$^+$=409.34, $t_R$=1.84 min.
$^1$H NMR (400 MHz, DMSO) δ 12.02 (d, J=79.3 Hz, 1H), 10.37 (s, 1H), 9.07-8.35 (m, 1H), 7.38-6.92 (m, 1H), 5.51-4.35 (m, 1H), 3.83-3.38 (m, 2H), 3.34 (s, 2H), 2.97-2.61 (m, 1H), 2.54-2.43 (m, 2H), 2.40-2.28 (m, 2H), 2.28-1.67 (m, 4H), 1.56-1.06 (m, 6H), 0.99-0.81 (m, 2H), 0.78-0.19 (m, 4H).

Example 52

Synthesis of (S)—N-(1-(2-(dimethylamino)ethyl)-1H-pyrazol-4-yl)-5-((R)-2-(2-(hydroxyamino)-2-oxoethyl)hexanoyl)-5-spiro[2.4]heptane-6-carboxamide

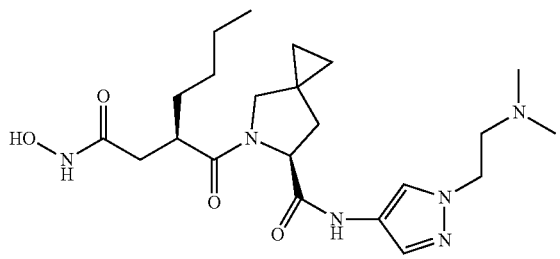 [SMILES: CCCC[C@H](CC(=O)NO)C(=O)N1CC2(CC2)C[C@H]1C(=O)Nc1cnn(CCN(C)C)c1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=278.38, $t_R$=1.10 min.
$^1$H NMR (400 MHz, D$_2$O) δ 8.01-7.76 (m, 1H), 7.59 (d, J=22.1 Hz, 1H), 4.53-4.38 (m, 2H), 3.69-3.39 (m, 3H), 2.86-2.73 (m, 6H), 2.41-2.27 (m, 1H), 2.11-1.94 (m, 1H), 1.32-0.90 (m, 2H), 0.74-0.53 (m, 4H).
$^{13}$C NMR (101 MHz, D$_2$O) δ 167.17, 133.04, 123.88, 119.97, 56.50, 52.60, 48.83, 46.22, 43.03, 37.19, 20.12, 9.59, 8.76.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 20%.
LC-MS (ESI): [M+1]$^+$=449.35, $t_R$=1.13 min.
$^1$H NMR (500 MHz, CDCl$_3$) δ 7.86 (s, 1H), 7.18 (s, 1H), 5.30 (d, J=161.0 Hz, 3H), 3.75 (d, J=12.0 Hz, 3H), 3.28-2.38 (m, 10H), 2.27-0.72 (m, 11H), 0.37 (d, J=91.8 Hz, 4H).

Example 53

Synthesis of (S)-5-((R)-2-(2-(hydroxyamino)-2-oxoethyl)hexanoyl)-N-(oxazol-2-yl)-5-azaspiro[2.4]heptane-6-carboxamide

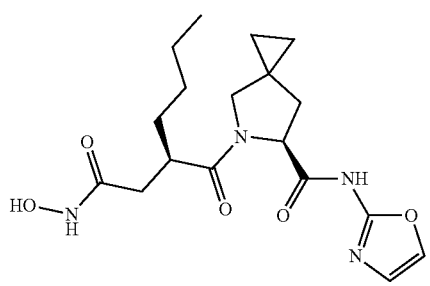 [SMILES: CCCC[C@H](CC(=O)NO)C(=O)N1CC2(CC2)C[C@H]1C(=O)Nc1ncco1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=208.32, $t_R$=0.36 min.
$^1$H NMR (400 MHz, DMSO) δ 10.77 (s, 1H), 7.95 (s, 1H), 7.19 (s, 1H), 4.64 (s, 1H), 3.19 (dd, J=12.2, 6.2 Hz, 2H), 2.38 (dd, J=12.9, 8.5 Hz, 1H), 2.01 (dd, J=12.8, 6.7 Hz, 1H), 0.67 (d, J=9.3 Hz, 4H).
$^{13}$C NMR (101 MHz, DMSO) δ 167.30, 152.62, 136.22, 125.77, 59.63, 51.56, 37.35, 20.08, 10.36, 9.71.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 23%.
LC-MS (ESI): [M+1]$^+$=379.23, $t_R$=1.49 min.
$^1$H NMR (400 MHz, DMSO) δ 11.57-10.73 (m, 1H), 10.59-9.67 (m, 1H), 9.10-8.40 (m, 1H), 7.86 (d, J=7.9 Hz, 1H), 7.17-6.58 (m, 1H), 3.71-3.47 (m, 1H), 3.34 (s, 1H), 3.03-2.77 (m, 1H), 2.70 (d, J=8.0 Hz, 4H), 2.55-2.41 (m, 2H), 2.29-1.79 (m, 2H), 1.63-0.89 (m, 7H), 0.85 (t, J=6.5 Hz, 2H), 0.63-0.14 (m, 2H).

Example 54

Synthesis of (S)-5-((R)-2-(2-(hydroxyamino)-2-oxoethyl)hexanoyl)-N-(isoxazol-5-yl)-5-spiro[2.4]heptane-6-carboxamide

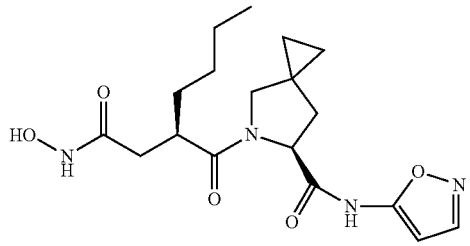 [SMILES: CCCC[C@H](CC(=O)NO)C(=O)N1CC2(CC2)C[C@H]1C(=O)Nc1ccno1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=208.11, $t_R$=0.57 min.
$^1$H NMR (400 MHz, DMSO) δ 10.66 (s, 1H), 9.01 (s, 1H), 8.51 (d, J=1.6 Hz, 1H), 6.29 (d, J=1.6 Hz, 1H), 4.98-4.32 (m, 1H), 3.29-2.98 (m, 2H), 2.45-1.87 (m, 2H), 0.85-0.47 (m, 4H).
$^{13}$C NMR (101 MHz, DMSO) δ 165.75, 160.13, 152.15, 88.25, 59.47, 51.64, 37.35, 20.12, 10.27, 9.78
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 20%.
LC-MS (ESI): [M+1]$^+$=379.23, $t_R$=1.53 min.

¹H NMR (400 MHz, CDCl₃) δ 10.99 (t, J=150.4 Hz, 1H), 9.89 (s, 1H), 8.45-7.95 (m, 1H), 7.27 (s, 1H), 6.63-6.16 (m, 1H), 5.05-4.48 (m, 1H), 3.98-3.33 (m, 2H), 3.11-1.04 (m, 12H), 1.01-0.28 (m, 6H).

Example 55

Synthesis of (S)—N-(5-(tert-butypisoxazol-3-yl)-5-((R)-2-(2-(hydroxyamino)-2-oxoethyl)hexanoyl)-5-azaspiro[2.4]heptane-6-carboxamide

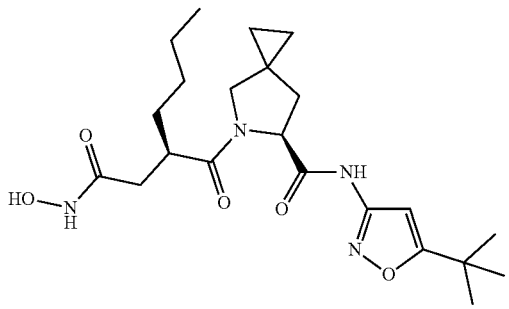 [SMILES: CCCC[C@H](CC(=O)NO)C(=O)N1CC2(CC2)C[C@H]1C(=O)Nc1cc(C(C)(C)C)on1]

Step 1: The procedure was the same as the Step 1 in the synthesis of the general formula (X1).
Step 2: The procedure was the same as the Step 2 in the synthesis of the general formula (X1).
LC-MS (ESI): [M+1]⁺=265.07, $t_R$=1.44 min.
¹H NMR (400 MHz, D₂O) δ 6.14 (s, 1H), 4.44-4.41 (m, 1H), 3.12-2.93 (m, 2H), 2.19 (dd, J=13.4, 8.9 Hz, 1H), 1.86 (dd, J=13.4, 6.1 Hz, 1H), 0.52-0.29 (m, 4H).
¹³C NMR (101 MHz, D₂O) δ 183.22, 167.90, 157.06, 93.24, 60.23, 52.67, 37.13, 32.51, 27.67, 20.09, 9.86, 8.49.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 23%.
LC-MS (ESI): [M+1]⁺=435.30, $t_R$=2.02 min.
¹H NMR (400 MHz, CDCl₃) δ 11.01 (d, J=134.6 Hz, 1H), 10.47-9.87 (m, 1H), 6.74-6.29 (m, 1H), 5.65 (s, 1H), 5.05-4.42 (m, 1H), 3.96-3.16 (m, 2H), 3.05-2.71 (m, 2H), 2.51-1.95 (m, 2H), 1.36-1.13 (m, 18H), 0.90-0.50 (m, 4H).

Example 56

Synthesis of (S)-5-((R)-2-(2-(hydroxyamino)-2-oxoethyl)hexanoyl)-N-(5-methylisoxazol-3-yl)-5-spiro[2.4]heptane-6-carboxamide

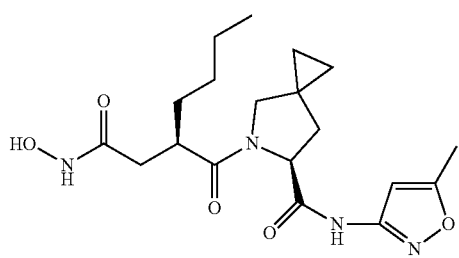 [SMILES: CCCC[C@H](CC(=O)NO)C(=O)N1CC2(CC2)C[C@H]1C(=O)Nc1cc(C)on1]

Step 1: The procedure was the same as the Step 1 in the synthesis of the general formula (X1).
Step 2: The procedure was the same as the Step 2 in the synthesis of the general formula (X1).
LC-MS (ESI): [M+1]⁺=221.79, $t_R$=0.93 min.
¹H NMR (400 MHz, DMSO) δ 10.71 (s, 1H), 6.62 (s, 1H), 4.56 (s, 1H), 3.17 (d, J=11.9 Hz, 2H), 2.39 (s, 2H), 2.33 (dd, J=12.8, 8.5 Hz, 1H), 1.98 (dd, J=12.9, 7.0 Hz, 1H), 0.65 (d, J=14.3 Hz, 4H).
¹³C NMR (101 MHz, DMSO) δ 170.05, 167.12, 157.36, 96.21, 59.47, 51.57, 37.49, 20.16, 12.10, 10.16, 9.88.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 29%.
LC-MS (ESI): [M+1]⁺=393.42, $t_R$=1.79 min.
¹H NMR (500 MHz, CDCl₃) δ 6.59 (s, 1H), 4.98 (s, 1H), 4.06 (d, J=161.2 Hz, 2H), 3.46-2.23 (m, 7H), 1.96 (s, 1H), 1.72-1.14 (m, 6H), 1.03-0.28 (m, 7H).

Example 57

Synthesis of (S)-5-((R)-2-(2-(hydroxyamino)-2-oxoethyl)hexanoyl)-N-(5-(trifluoromethyl)thiazol-2-yl)-5-spiro[2.4]heptane-6-carboxamide

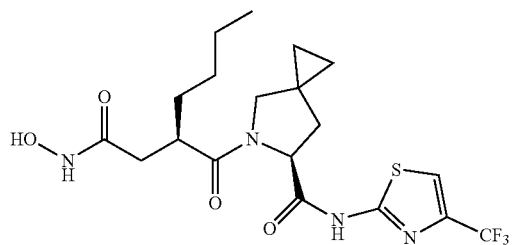 [SMILES: CCCC[C@H](CC(=O)NO)C(=O)N1CC2(CC2)C[C@H]1C(=O)Nc1nc(C(F)(F)F)cs1]

Step 1: The procedure was the same as the Step 1 in the synthesis of the general formula (X1).
Step 2: The procedure was the same as the Step 2 in the synthesis of the general formula (X1).
LC-MS (ESI): [M+1]⁺=292.22, $t_R$=1.28 min
¹H NMR (400 MHz, DMSO) δ 10.46 (s, 1H), 8.09 (d, J=0.9 Hz, 1H), 4.67 (dd, J=8.1, 7.0 Hz, 1H), 3.26-3.17 (m, 2H), 2.36 (dd, J=13.2, 8.5 Hz, 1H), 2.06 (dd, J=13.2, 6.6 Hz, 1H), 0.76-0.61 (m, 4H).
¹³C NMR (101 MHz, DMSO) δ 167.88, 159.26, 121.96, 119.23, 117.58, 59.25, 51.77, 37.12, 20.13, 10.32, 9.60.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 32%.
LC-MS (ESI): [M+1]⁺=463.08, $t_R$=2.00 min.
¹H NMR (400 MHz, CDCl₃) δ 12.92-11.05 (m, 1H), 10.14 (s, 1H), 8.07-6.63 (m, 1H), 5.60-4.50 (m, 1H), 3.71 (ddd, J=49.1, 46.6, 9.5 Hz, 2H), 3.46-2.27 (m, 2H), 2.08 (ddd, J=54.9, 36.3, 19.1 Hz, 2H), 1.80-1.12 (m, 6H), 1.10-0.31 (m, 7H).

Example 58

Synthesis of (R)-3-((S)-6-(1H-benzimidazol-2-yl)-5-azaspiro[2.4]heptane-5-formyl)-N-hydroxyheptanamide

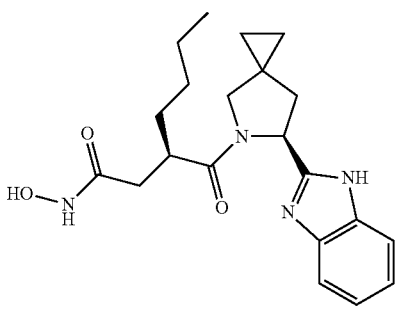 [SMILES: CCCC[C@H](CC(=O)NO)C(=O)N1CC2(CC2)C[C@H]1c1nc2ccccc2[nH]1]

Step 1: The procedure was the same as the Step 1 in Example 1.
Step 2: The procedure was the same as the Step 2 in Example 1.
Step 3: The procedure was the same as the Step 3 in Example 1.
LC-MS (ESI): [M+1]$^+$=214.16, $t_R$=0.94 min.
$^1$H NMR (400 MHz, D$_2$O) δ 7.67-7.58 (m, 2H), 7.49-7.39 (m, 2H), 5.41 (t, J=8.6 Hz, 1H), 3.55-3.46 (m, 1H), 3.25-3.15 (m, 1H), 2.68-2.57 (m, 1H), 2.39-2.28 (m, 1H), 0.85-0.60 (m, 4H).
$^{13}$C NMR (101 MHz, D$_2$O) δ 144.90, 130.95, 127.05, 114.21, 36.52, 20.20, 11.92, 7.25.
Step 4: The procedure was the same as the Step 3 in the synthesis of the general formula (X2).
Step 5: The procedure was the same as the Step 4 in the synthesis of the general formula (X2).
Step 6: The procedure was the same as the Step 5 in the synthesis of the general formula (X2), and the three-step yield was 17%.
LC-MS (ESI): [M+1]$^+$=385.49, $t_R$=1.65 min.
$^1$H NMR (400 MHz, DMSO) δ 7.48 (s, 2H), 7.15 (t, J=21.2 Hz, 2H), 5.48-5.07 (m, 1H), 3.88-3.53 (m, 2H), 3.41 (dd, J=23.6, 16.5 Hz, 2H), 2.81 (d, J=51.3 Hz, 1H), 2.40-2.11 (m, 2H), 1.84-1.00 (m, 9H), 0.79-0.30 (m, 4H).

Example 59

Synthesis of (R)-3-((R)-6-(1H-benzimidazol-2-yl)-5-azaspiro[2.4]heptane-5-carbonyl)-N-hydroxyheptanamide

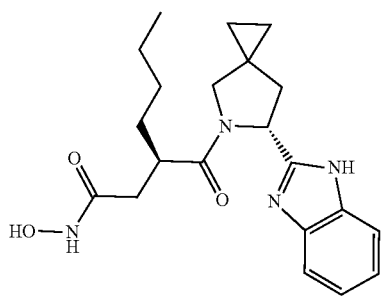 [SMILES: CCCC[C@H](CC(=O)NO)C(=O)N1CC2(CC2)C[C@@H]1c1nc2ccccc2[nH]1]

Step 1: The procedure was the same as the Step 1 in Example 1.
Step 2: The procedure was the same as the Step 2 in Example 1.
Step 3: The procedure was the same as the Step 3 in Example 1.
LC-MS (ESI): [M+1]$^+$=385.49, $t_R$=1.65 min.
$^1$H NMR (400 MHz, CDCl$_3$) δ 7.57 (s, 2H), 7.22 (s, 2H), 5.43 (dd, J=36.1, 29.6 Hz, 1H), 3.93-3.79 (m, 1H), 3.48-3.31 (m, 1H), 3.09-2.28 (m, 5H), 2.07-1.90 (m, 1H), 1.24 (dd, J=26.4, 11.2 Hz, 5H), 0.78-0.61 (m, 7H).

Example 60

Synthesis of (R)-3-((S)-6-(1-(2-(dimethylamino)ethyl)-1H-benzimidazol-2-yl)-5-azaspiro[2.4]heptane-5-carbonyl)-N-hydroxyheptanamide

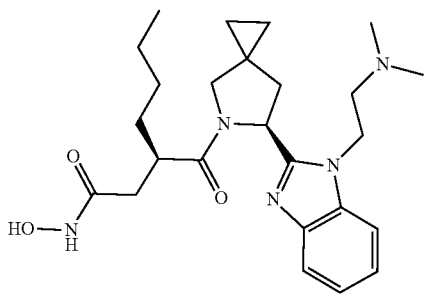 [SMILES: CCCC[C@H](CC(=O)NO)C(=O)N1CC2(CC2)C[C@H]1c1nc2ccccc2n1CCN(C)C]

Step 1: The procedure was the same as the Step 1 in Example 1.
Step 2: The procedure was the same as the Step 2 in Example 1.
Step 3: The procedure was the same as the Step 3 in Example 1.
LC-MS (ESI): [M+1]$^+$=285.17, $t_R$=0.57 min.
$^1$H NMR (400 MHz, D$_2$O) δ 7.80-7.61 (m, 2H), 7.58-7.39 (m, 2H), 5.50 (dd, J=9.1, 7.8 Hz, 1H), 4.93-4.76 (m, 2H), 3.69-3.22 (m, 4H), 2.96 (s, 6H), 2.67-2.22 (m, 2H), 0.88-0.63 (m, 4H).
$^{13}$C NMR (101 MHz, D$_2$O) δ 147.40, 135.78, 132.90, 126.31, 126.04, 117.18, 111.46, 54.06, 52.87, 52.72, 43.42, 39.33, 38.01, 20.39, 11.70, 7.58.
Step 4: The procedure was the same as the Step 3 in the synthesis of the general formula (X2).
Step 5: The procedure was the same as the Step 4 in the synthesis of the general formula (X2).
Step 6: The procedure was the same as the Step 5 in the synthesis of the general formula (X2), and the three-step yield was 17%.
LC-MS (ESI): [M+1]$^+$=456.34 $t_R$=1.23 min.
$^1$H NMR (400 MHz, DMSO) δ 10.34 (d, J=47.3 Hz, 1H), 9.91 (d, J=51.5 Hz, 1H), 8.00-7.62 (m, 2H), 7.57-7.26 (m, 2H), 5.40 (dd, J=26.3, 18.9 Hz, 1H), 5.03-4.68 (m, 2H), 4.02 (d, J=9.4 Hz, 1H), 3.76-3.66 (m, 1H), 3.64-3.50 (m, 2H), 3.04-2.76 (m, 6H), 2.50 (s, 2H), 2.48-1.85 (m, 4H), 1.46-1.17 (m, 7H), 1.20-0.99 (m, 2H), 0.86-0.58 (m, 6H).

Example 61

Synthesis of (S)-5-((R)-2-(cyclopentylmethyl)-4-(hydroxyamino)-4-oxobutyl)-N-(4-morpholinophenyl)-5-azaspiro[2.4]heptane-6-carboxamide

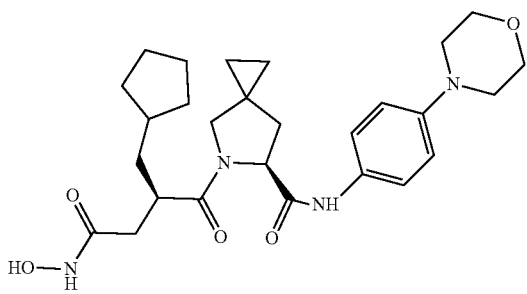 [SMILES: O=C(C[C@@H](CC1CCCC1)C(=O)N1CC2(CC2)C[C@H]1C(=O)Nc1ccc(N2CCOCC2)cc1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=302.05, $t_R$=1.06 min.

$^1$H NMR (400 MHz, DMSO) δ 10.82 (s, 1H), 7.52 (d, J=8.8 Hz, 2H), 6.93 (d, J=8.8 Hz, 2H), 4.55 (t, J=7.9 Hz, 1H), 3.78-3.67 (m, 4H), 3.19 (dd, J=37.9, 11.2 Hz, 2H), 3.08-3.02 (m, 4H), 2.33 (dd, J=12.9, 8.2 Hz, 1H), 2.01 (dd, J=12.9, 7.6 Hz, 1H), 0.78-0.53 (m, 4H).

$^{13}$C NMR (101 MHz, DMSO) δ 165.87, 147.72, 130.32, 120.50, 115.35, 66.04, 59.59, 51.66, 48.71, 37.81, 20.35, 10.34, 9.73.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 23%.

LC-MS (ESI): [M+1]$^+$=499.68, $t_R$=1.68 min.

$^1$H NMR (400 MHz, DMSO) δ 10.38 (s, 1H), 9.96-9.56 (m, 1H), 8.70 (s, 1H), 7.43 (t, J=8.7 Hz, 2H), 6.81 (t, J=44.5 Hz, 2H), 4.63-4.33 (m, 1H), 3.72 (s, 2H), 3.60 (dd, J=31.0, 9.4 Hz, 1H), 3.22 (d, J=11.5 Hz, 2H), 3.03 (d, J=3.8 Hz, 2H), 2.50 (s, 8H), 2.25-0.45 (m, 15H).

Example 62

Synthesis of (S)-5-((R)-2-(cyclopentylmethyl)-4-(hydroxylamino)-4-oxobutyl)-N-(pyrazin-2-yl)-5-azaspiro[2.4]heptane-6-amide

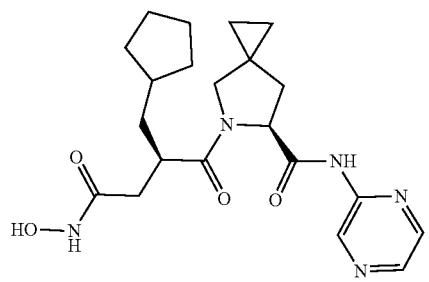 [SMILES: O=C(C[C@@H](CC1CCCC1)C(=O)N1CC2(CC2)C[C@H]1C(=O)Nc1cnccn1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.57 min.

$^1$H NMR (400 MHz, D$_2$O) δ 8.98 (d, J=96.9 Hz, 1H), 8.31 (t, J=81.8 Hz, 2H), 4.66-4.49 (m, 1H), 3.26-2.81 (m, 2H), 2.29-1.62 (m, 2H), 0.63-0.09 (m, 4H).

$^{13}$C NMR (101 MHz, D$_2$O) δ 148.55, 144.82, 137.12, 133.80, 60.43, 52.76, 37.11, 20.13, 9.77, 8.95, 8.64.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 27%.

LC-MS (ESI): [M+1]$^+$=416.59, $t_R$=1.59 min.

$^1$H NMR (400 MHz, CDCl$_3$) δ 10.15 (s, 1H), 8.46-7.88 (m, 3H), 4.78 (s, 1H), 3.88 (dd, J=28.6, 9.4 Hz, 1H), 3.64-3.39 (m, 1H), 3.24-2.54 (m, 3H), 2.08-1.91 (m, 1H), 1.87-1.17 (m, 12H), 0.81-0.46 (m, 4H).

Example 63

Synthesis of (S)-5-((R)-2-(cyclopentylmethyl)-4-(hydroxyamino)-4-oxobutyl)-N-(pyrimidin-4-yl-5-azaspiro[2.4]heptane-6-amide

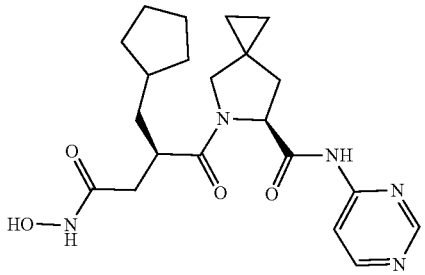 [SMILES: O=C(C[C@@H](CC1CCCC1)C(=O)N1CC2(CC2)C[C@H]1C(=O)Nc1ccncn1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=219.14, $t_R$=0.43 min.

$^1$H NMR (400 MHz, D$_2$O) δ 9.08 (s, 1H), 8.78 (d, J=6.8 Hz, 1H), 8.42 (t, J=31.2 Hz, 1H), 4.82 (dd, J=8.7, 6.4 Hz, 1H), 3.50-3.15 (m, 2H), 2.57-2.00 (m, 2H), 0.88-0.58 (m, 4H).

$^{13}$C NMR (101 MHz, D$_2$O) δ 169.77, 152.74, 150.17, 111.15, 60.98, 52.82, 36.76, 20.08, 9.91, 8.50.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 24%.

LC-MS (ESI): [M+1]$^+$=416.57, $t_R$=1.54 min.

$^1$H NMR (400 MHz, CDCl$_3$) δ 10.08 (s, 1H), 8.85 (s, 1H), 8.58 (t, J=5.0 Hz, 1H), 8.13 (s, 1H), 4.83 (s, 1H), 3.84 (d, J=9.8 Hz, 1H), 3.73-2.64 (m, 4H), 2.13 (d, J=5.8 Hz, 1H), 1.96-1.20 (m, 12H), 0.72-0.45 (m, 4H).

Example 64

Synthesis of (S)-5-((R)-2-(cyclopentylmethyl)-4-(hydroxyamino)-4-oxobutyl)-N-(5-fluoropyridin-2-yl)-5-azaspiro[2.4]heptane-6-amide

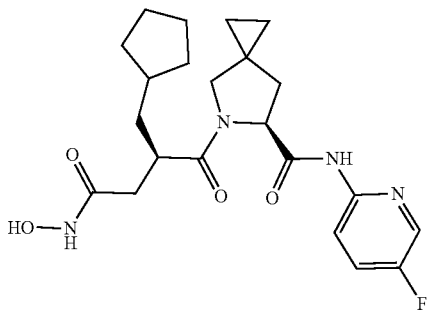 [SMILES: O=C(C[C@@H](CC1CCCC1)C(=O)N1CC2(CC2)C[C@H]1C(=O)Nc1ccc(F)cn1)NO]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=236.09, $t_R$=1.00 min.
$^1$H NMR (400 MHz, D$_2$O) δ 8.25 (s, 1H), 7.98-7.87 (m, 1H), 7.64 (dd, J=9.2, 3.9 Hz, 1H), 4.75-4.73 (m, 1H), 3.48-3.21 (m, 2H), 2.44 (dd, J=13.3, 9.0 Hz, 1H), 2.13 (dd, J=13.3, 6.4 Hz, 1H), 0.79-0.54 (m, 4H).
$^{13}$C NMR (101 MHz, D$_2$O) δ 169.10, 156.72 (d, $^1J_{C-F}$=250.3 Hz), 144.96, 131.48 (d, $^2J_{C-F}$=30.9 Hz), 131.10 (d, $^2J_{C-F}$=18.7 Hz), 118.14 (d, $^3J_{C-F}$=6.2 Hz).
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 18%.
LC-MS (ESI): [M+1]$^+$=433.56, $t_R$=1.56 min.
$^1$H NMR (400 MHz, CDCl$_3$) δ 9.60 (s, 1H), 8.36-7.72 (m, 2H), 7.43-7.12 (m, 1H), 4.82 (d, J=63.6 Hz, 1H), 3.88 (dd, J=25.2, 9.4 Hz, 1H), 3.27-2.40 (m, 4H), 2.01-1.86 (m, 1H), 1.85-1.18 (m, 12H), 0.72-0.50 (m, 4H).

Example 65

Synthesis of (S)-5-((R)-2-(cyclopentylmethyl)-4-(hydroxyamino)-4-oxobutyl)-N-(5-methylthiazol-2-yl)-5-azaspiro[2.4]heptane-6-amide

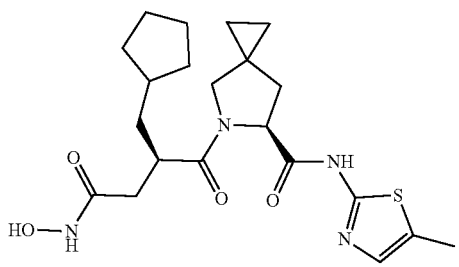 [SMILES: Cc1cnc(NC(=O)[C@@H]2CC3(CC3)CN2C(=O)[C@@H](CC(=O)NO)CC2CCCC2)s1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=238.45, $t_R$=1.09 min.
$^1$H NMR (400 MHz, D$_2$O) δ 7.24 (s, 1H), 4.77 (dd, J=8.9, 6.5 Hz, 1H), 3.24 (s, 2H), 2.38 (dd, J=13.4, 9.1 Hz, 1H), 2.28 (s, 3H), 2.05 (dd, J=13.4, 6.3 Hz, 1H), 0.72-0.45 (m, 4H).
$^{13}$C NMR (101 MHz, D$_2$O) δ 168.01, 159.21, 129.86, 124.06, 60.16, 52.75, 36.68, 20.02, 11.03, 9.78, 8.73.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 19%.
LC-MS (ESI): [M+1]$^+$=435.59, $t_R$=1.35 min.
$^1$H NMR (400 MHz, CDCl$_3$) δ 10.34 (s, 1H), 7.00 (s, 1H), 5.01-4.58 (m, 1H), 3.95-3.64 (m, 1H), 3.54 (d, J=10.0 Hz, 1H), 3.10-2.82 (m, 1H), 2.58-2.11 (m, 5H), 1.87-0.91 (m, 12H), 0.72-0.58 (m, 4H).

Example 66

Synthesis of (S)-5-((R)-2-(cyclopentylmethyl)-4-(hydroxyamino)-4-oxobutyl)-N-(pyridazin-3-yl)-5-spiro[2.4]heptane-6-carboxamide

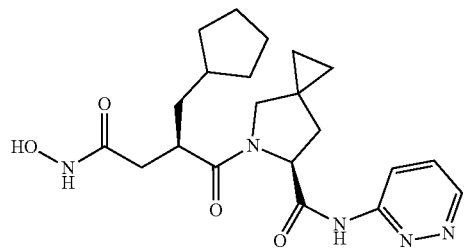 [SMILES: O=C(C[C@@H](CC1CCCC1)C(=O)N1CC2(CC2)C[C@H]1C(=O)Nc1cccnn1)NO]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=219.14, $t_R$=0.55 min.
$^1$H NMR (400 MHz, D$_2$O) δ 9.19 (d, J=5.0 Hz, 1H), 8.78 (d, J=9.2 Hz, 1H), 8.29 (dd, J=9.2, 5.2 Hz, 1H), 4.92-4.78 (m, 1H), 3.47-3.15 (m, 2H), 2.50 (dd, J=13.4, 9.1 Hz, 1H), 2.20 (dd, J=13.4, 6.3 Hz, 1H), 0.85-0.59 (m, 4H).
$^{13}$C NMR (101 MHz, D$_2$O) δ 169.33, 155.57, 145.59, 134.68, 128.12, 60.68, 52.82, 36.96, 20.13, 9.84, 8.65.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 20%.
LC-MS (ESI): [M+1]$^+$=416.59, $t_R$=1.48 min.
$^1$H NMR (400 MHz, CDCl$_3$) δ 11.83-9.51 (m, 2H), 9.12-8.70 (m, 1H), 8.46 (dd, J=30.4, 8.8 Hz, 1H), 7.69-7.34 (m, 1H), 5.44-4.71 (m, 1H), 4.31-0.87 (m, 18H), 0.83-0.17 (m, 4H).

Example 67

Synthesis of (S)-5-((R)-2-(cyclopentylmethyl)-4-(hydroxyamino)-4-oxobutyl)-N-(3-fluoropyridin-2-yl)-5-spiro[2.4]heptane-6-carboxamide

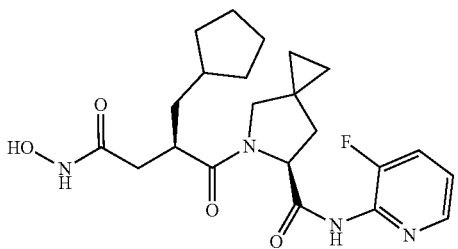 [SMILES: O=C(C[C@@H](CC1CCCC1)C(=O)N1CC2(CC2)C[C@H]1C(=O)Nc1ncccc1F)NO]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=235.90, t$_R$=0.60 min.
$^1$H NMR (400 MHz, D$_2$O) δ 8.20 (d, J=5.5 Hz, 1H), 8.06 (t, J=9.0 Hz, 1H), 7.56-7.50 (m, 1H), 4.90-4.79 (m, 1H), 3.31 (s, 2H), 2.61-2.39 (m, 1H), 2.15 (dd, J=13.4, 6.1 Hz, 1H), 0.76-0.54 (m, 4H).
$^{13}$C NMR (101 MHz, D$_2$O) δ 169.94, 150.12 (d, J=255.5 Hz), 138.18, 137.92 (d, J=13.4 Hz), 130.12 (d, J=16.9 Hz), 123.10 (d, J=5.8 Hz), 60.39, 52.83, 37.21, 20.06, 9.96, 8.50.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 20%.
LC-MS (ESI): [M+1]$^+$=433.56, t$_R$=1.49 min.
$^1$H NMR (400 MHz, CDCl$_3$) δ 10.25 (d, J=63.9 Hz, 1H), 9.75 (s, 1H), 8.23 (dd, J=59.2, 44.9 Hz, 1H), 7.45 (tq, J=16.9, 8.5 Hz, 1H), 7.09 (dd, J=26.9, 23.5 Hz, 1H), 4.82 (d, J=52.3 Hz, 1H), 4.04-3.29 (m, 2H), 3.02-0.93 (m, 16H), 0.92-0.31 (m, 4H).

Example 68

Synthesis of (S)-5-((R)-2-(cyclopentylmethyl)-4-(hydroxyamino)-4-oxobutyl)-N-cyclopropyl-5-azaspiro[2.4]heptane-6-carboxamide

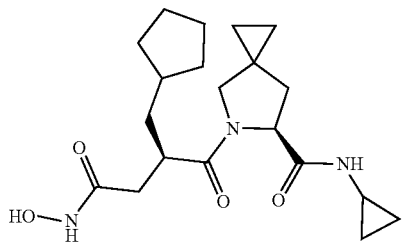 [SMILES: O=C(C[C@@H](CC1CCCC1)C(=O)N1CC2(CC2)C[C@H]1C(=O)NC1CC1)NO]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=182.98, t$_R$=0.550 min
$^1$H NMR (400 MHz, CDCl$_3$) δ 7.82 (s, 1H), 3.93 (dd, J=8.7, 5.2 Hz, 1H), 3.00-2.95 (m, 1H), 2.89 (s, 1H), 2.77-2.71 (m, 2H), 2.24-1.78 (m, 2H), 0.97-0.25 (m, 8H).
$^{13}$C NMR (101 MHz, CDCl$_3$) δ 175.92, 60.94, 54.70, 39.27, 22.37, 22.09, 11.00, 9.48, 6.30, 6.27.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 25%.
LC-MS (ESI): [M+1]$^+$=378.59, t$_R$=1.49 min.
$^1$H NMR (400 MHz, DMSO) δ 10.37 (d, J=8.2 Hz, 1H), 8.88-8.46 (m, 1H), 7.89-7.36 (m, 1H), 4.55-4.09 (m, 1H), 3.69-3.37 (m, 2H), 3.38-3.26 (m, 2H), 3.25-2.89 (m, 1H), 2.87-2.55 (m, 2H), 2.42-2.12 (m, 1H), 2.08-1.81 (m, 2H), 1.80-1.24 (m, 9H), 1.00-0.24 (m, 8H).

Example 69

Synthesis of (S)-5-((R)-2-(cyclopentylmethyl)-4-(hydroxyamino)-4-oxobutyl)-N-(oxazol-2-yl)-5-spiro[2.4]heptane-6-carboxamide

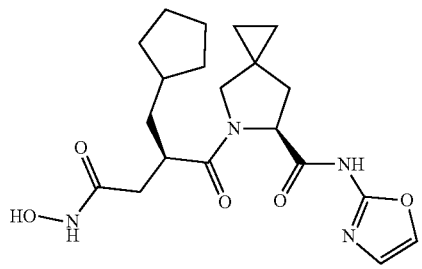 [SMILES: O=C(C[C@@H](CC1CCCC1)C(=O)N1CC2(CC2)C[C@H]1C(=O)Nc1ncco1)NO]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=208.32, t$_R$=0.36 min.
$^1$H NMR (400 MHz, DMSO) δ 10.77 (s, 1H), 7.95 (s, 1H), 7.19 (s, 1H), 4.64 (s, 1H), 3.19 (dd, J=12.2, 6.2 Hz, 2H), 2.38 (dd, J=12.9, 8.5 Hz, 1H), 2.01 (dd, J=12.8, 6.7 Hz, 1H), 0.67 (d, J=9.3 Hz, 4H).
$^{13}$C NMR (101 MHz, DMSO) δ 167.30, 152.62, 136.22, 125.77, 59.63, 51.56, 37.35, 20.08, 10.36, 9.71.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 25%.
LC-MS (ESI): [M+1]$^+$=405.49, t$_R$=1.48 min.
$^1$H NMR (400 MHz, CDCl$_3$) δ 7.60 (s, 1H), 7.15 (s, 1H), 5.07 (s, 1H), 3.63-3.00 (m, 3H), 2.89-2.39 (m, 3H), 1.93-1.19 (m, 12H), 0.62-0.48 (m, 4H).

Example 70

Synthesis of (S)-5-((R)-2-(cyclopentylmethyl)-4-(hydroxyamino)-4-oxobutyl)-N-(isoxazol-5-yl)-5-spiro[2.4]heptane-6-carboxamide

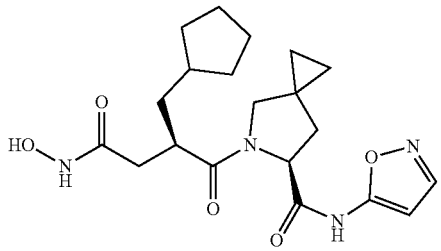 [SMILES: O=C(C[C@@H](CC1CCCC1)C(=O)N1CC2(CC2)C[C@H]1C(=O)Nc1ccno1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=208.32, $t_R$=0.36 min.

$^1$H NMR (400 MHz, DMSO) δ 10.77 (s, 1H), 7.95 (s, 1H), 7.19 (s, 1H), 4.64 (s, 1H), 3.19 (dd, J=12.2, 6.2 Hz, 2H), 2.38 (dd, J=12.9, 8.5 Hz, 1H), 2.01 (dd, J=12.8, 6.7 Hz, 1H), 0.67 (d, J=9.3 Hz, 4H).

$^{13}$C NMR (101 MHz, DMSO) δ 167.30, 152.62, 136.22, 125.77, 59.63, 51.56, 37.35, 20.08, 10.36, 9.71.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 20%.

LC-MS (ESI): [M+1]$^+$=405.46, $t_R$=1.53 min.

$^1$H NMR (400 MHz, CDCl$_3$) δ 11.40-9.93 (m, 1H), 8.54-7.96 (m, 1H), 6.56-6.17 (m, 1H), 4.92-4.22 (m, 1H), 4.11-3.12 (m, 2H), 3.10-0.92 (m, 15H), 0.91-0.22 (m, 4H).

Example 71

Synthesis of (S)-5-((R)-2-(cyclopentylmethyl)-4-(hydroxyamino)-4-oxobutyl)-N-(5-methylisoxazol-3-yl)-5-spiro[2.4]heptane-6-carboxamide

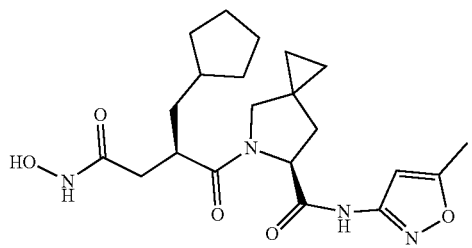 [SMILES: Cc1cc(NC(=O)[C@@H]2CC3(CC3)CN2C(=O)[C@@H](CC(=O)NO)CC2CCCC2)no1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=221.79, $t_R$=0.93 min.

$^1$H NMR (400 MHz, DMSO) δ 10.71 (s, 1H), 6.62 (s, 1H), 4.56 (s, 1H), 3.17 (d, J=11.9 Hz, 2H), 2.39 (s, 2H), 2.33 (dd, J=12.8, 8.5 Hz, 1H), 1.98 (dd, J=12.9, 7.0 Hz, 1H), 0.65 (d, J=14.3 Hz, 4H).

$^{13}$C NMR (101 MHz, DMSO) δ 170.05, 167.12, 157.36, 96.21, 59.47, 51.57, 37.49, 20.16, 12.10, 10.16, 9.88.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 45%.

LC-MS (ESI): [M+1]$^+$=419.59, $t_R$=1.32 min.

$^1$H NMR (400 MHz, CDCl$_3$) δ 10.80-9.61 (m, 2H), 7.27 (s, 1H), 6.83-6.31 (m, 1H), 5.32 (d, J=16.2 Hz, 1H), 4.76 (d, J=35.4 Hz, 1H), 4.32-1.82 (m, 12H), 1.79-1.10 (m, 6H), 1.06-0.20 (m, 6H).

Example 72

Synthesis of (S)-5-((R)-2-(cyclopentylmethyl)-4-(hydroxyamino)-4-oxobutanoyl)-N-(thiazol-2-yl)-5-azaspiro[2.4]heptane-6-carboxamide

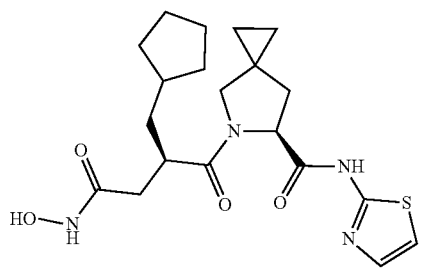

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.38, $t_R$=0.92 min.

$^1$H NMR (400 MHz, DMSO) δ 10.84 (s, 1H), 7.53 (d, J=3.1 Hz, 1H), 7.34 (d, J=3.2 Hz, 1H), 4.79-4.59 (m, 1H), 3.21 (ddd, J=15.7, 10.7, 5.6 Hz, 2H), 2.37 (dd, J=12.9, 8.4 Hz, 1H), 2.03 (dd, J=13.0, 6.9 Hz, 1H), 0.77-0.57 (m, 4H).

$^{13}$C NMR (101 MHz, DMSO) δ 167.07, 157.46, 137.44, 114.41, 59.19, 51.59, 37.46, 20.16, 10.22, 9.94.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 21%.

LC-MS (ESI): [M+1]$^+$=421.46, $t_R$=1.46 min.

$^1$H NMR (400 MHz, DMSO) δ 12.13 (s, 1H), 10.35 (d, J=21.1 Hz, 1H), 8.87-8.56 (m, 1H), 7.46 (d, J=3.2 Hz, 1H), 7.20 (d, J=3.2 Hz, 1H), 4.65 (t, J=7.0 Hz, 1H), 3.80-3.41 (m, 2H), 2.99-2.75 (m, 1H), 2.23 (dd, J=14.7, 8.7 Hz, 1H), 2.11-1.95 (m, 2H), 1.92-1.63 (m, 4H), 1.50 (ddd, J=27.3, 13.9, 6.3 Hz, 5H), 1.21 (dd, J=13.7, 7.3 Hz, 2H), 1.04 (ddd, J=19.6, 11.1, 7.4 Hz, 2H), 0.76-0.59 (m, 3H), 0.58-0.45 (m, 2H).

Example 73

Synthesis of (S)-5-((R)-2-(cyclopentylmethyl)-4-(hydroxyamino)-4-oxobutyl)-N-(5-(trifluoromethyl)thiazol-2-yl)5-spiro[2.4]heptane-6-carboxamide

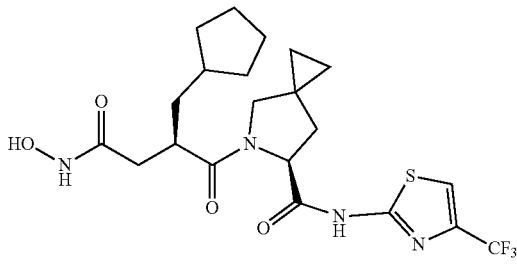 [SMILES: O=C(C[C@@H](CC1CCCC1)C(=O)N1CC2(CC2)C[C@H]1C(=O)Nc1nc(C(F)(F)F)cs1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=292.22, $t_R$=1.28 min $^1$H NMR (400 MHz, DMSO) δ 10.46 (s, 1H), 8.09 (d, J=0.9 Hz, 1H), 4.67 (dd, J=8.1, 7.0 Hz, 1H), 3.26-3.17 (m, 2H), 2.36 (dd, J=13.2, 8.5 Hz, 1H), 2.06 (dd, J=13.2, 6.6 Hz, 1H), 0.76-0.61 (m, 4H).

$^{13}$C NMR (101 MHz, DMSO) δ 167.88, 159.26, 121.96, 119.23, 117.58, 59.25, 51.77, 37.12, 20.13, 10.32, 9.60.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 20%.

LC-MS (ESI): [M+1]$^+$=489.17, $t_R$=2.12 min.

$^1$H NMR (400 MHz, CDCl$_3$) δ 13.14-11.09 (m, 1H), 10.14 (d, J=58.3 Hz, 1H), 7.44 (dd, J=111.4, 81.1 Hz, 2H), 5.29-4.55 (m, 1H), 4.17-3.27 (m, 2H), 3.24-2.51 (m, 2H), 2.48-0.84 (m, 14H), 0.82-0.28 (m, 3H).

Example 74

Synthesis of (S)-5-((R)-2-(cyclopentylmethyl)-4-(hydroxyamino)-4-oxobutyl)-N-(1,3,4-thiadiazol-2-yl)-5-azaspiro[2.4]heptane-6-carboxamide

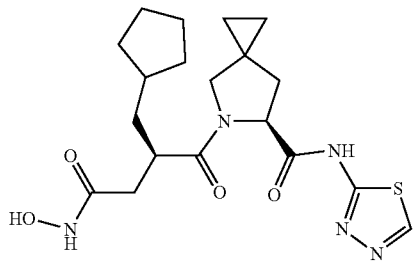 [SMILES: O=C(C[C@@H](CC1CCCC1)C(=O)N1CC2(CC2)C[C@H]1C(=O)Nc1nncs1)NO]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=224.87, $t_R$=0.63 min.

$^1$H NMR (400 MHz, DMSO) δ 10.85 (dd, J=52.8, 47.6 Hz, 1H), 9.13 (t, J=28.8 Hz, 1H), 4.96-4.50 (m, 1H), 3.47-2.92 (m, 2H), 2.46-1.89 (m, 2H), 1.15-0.23 (m, 4H).

$^{13}$C NMR (101 MHz, DMSO) δ 167.60, 158.24, 149.57, 59.31, 51.59, 37.35, 20.10, 10.31, 9.77.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 23%.

LC-MS (ESI): [M+1]$^+$=422.14, $t_R$=1.58 min.

$^1$H NMR (400 MHz, DMSO) δ 12.64 (s, 1H), 10.35 (d, J=21.9 Hz, 1H), 9.36-9.02 (m, 1H), 8.96-8.41 (m, 1H), 4.89-4.51 (m, 1H), 2.25-1.98 (m, 2H), 1.95-0.95 (m, 12H), 0.94-0.24 (m, 4H).

Example 75

Synthesis of (R)-4-((S)-6-(1H-benzimidazol-2-yl)-5-azaspiro[2.4]heptane-5-yl)-3-(cyclopentylmethyl)-N-hydroxy-4-oxobutanamide

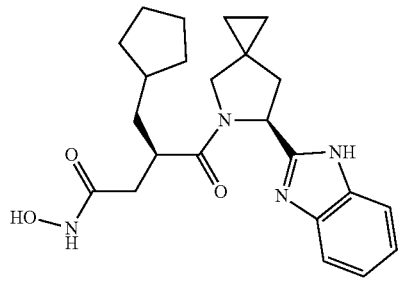 [SMILES: O=C(C[C@@H](CC1CCCC1)C(=O)N1CC2(CC2)C[C@H]1c1nc2ccccc2[nH]1)NO]

Step 1: The procedure was the same as the Step 1 in Example 1.

Step 2: The procedure was the same as the Step 2 in Example 1.

Step 3: The procedure was the same as the Step 3 in Example 1.

LC-MS (ESI): [M+1]$^+$=214.16, $t_R$=0.94 min.

$^1$H NMR (400 MHz, D$_2$O) δ 7.67-7.58 (m, 2H), 7.49-7.39 (m, 2H), 5.41 (t, J=8.6 Hz, 1H), 3.55-3.46 (m, 1H), 3.25-3.15 (m, 1H), 2.68-2.57 (m, 1H), 2.39-2.28 (m, 1H), 0.85-0.60 (m, 4H).

$^{13}$C NMR (101 MHz, D$_2$O) δ 144.90, 130.95, 127.05, 114.21, 36.52, 20.20, 11.92, 7.25.

Step 4: The procedure was the same as the Step 3 in the synthesis of the general formula (X2).

Step 5: The procedure was the same as the Step 4 in the synthesis of the general formula (X2).

Step 6: The procedure was the same as the Step 5 in the synthesis of the general formula (X2), and the three-step yield was 16%.

LC-MS (ESI): [M+1]$^+$=411.53, $t_R$=1.34 min.

$^1$H NMR (400 MHz, CDCl$_3$) δ 7.97-7.47 (m, 2H), 7.49-7.28 (m, 1H), 7.21 (dd, J=15.3, 12.4 Hz, 2H), 5.66-5.29 (m, 1H), 3.93-3.26 (m, 2H), 3.18-2.90 (m, 2H), 2.87-2.58 (m, 1H), 2.55-2.10 (m, 2H), 1.94-0.99 (m, 11H), 0.81-0.25 (m, 4H).

Example 76

Synthesis of (R)-4-((R)-6-(1H-benzimidazol-2-yl)-5-azaspiro[2.4]heptane-5-yl)-3-(cyclopentylmethyl)-N-hydroxy-4-oxobutanamide

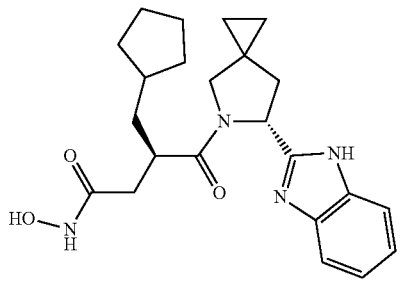 [SMILES: O=C(C[C@@H](CC1CCCC1)C(=O)N1CC2(CC2)C[C@@H]1c1nc2ccccc2[nH]1)NO]

Rotamers Prepared and Isolated

LC-MS (ESI): [M+1]$^+$=411.53, $t_R$=1.32 min.

$^1$H NMR (400 MHz, CDCl$_3$) δ 12.46 (s, 1H), 7.53 (s, 2H), 7.16 (s, 2H), 5.25 (s, 1H), 3.84 (s, 1H), 2.98 (d, J=42.9 Hz, 2H), 2.74-2.31 (m, 3H), 2.08 (s, 1H), 1.88-1.06 (m, 11H), 0.69-0.52 (m, 4H).

Example 77

Synthesis of (S)-2-((R)-2-(2-(hydroxyamino)-2-oxoethyl)hexanoyl)-N-(pyrazin-2-yl-2-azaspiro[4.4]nonane-3-carboxamide

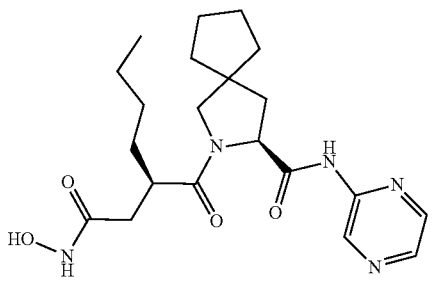 [SMILES: CCCC[C@H](CC(=O)NO)C(=O)N1CC2(CCCC2)C[C@H]1C(=O)Nc1cnccn1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=246.92, $t_R$=1.02 min.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 23%.

LC-MS (ESI): [M+1]$^+$=418.5, $t_R$=1.38 min.

$^1$H NMR (400 MHz, DMSO) δ 11.17-10.66 (m, 1H), 10.24 (d, J=95.0 Hz, 1H), 9.30 (s, 1H), 8.38 (d, J=17.7 Hz, 2H), 4.69-4.37 (m, 1H), 3.95-3.06 (m, 2H), 3.02-2.64 (m, 1H), 2.42-1.76 (m, 4H), 1.74-0.43 (m, 17H).

Example 78

Synthesis of (S)—N-(5-fluoropyridin-2-yl)-2-((R)-2-(2-(hydroxyamino)-2-oxoethyl)hexanoyl)-2-spiro[4.4]nonane-3-carboxamide

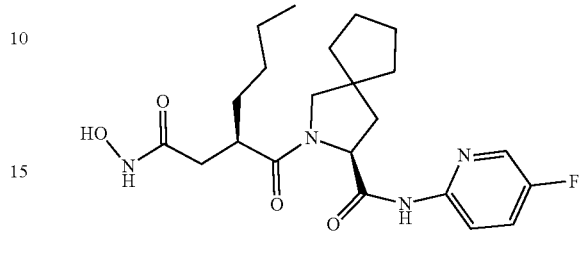

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=263.93, $t_R$=1.28 min.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 20%.

LC-MS (ESI): [M+1]$^+$=435.18, $t_R$=2.03 min.

$^1$H NMR (400 MHz, CDCl$_3$) δ 9.77 (d, J=529.3 Hz, 2H), 7.82-6.38 (m, 2H), 4.73 (s, 1H), 3.96-2.84 (m, 3H), 2.63-1.91 (m, 6H), 1.89-0.45 (m, 17H).

Example 79

Synthesis of (S)-2-((R)-2-(2-(hydroxyamino)-2-oxoethyl)hexanoyl)-N-(5-methylthiazol-2-yl)-2-azaspiro[4.4]nonane-3-amide

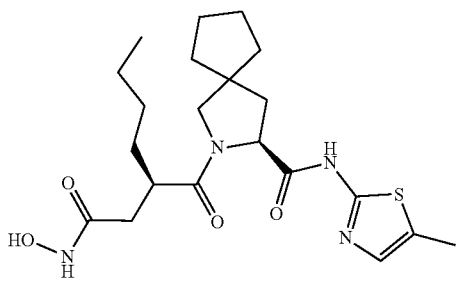 [SMILES: CCCC[C@H](CC(=O)NO)C(=O)N1CC2(CCCC2)C[C@H]1C(=O)Nc1ncc(C)s1]

Step 1: The procedure was the same as the Step 1 in the synthesis of the general formula (X1).

Step 2: The procedure was the same as the Step 2 in the synthesis of the general formula (X1).

LC-MS (ESI): [M+1]$^+$=268.09, $t_R$=1.21 min.

Step 3: The procedure was the same as the Step 3 in the synthesis of the general formula (X2).

Step 4: The procedure was the same as the Step 4 in the synthesis of the general formula (X2).

Step 5: The procedure was the same as the Step 5 in the synthesis of the general formula (X2), and the three-step yield was 21%.

LC-MS (ESI): [M+1]$^+$=437.39, $t_R$=2.02 min. $^1$H NMR (400 MHz, CDCl$_3$) δ 7.18 (s, 1H), 5.25 (s, 1H), 3.36-3.28 (m, 2H), 3.13-3.08 (m, 1H), 2.63 (dd, J=24.7, 10.3 Hz, 1H), 2.51-2.31 (m, 4H), 1.87-1.13 (m, 16H), 0.89 (s, 3H).

Example 80

Synthesis of (S)-2-((R)-2-(2-(hydroxyamino)-2-oxoethyl)hexanoyl)-N-(5-methylisoxazol-3-yl)-2-spiro[4.4]nonane-3-carboxamide

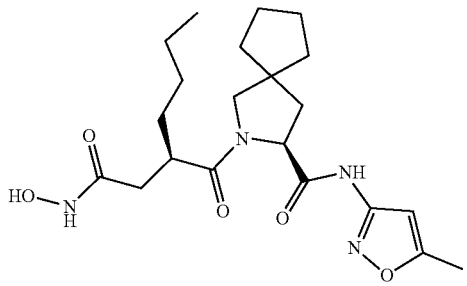 [SMILES: CCCC[C@H](CC(=O)NO)C(=O)N1CC2(CCCC2)C[C@H]1C(=O)Nc1cc(C)on1]

Step 1: The procedure was the same as the Step 1 in the synthesis of the general formula (X1).
Step 2: The procedure was the same as the Step 2 in the synthesis of the general formula (X1).
LC-MS (ESI): [M+1]$^+$=249.23, $t_R$=0.98 min.
$^1$H NMR (400 MHz, DMSO) δ 10.71 (s, 1H), 6.62 (s, 1H), 4.56 (s, 1H), 3.17 (d, J=11.9 Hz, 2H), 2.39 (s, 2H), 2.33 (dd, J=12.8, 8.5 Hz, 1H), 1.98 (dd, J=12.9, 7.0 Hz, 1H), 0.65 (d, J=14.3 Hz, 4H).
$^{13}$C NMR (101 MHz, DMSO) δ 170.05, 167.12, 157.36, 96.21, 59.47, 51.57, 37.49, 20.16, 12.10, 10.16, 9.88.
Step 3: The procedure was the same as the Step 3 in the synthesis of the general formula (X2).
Step 4: The procedure was the same as the Step 4 in the synthesis of the general formula (X2).
Step 5: The procedure was the same as the Step 5 in the synthesis of the general formula (X2), and the three-step yield was 30%.
LC-MS (ESI): [M+1]$^+$=421.31, $t_R$=1.49 min.
$^1$H NMR (400 MHz, DMSO) δ 10.88 (s, 1H), 6.62 (d, J=31.4 Hz, 1H), 4.48-4.05 (m, 1H), 3.33 (s, 8H), 2.50 (dt, J=3.5, 1.7 Hz, 9H), 1.87-0.99 (m, 8H), 0.96-0.73 (m, 2H).

Control Experiment 1

Compounds B and C were from patents CN101584694A and CN101869563A.

TABLE 8

| Effect of the introduction of three-membered ring on activity | | |
|---|---|---|
| item | A | B |
| Structure | (structure shown) 0.5 | (structure shown) 1 |
| Measured MIC | 8.7015 | 7.9033 |
| Sybyl score | | |
| item | C | D |
| Structure | (structure shown) 0.5 | (structure shown) 0.125 |
| Measured MIC | 8.7192 | 8.8965 |
| Sybyl score | | |

Sybyl score is given using the scoring function of the Sybyl X2 software. The higher the score, the lower the predicted minimum inhibitory concentration. Combined with the minimum inhibitory concentration measured in the experiment, it was not difficult to find that the effect of the introduction of three-membered ring on the activity was obvious.

Control Experiment 2

Because PDF inhibitors such as LBM415 and GSK1322322 can produce active species such as aromatic hydroxylamine and aromatic hydrazines in metabolic process, and cause human methemoglobinemia. To this end, continuous wavelength method was adopted in this invention to scan the absorption spectrum of blood samples in the wavelength range of 500 to 700 nm in the ultraviolet-visible spectrophotometer, and the contents of methemoglobin in blood samples of three healthy volunteers were calculated, after being effected by the synthesized compounds.

Experimental materials: Nicotinamide adenine dinucleotide phosphate (NADPH) reduction system: glucose-6-disodium phosphate, nicotinamide adenine dinucleoside phosphate and glucose-6-phosphate dehydrogenase (purchased from Shanghai yuanye Bio-Technology Co., Ltd) were added to 1 mL of phosphate buffer solution (PBS, pH 7.4), and the mixture was shaked in a shaker type water bath at 37° C. for 10 min, and then cooled to 0° C. Mixed human hepatocytes fraction S9 was purchased from Xenotech (20 mg S9 protein/1 mL suspension medium). Compounds were prepared to stock solution at a concentration of 50 mM, which was stored at −20° C. for use. Dapsone was used as positive control experimental reagent, which was purchased from Sigma Aldrich. 1% w/v triton X-100 was self-prepared. Blood samples were collected using Vacutainer tubes containing EDTA anticoagulants (BD, Franklin Lakes, USA), which were sampled from three healthy volunteers and used immediately after sampling.

Preparation of incubation system for blood samples and drugs: 250 μL of incubation system was consist of 220 μL of whole blood, 25 μL of S9 (final concentration: 2 mg S9 protein/mL incubation solution), 2.5 μL of NADPH form system (final concentration: 10 mM G-6-P, 1 mM NADP, 7.5 Units/mL) and 2.5 μL of stock solution of a compound (final concentration 500 μM). 2 mL of incubation system was placed in an Eppendorf tube and incubated for 5 hours at 37° C. in water bath.

Determination of the content of methemoglobin: 60 μL of an incubated sample was taken and lysed with 3.0 mL of 1% Triton X-100. The content of methemoglobin (MetHb) was measured by an ultraviolet-visible spectrophotometer, with the Triton X-100 solution used as blank control. A sample was placed in a cuvette, 1 minute later, the spectrums of the sample in the wavelength range from 500 nm to 700 nm were recorded. The sample was added with 2 mg of potassium ferricyanide, and was allowed to stay stationary for 2 minutes for completely oxidization of ferrous iron in the sample, and standard spectrum of methemoglobin with saturated potassium ferricyanide. The percentage of methemoglobin formation (MetHb %) was obtained by the ratio of absorbance at 630 nm. MetHb %=(A'−AB')/AM', wherein, A' was the total absorbance of the sample at 630 nm, AB' was the base absorbance of the reduced blood in the sample at 630 nm, and AM' was the absorbance of oxidized blood with saturated potassium ferricyanide at 630 nm.

TABLE 9

Evaluation of toxicity of the compounds on methemoglobin in vitro

| Compounds in Examples | MetHb % (n = 3) |
|---|---|
| Test of whole blood immediately after sampling | 1.00 ± 0.02 |
| Whole blood incubated without being added with drugs | 1.10 ± 0.07 |
| Example 2 | 3.32 ± 0.05 |
| Example 3 | 3.33 ± 0.06 |
| Example 6 | 2.25 ± 0.02 |
| Example 7 | 2.24 ± 0.05 |
| Example 8 | 4.12 ± 0.07 |
| Example 9 | 1.13 ± 0.06 |
| Example 10 | 1.12 ± 0.01 |
| Example 11 | 1.26 ± 0.07 |
| Example 12 | 1.22 ± 0.02 |
| Example 13 | 1.15 ± 0.06 |
| LBM415 | 3.05 ± 0.01 |
| GSK1322322 | 3.00 ± 0.02 |

The results of toxicity test in vitro showed that, compared with the control drugs LBM415 and GSK1322322, the synthesized spiro three-membered compounds 2, 3, 6, 7, 8 and 9 had lower probability of methemoglobin formation in blood; and the toxicity of the amide bioelectron isostere azole compounds was very low.

Control Experiment 3

TABLE 10

Comparison of MICs of Compounds in Examples and Control Compound against Gram-negative bacteria *Moraxella catarrhalis*

| Gram-negative bacteriuma | Example 22 | Example 33 | LBM415 |
|---|---|---|---|
| *Moraxella catarrhalis* (n = 7) MIC, μg/mL | 0.06-0.5 | 0.06-0.25 | 0.5-2 |

Compared with the control compound, the synthesized compounds had markedly improved anti-bacterial activity against the Gram-negative bacteria *Moraxella catarrhalis*.

The invention claimed is:

1. A Spiro three-membered ring, Spiro five-membered ring peptide deformylase inhibitor, wherein the structure of the inhibitor is represented by the following formula (1):

formula (1)

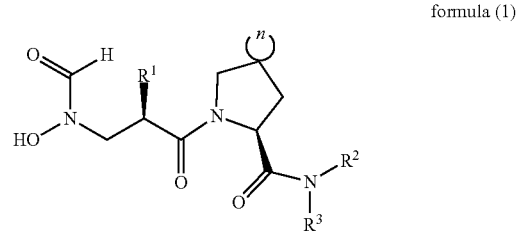

in the formula (1), n=2-4; $R^1$ is n-butyl or cyclopentylmethyl; $R^2$ is selected from aromatic ring, aromatic heterocyclic ring, heterocyclic ring, or alkyl; and $R^3$ is hydrogen or alkyl.

2. The inhibitor according to claim 1, wherein, in the formula (1), n=2 or 4; $R^1$ is n-butyl or cyclopentylmethyl; $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2- yl, 5-methylthiazol-2-yl, 3-(pyridin-3-yl)phenyl, N-(pyrimidin-2-yl)phenyl-1-amino-3-yl, 4-(pyridin-3-yl)pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, benzothiazol-2-yl, 3-methyl formate-2-thienyl; and $R^3$ is hydrogen.

3. A spiro three-membered ring, spiro five-membered ring peptide deformylase inhibitor, wherein the structure of the inhibitor is represented by the following formula (2):

formula (2)

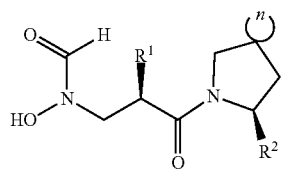

in the formula (2), n=2-4, $R^1$ is n-butyl or cyclopentylmethyl; $R^2$ is aromatic ring, or aromatic heterocyclic ring.

4. The inhibitor according to claim 3, wherein, in the formula (2), n=2 or 4; $R^1$ is n-butyl or cyclopentylmethyl; and $R^2$ is 2-benzimidazolyl, 1,3,4-oxadioxazole, 1,2,4-oxadioxazole, or 1,3,4-triazole.

5. A spiro three-membered ring, spiro five-membered ring peptide deformylase inhibitor, wherein the structure of the inhibitor is represented by the following formula (3):

formula (3)

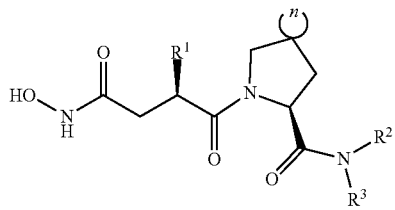

in the formula (3), n=2-4; $R^1$ is n-butyl or cyclopentylmethyl; $R^2$ is aromatic ring, aromatic heterocyclic ring, heterocyclic ring, or alkyl; and $R^3$ is hydrogen or alkyl.

6. The inhibitor according to claim 5, wherein, in the formula (3), n=2 or 4; $R^1$ is n-butyl or cyclopentylmethyl; and $R^2$ is selected from 1H-pyrazol-3-yl, 5-fluoropyridin 1-oxide-2-yl, 5-(tert-butyl)isoxazol-3-yl, 6-methyl-N-(4-(pyridin-3-yl)pyrimidin-2-yl)phenyl-1-amino-3-yl, 3-fluoropyridin-2-yl, 5-methylthiazol-2-yl, 3-(pyridin-3-yl)phenyl, N-(pyrimidin-2-yl)phenyl-1-amino-3-yl, 4-(pyridin-3-yl)pyrimidin-2-yl, 4-morpholine phenyl, 2-pyrazinyl, 3-pyridazinyl, 4-pyrimidinyl, 1-methyl-1H-pyrazol-4-yl, 5-isoxazolyl, 4-methylthiazol-2-yl, 2-oxazolyl, 5-methylisoxazol-3-yl, 2-thiazolyl, 1,3,4-thiadiazol-2-yl, 5-(trifluoromethyl)thiazol-2-yl, benzothiazol-2-yl, or 3-methyl formate-2-thienyl; and $R^3$ is hydrogen.

7. A spiro three-membered ring, spiro five-membered ring peptide deformylase inhibitor, wherein the structure of the inhibitor is represented by the following formula (4):

formula (4)

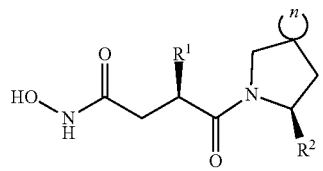

in the formula (4), n=2-4; $R^1$ is n-butyl or cyclopentylmethyl; and $R^2$ is aromatic ring, or aromatic heterocyclic ring.

8. The inhibitor according to claim 7, wherein, in the formula (4), n=2 or 4; $R^1$ is n-butyl or cyclopentylmethyl; and $R^2$ is 2-benzimidazolyl, 1,3,4-oxodioxazole, 1,2,4-oxodioxazole, or 1,3,4-triazole.

9. A spiro three-membered ring, spiro five-membered ring peptide deformylase inhibitor selected from the group consisting of:

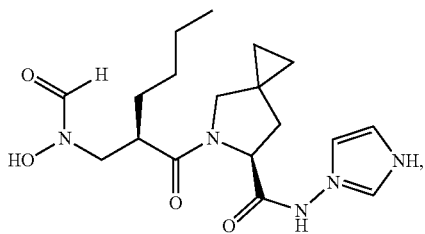

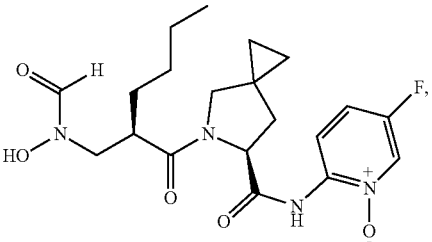

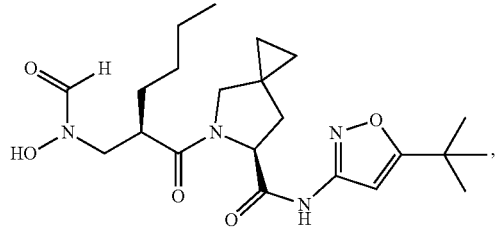

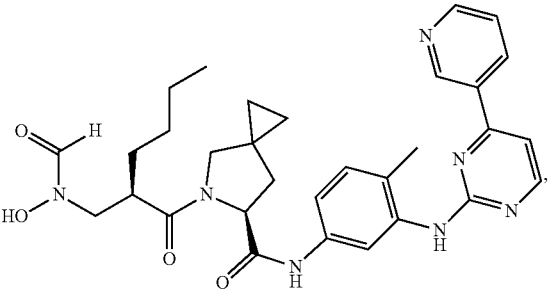

143 -continued
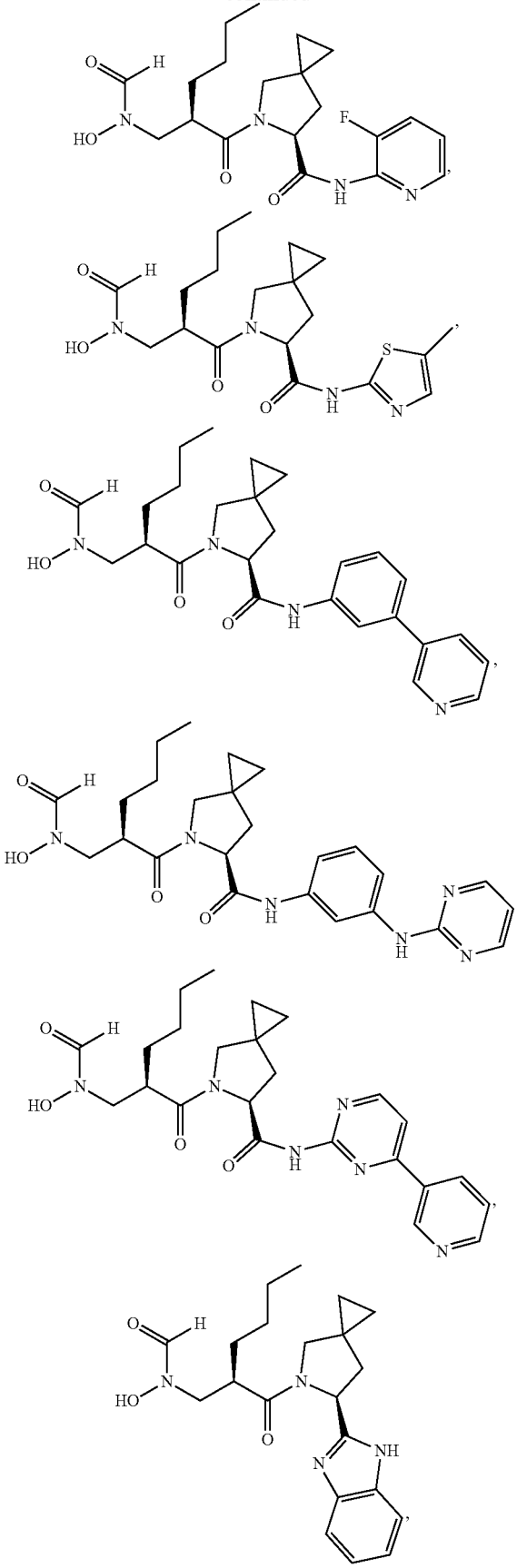
144 -continued
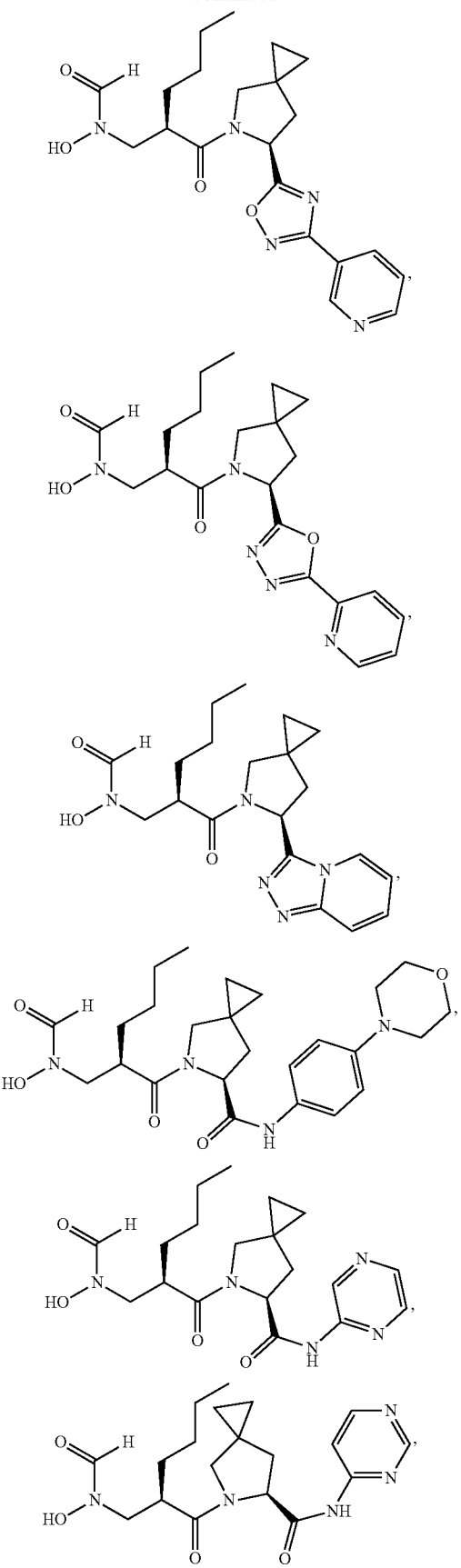

-continued
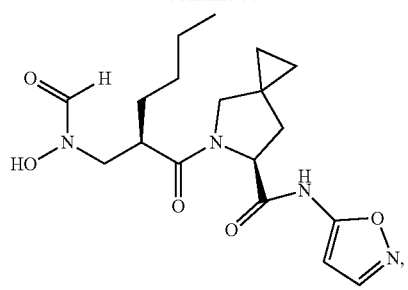
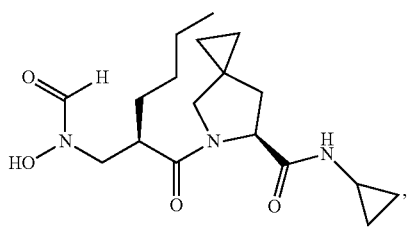
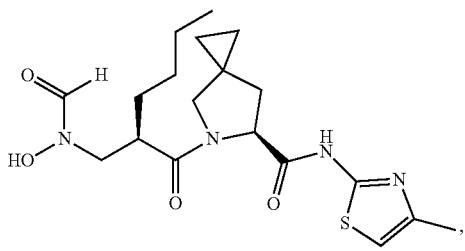
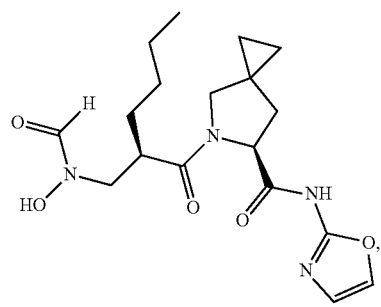
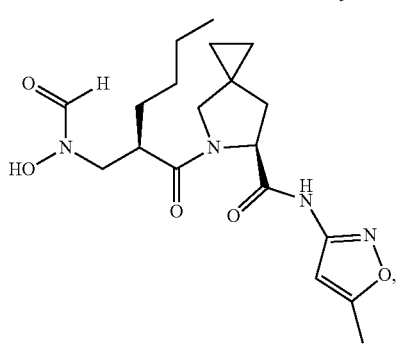
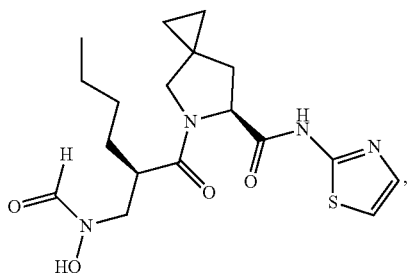
-continued
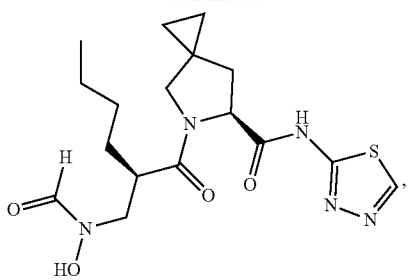
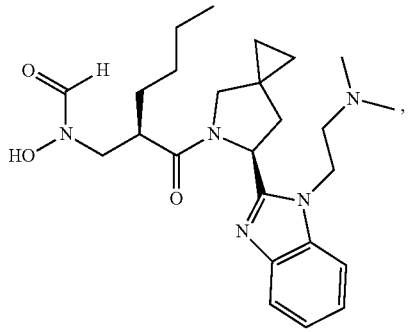
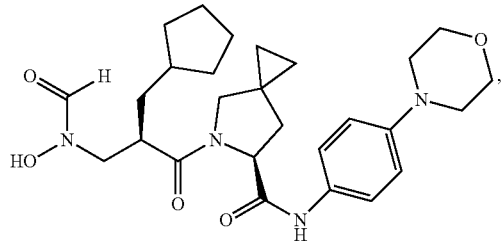
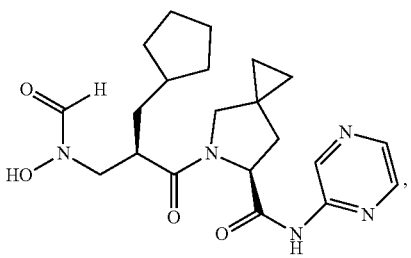
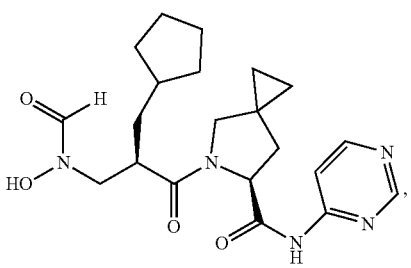
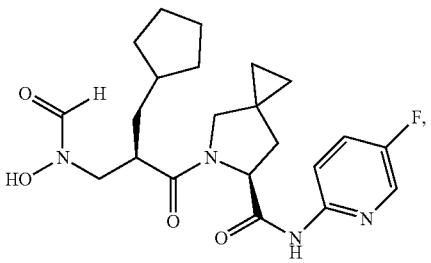

-continued
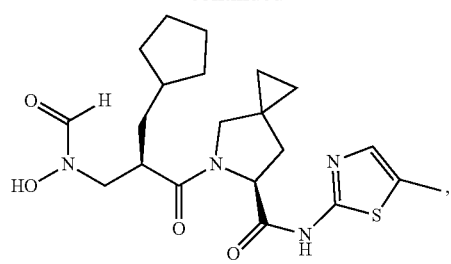
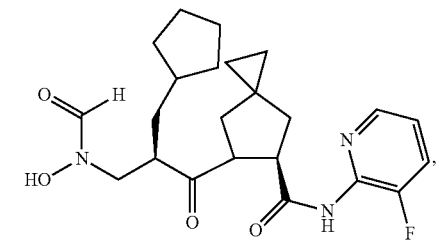
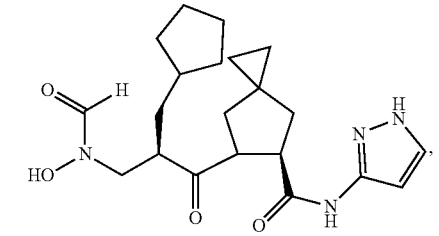
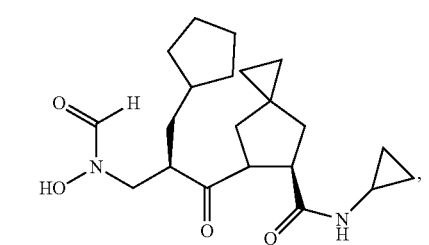
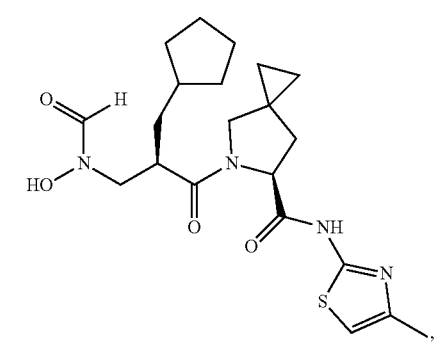
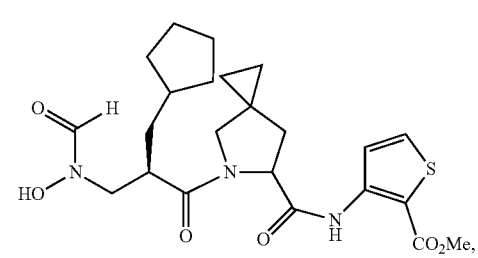
-continued
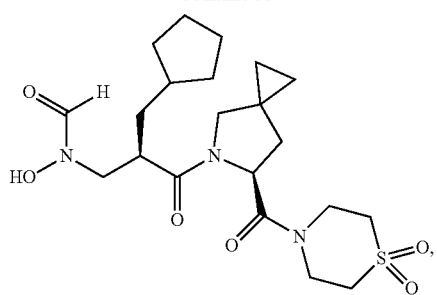
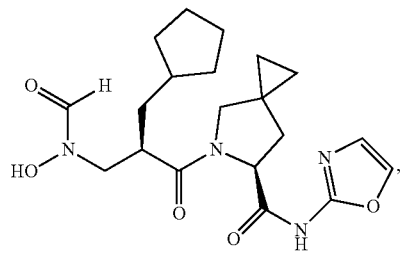
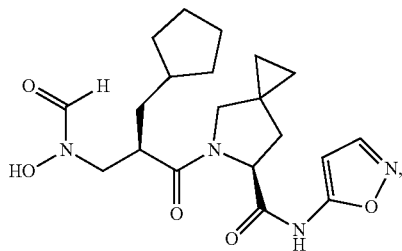
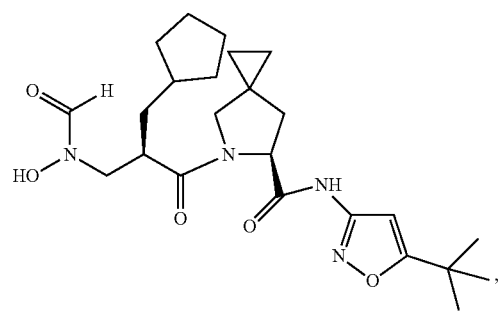
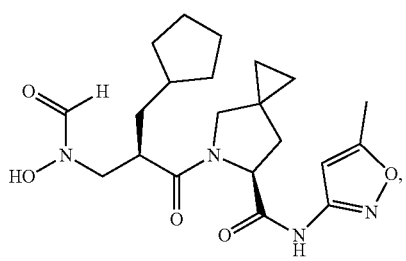
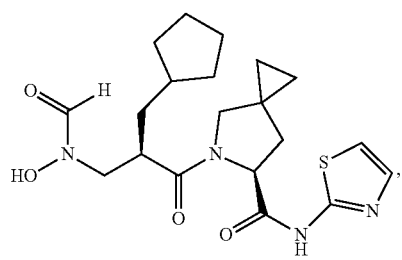

149
-continued
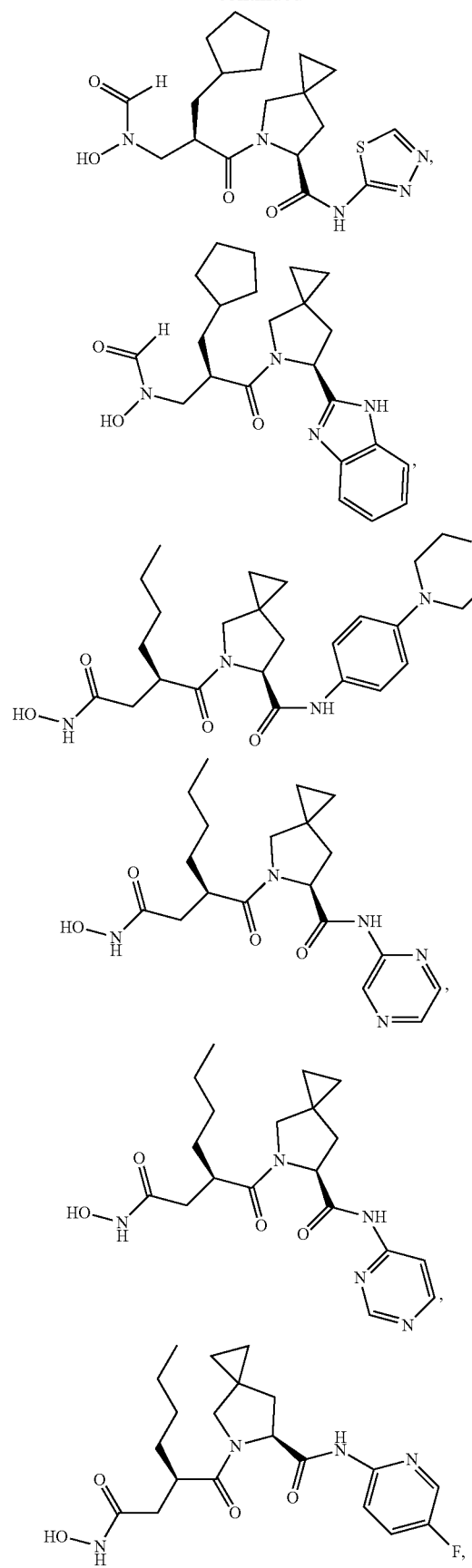
150
-continued
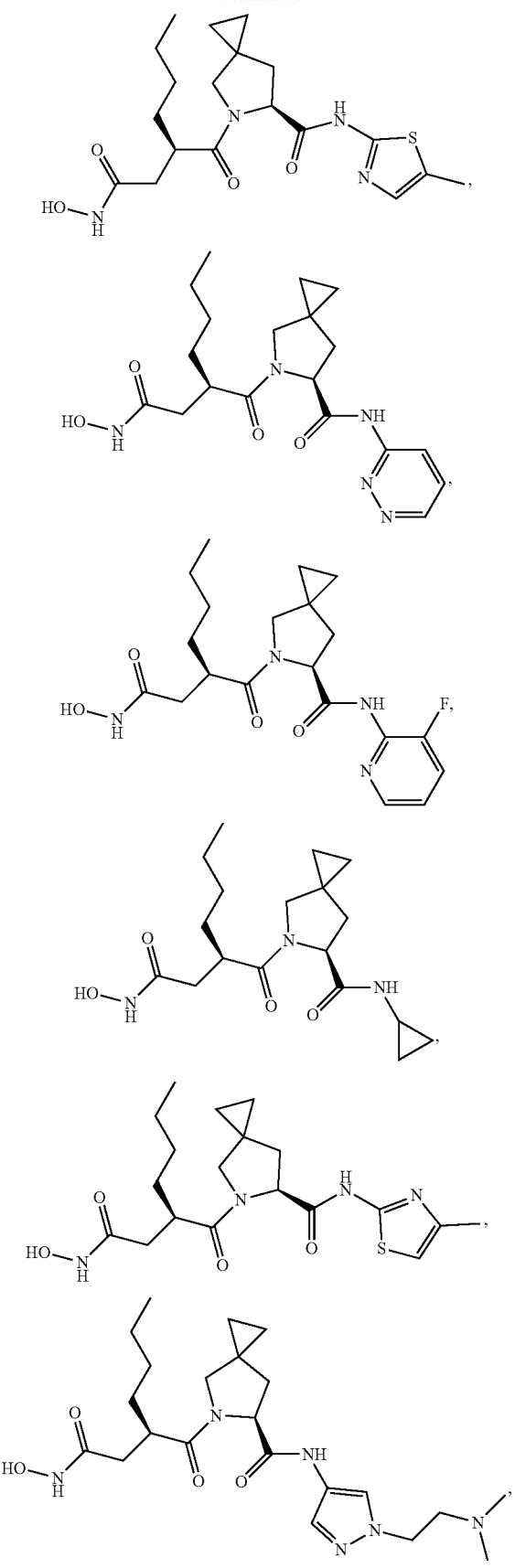

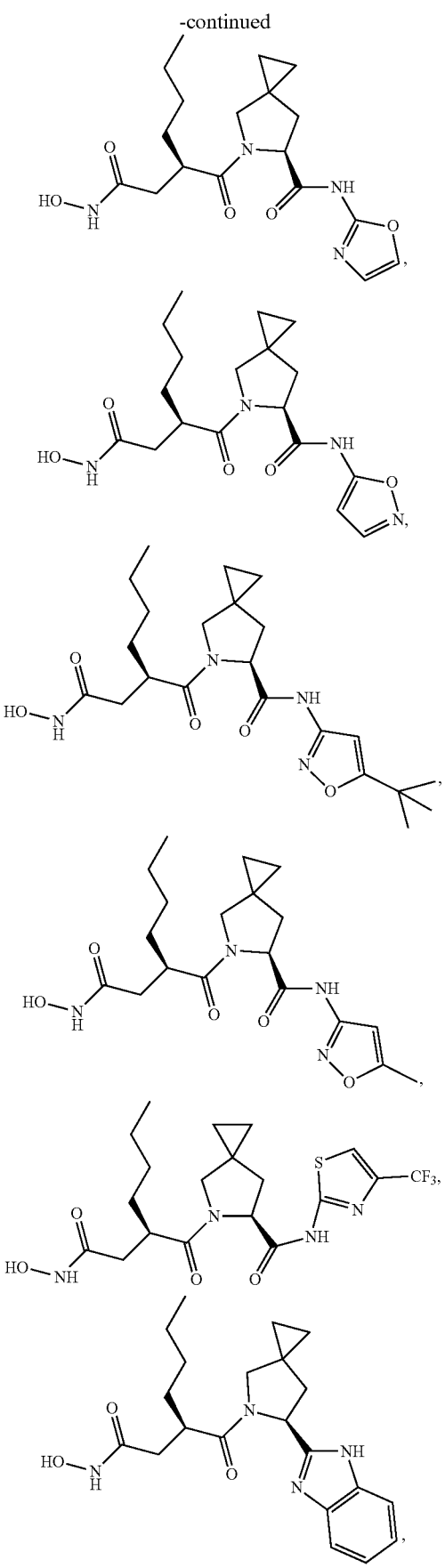
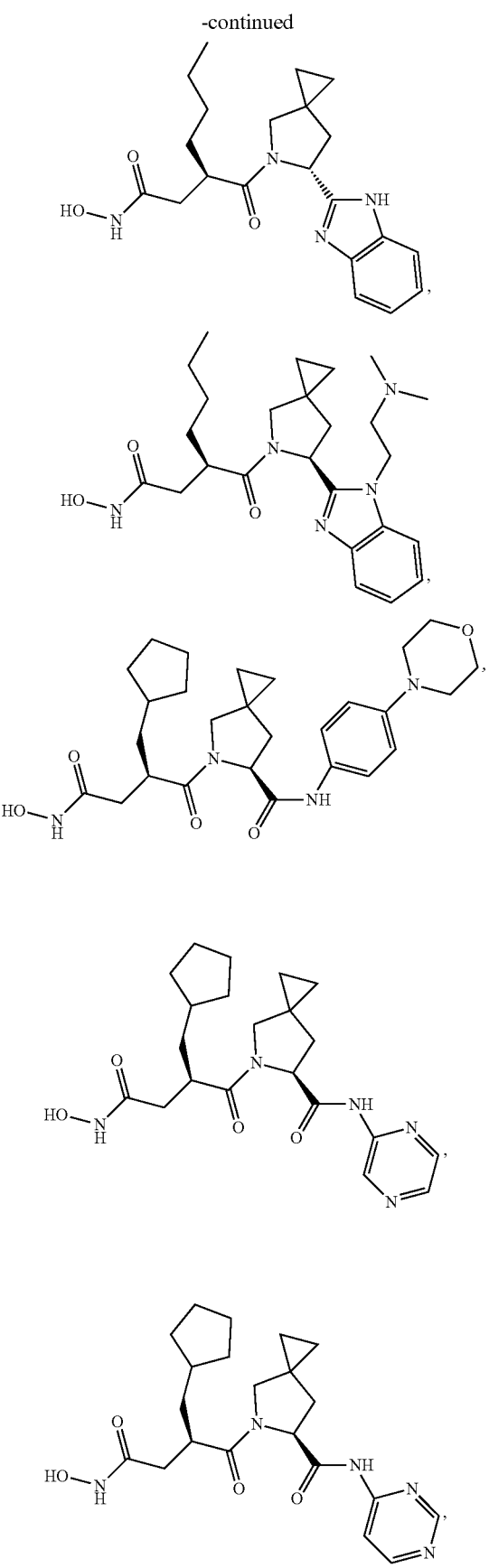

153
-continued
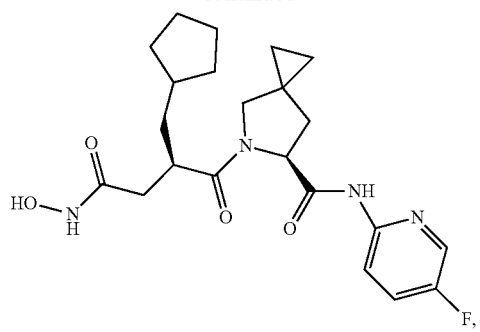
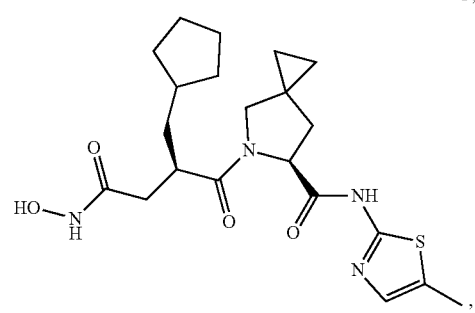
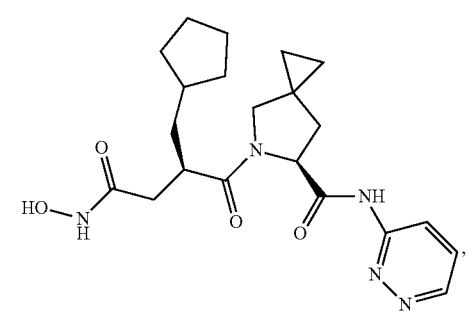
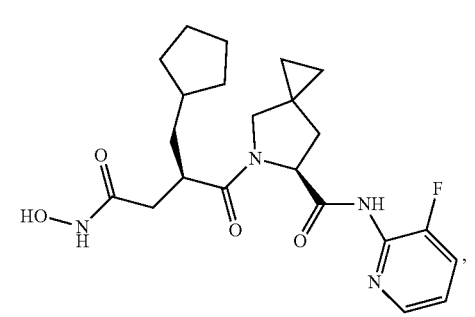
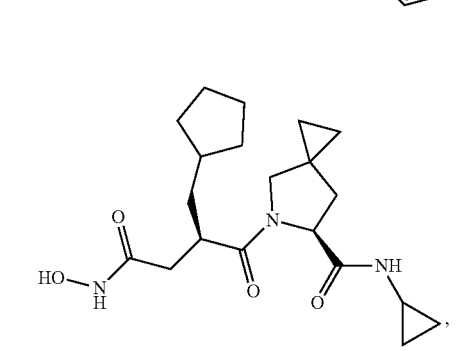
154
-continued
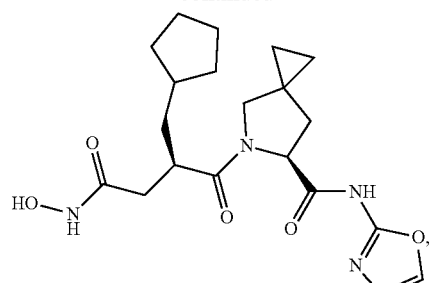
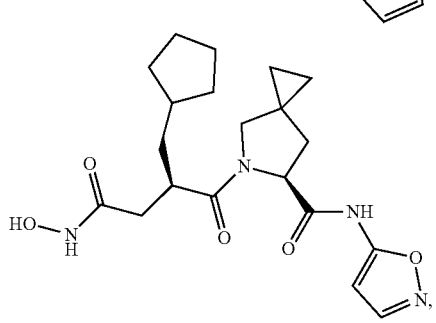
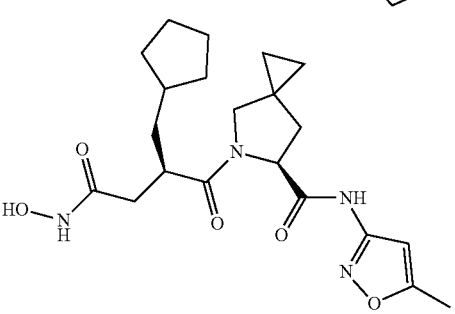
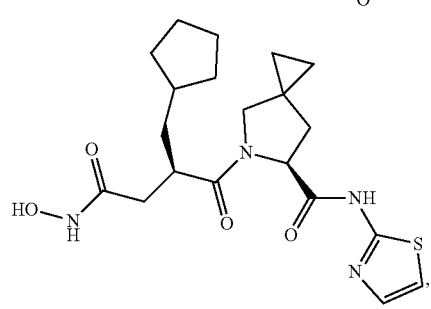
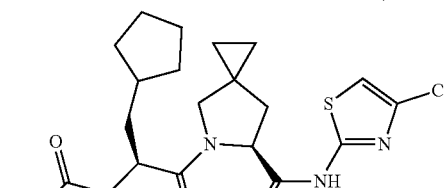
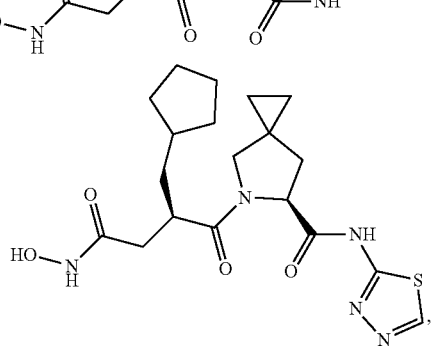

-continued
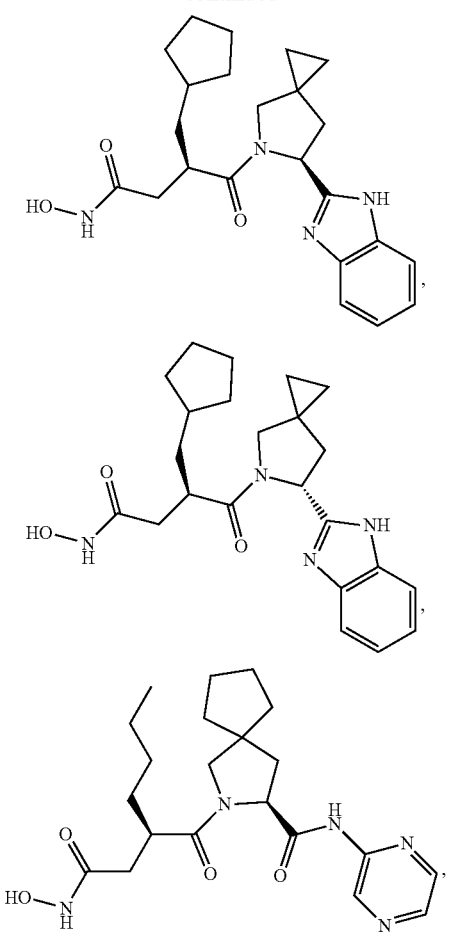
-continued
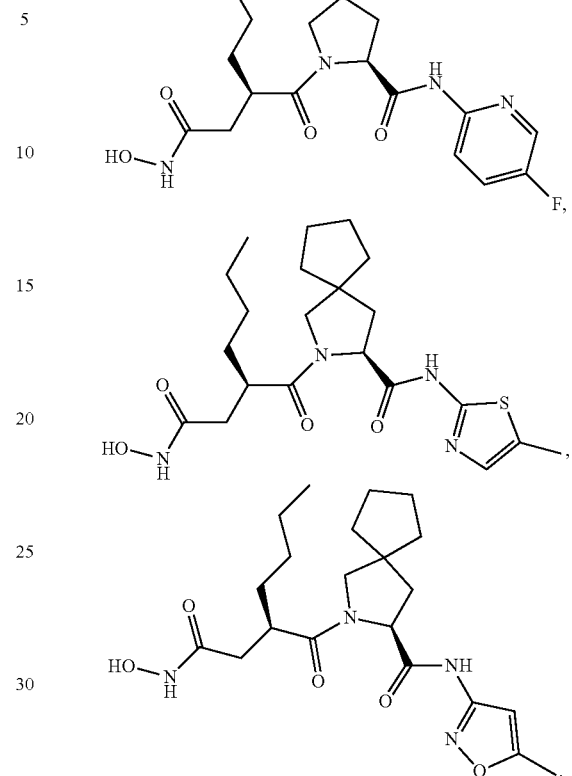
10. A pharmaceutical composition comprising the spiro three-membered ring, spiro five-membered ring peptide deformylase inhibitor according to any one of claims 1 to 9, and a pharmaceutically acceptable carrier.
* * * * *